United States Patent
Mengel et al.

(10) Patent No.: US 9,682,974 B2
(45) Date of Patent: Jun. 20, 2017

(54) HETEROARYL SUBSTITUTED PYRAZOLES

(71) Applicant: BAYER PHARMA AKTIENGESELLSCHAFT, Berlin (DE)

(72) Inventors: Anne Mengel, Berlin (DE); Anja Richter, Berlin (DE); Marion Hitchcock, Brookline (DE); Hans Briem, Berlin (DE); Gerhard Siemeister, Berlin (DE); Wilhelm Bone, Berlin (DE); Amaury Ernesto Fernandez-Montalvan, Berlin (DE); Jens Schröder, Berlin (DE); Simon Holton, Berlin (DE); Cornelia Preuße, Berlin (DE); Ursula Mönning, Woltersdorf (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/032,957

(22) PCT Filed: Oct. 27, 2014

(86) PCT No.: PCT/EP2014/072941
§ 371 (c)(1),
(2) Date: Apr. 28, 2016

(87) PCT Pub. No.: WO2015/063003
PCT Pub. Date: May 7, 2015

(65) Prior Publication Data
US 2016/0326159 A1     Nov. 10, 2016

(30) Foreign Application Priority Data
Oct. 30, 2013   (EP) ................... 13190857

(51) Int. Cl.
| | | |
|---|---|---|
| *C07D 403/14* | (2006.01) | |
| *A61K 31/506* | (2006.01) | |
| *C07D 417/14* | (2006.01) | |
| *C07D 401/14* | (2006.01) | |
| *A61K 31/4439* | (2006.01) | |
| *A61K 31/5377* | (2006.01) | |
| *A61K 45/06* | (2006.01) | |

(52) U.S. Cl.
CPC ........ *C07D 417/14* (2013.01); *A61K 31/4439* (2013.01); *A61K 31/506* (2013.01); *A61K 31/5377* (2013.01); *A61K 45/06* (2013.01); *C07D 401/14* (2013.01); *C07D 403/14* (2013.01)

(58) Field of Classification Search
CPC .. C07D 401/14; C07D 403/14; C07D 417/14; A61K 31/4155; A61K 31/4439; A61K 31/506

USPC ....... 544/122, 328; 546/272.4, 275.4, 275.7; 514/235.8, 256, 339, 340, 341
See application file for complete search history.

(56) References Cited

FOREIGN PATENT DOCUMENTS

| | | |
|---|---|---|
| WO | WO-2011049988 | 4/2011 |
| WO | WO-2011115804 | 9/2011 |
| WO | WO-2011126903 | 10/2011 |
| WO | WO-2012003405 | 1/2012 |
| WO | WO-2013050438 | 4/2013 |
| WO | WO 2013/092512 * | 6/2013 |
| WO | WO-2013092512 | 6/2013 |
| WO | WO-2013101830 | 7/2013 |
| WO | WO-2013167698 | 11/2013 |
| WO | WO-2014047111 | 3/2014 |
| WO | WO-2014047325 | 3/2014 |
| WO | WO-2014147144 | 9/2014 |
| WO | WO-2014147203 | 9/2014 |
| WO | WO-2014147204 | 9/2014 |
| WO | WO-2014202583 | 12/2014 |
| WO | WO-2014202584 | 12/2014 |
| WO | WO-2014202586 | 12/2014 |
| WO | WO-2014202588 | 12/2014 |
| WO | WO-2014202590 | 12/2014 |
| WO | WO-2015063003 | 5/2015 |
| WO | WO-2016041925 | 3/2016 |
| WO | WO-2016042080 | 3/2016 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*
Krenn et al., Structural analysis reveals features of the spindle checkpoint kinase Bub1-kinetochore subunit Knl1 interaction, J Cell Biol. vol. 196, No. 4, pp. 451-467, Feb. 2012.*
Simone, Oncology: Introduction, Cecil Textbook of Medicine, 20th Edition, vol. 1, pp. 1004-101 O, 1996.*

(Continued)

*Primary Examiner* — Deepak Rao
(74) *Attorney, Agent, or Firm* — Morrison & Foerster LLP

(57) ABSTRACT

Compounds of formula (I), processes for their preparation and their use as pharmaceuticals.

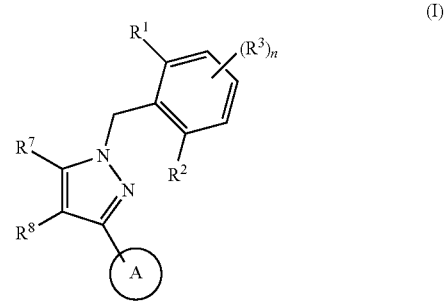

8 Claims, No Drawings

(56) References Cited

FOREIGN PATENT DOCUMENTS

| WO | WO-2016042081 | 3/2016 |
|---|---|---|
| WO | WO-2016042084 | 3/2016 |

OTHER PUBLICATIONS

Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*

* cited by examiner

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: synthetic peptide Biotin-Ahx-VLLPKKSFAEPG

<400> SEQUENCE: 1

Val Leu Leu Pro Lys Lys Ser Phe Ala Glu Pro Gly
1               5                   10
```

HETEROARYL SUBSTITUTED PYRAZOLES

CROSS REFERENCE TO RELATED APPLICATIONS

This application is the national stage of International Application No. PCT/EP2014/072941, filed internationally on Oct. 27, 2014, which claims the benefit of European Application No. 13190857.6, filed Oct. 30, 2013, the disclosures of which are hereby incorporated by reference in their entireties for all purposes.

FIELD OF APPLICATION OF THE INVENTION

The invention relates to substituted benzylpyrazole compounds, a process for their production and the use thereof.

BACKGROUND OF THE INVENTION

One of the most fundamental characteristics of cancer cells is their ability to sustain chronic proliferation whereas in normal tissues the entry into and progression through the cell division cycle is tightly controlled to ensure a homeostasis of cell number and maintenance of normal tissue function. Loss of proliferation control was emphasized as one of the six hallmarks of cancer [Hanahan D and Weinberg R A, Cell 100, 57, 2000; Hanahan D and Weinberg R A, Cell 144, 646, 2011].

The eukaryotic cell division cycle (or cell cycle) ensures the duplication of the genome and its distribution to the daughter cells by passing through a coordinated and regulated sequence of events. The cell cycle is divided into four successive phases:
1. The G1 phase represents the time before the DNA replication, in which the cell grows and is sensitive to external stimuli.
2. In the S phase the cell replicates its DNA, and
3. in the G2 phase preparations are made for entry into mitosis.
4. In mitosis (M phase), the duplicated chromosomes get separated supported by a spindle device built from microtubules, and cell division into two daughter cells is completed.

To ensure the extraordinary high fidelity required for an accurate distribution of the chromosomes to the daughter cells, the passage through the cell cycle is strictly regulated and controlled. The enzymes that are necessary for the progression through the cycle must be activated at the correct time and are also turned off again as soon as the corresponding phase is passed. Corresponding control points ("checkpoints") stop or delay the progression through the cell cycle if DNA damage is detected, or the DNA replication or the creation of the spindle device is not yet completed. The mitotic checkpoint (also known as spindle checkpoint or spindle assembly checkpoint) controls the accurate attachment of mircrotubules of the spindle device to the kinetochors (the attachment site for microtubules) of the duplicated chromosomes. The mitotic checkpoint is active as long as unattached kinetochores are present and generates a wait-signal to give the dividing cell the time to ensure that each kinetochore is attached to a spindle pole, and to correct attachment errors. Thus the mitotic checkpoint prevents a mitotic cell from completing cell division with unattached or erroneously attached chromosomes [Suijkerbuijk S J and Kops G J, Biochem. Biophys. Acta 1786, 24, 2008; Musacchio A and Salmon E D, Nat. Rev. Mol. Cell. Biol. 8, 379, 2007]. Once all kinetochores are attached with the mitotic spindle poles in a correct bipolar (amphitelic) fashion, the checkpoint is satisfied and the cell enters anaphase and proceeds through mitosis.

The mitotic checkpoint is established by a complex network of a number of essential proteins, including members of the MAD (mitotic arrest deficient, MAD 1-3) and Bub (Budding uninhibited by benzimidazole, Bub 1-3) families, Mps1 kinase, cdc20, as well as other components [reviewed in Bolanos-Garcia V M and Blundell T L, Trends Biochem. Sci. 36, 141, 2010], many of these being over-expressed in proliferating cells (e.g. cancer cells) and tissues [Yuan B et al., Clin. Cancer Res. 12, 405, 2006]. The major function of an unsatisfied mitotic checkpoint is to keep the anaphase-promoting complex/cyclosome (APC/C) in an inactive state. As soon as the checkpoint gets satisfied the APC/C ubiquitin-ligase targets cyclin B and securin for proteolytic degradation leading to separation of the paired chromosomes and exit from mitosis.

Inactive mutations of the Ser/Thr kinase Bub1 prevented the delay in progression through mitosis upon treatment of cells of the yeast S. cerevisiae with microtubule-destabilizing drugs, which led to the identification of Bub1 as a mitotic checkpoint protein [Roberts B T et al., Mol. Cell Biol., 14, 8282, 1994]. A number of recent publications provide evidence that Bub1 plays multiple roles during mitosis which, have been reviewed by Elowe [Elowe S, Mol. Cell. Biol. 31, 3085, 2011]. In particular, Bub1 is one of the first mitotic checkpoint proteins that binds to the kinetochores of duplicated chromosomes and probably acts as a scaffolding protein to constitute the mitotic checkpoint complex. Furthermore, via phosphorylation of histone H2A, Bub1 localizes the protein shugoshin to the centromeric region of the chromosomes to prevent premature segregation of the paired chromosomes [Kawashima et al. Science 327, 172, 2010]. In addition, together with a Thr-3 phosphorylated Histone H3 the shugoshin protein functions as a binding site for the chromosomal passenger complex which includes the proteins survivin, borealin, INCENP and Aurora B. The chromosomal passenger complex is seen as a tension sensor within the mitotic checkpoint mechanism, which dissolves erroneously formed microtubule-kinetochor attachments such as syntelic (both sister kinetochors are attached to one spindle pole) or merotelic (one kinetochor is attached to two spindle poles) attachments [Watanabe Y, Cold Spring Harb. Symp. Quant. Biol. 75, 419, 2010].

Incomplete mitotic checkpoint function has been linked with aneuploidy and tumourigenesis [Weaver B A and Cleveland D W, Cancer Res. 67, 10103, 2007; King R W, Biochim Biophys Acta 1786, 4, 2008]. In contrast, complete inhibition of the mitotic checkpoint has been recognised to result in severe chromosome missegregation and induction of apoptosis in tumour cells [Kops G J et al., Nature Rev. Cancer 5, 773, 2005; Schmidt M and Medema R H, Cell Cycle 5, 159, 2006; Schmidt M and Bastians H, Drug Res. Updates 10, 162, 2007]. Thus, mitotic checkpoint abrogation through pharmacological inhibition of components of the mitotic checkpoint, such as Bub1 kinase, represents a new approach for the treatment of proliferative disorders, including solid tumours such as carcinomas, sarcomas, leukaemias and lymphoid malignancies or other disorders, associated with uncontrolled cellular proliferation.

The present invention relates to chemical compounds that inhibit Bub1 kinase. Established anti-mitotic drugs such as vinca alkaloids, taxanes or epothilones activate the mitotic checkpoint, inducing a mitotic arrest either by stabilising or destabilising microtubule dynamics. This arrest prevents separation of the duplicated chromosomes to form the two daughter cells. Prolonged arrest in mitosis forces a cell either into mitotic exit without cytokinesis (mitotic slippage or adaption) or into mitotic catastrophe leading to cell death [Rieder C L and Maiato H, Dev. Cell 7, 637, 2004]. In contrast, inhibitors of Bub1 prevent the establishment and/or functionality of the mitotic checkpoint and/or microtubule-kinetochor attachment error correction mechanisms, which finally results in severe chromosomal missegregation, induction of apoptosis and cell death.

These findings suggest that Bub1 inhibitors should be of therapeutic value for the treatment of proliferative disorders associated with enhanced uncontrolled proliferative cellular processes such as, for example, cancer, inflammation, arthritis, viral diseases, cardiovascular diseases, or fungal diseases in a warm-blooded animal such as man.

WO 2013/050438 discloses substituted benzylindazole derivatives which are Bub1 kinase inhibitors.

WO 2013/092512 discloses substituted benzylpyrazole derivatives which are Bub1 kinase inhibitors.

WO 2013/167698 discloses substituted benzylcycloalkylpyrazoles, which are Bub1 kinase inhibitors.

WO 2014/147144 discloses diaminoheteroaryl substituted indazole derivatives, which are Bub1 kinase inhibitors.

WO 2014/147203 discloses heteroaryl substituted indazole derivatives, which are Bub1 kinase inhibitors.

WO 2014/147204 discloses heteroaryl substituted indazole derivatives, which are Bub1 kinase inhibitors.

Due to the fact that especially cancer disease as being expressed by uncontrolled proliferative cellular processes in tissues of different organs of the human- or animal body still is not considered to be a controlled disease in that sufficient drug therapies already exist, there is a strong need to provide further new therapeutically useful drugs, preferably inhibiting new targets and providing new therapeutic options (e.g. drugs with improved pharmacological properties).

DESCRIPTION OF THE INVENTION

Therefore, inhibitors of Bub1 represent valuable compounds that should complement therapeutic options either as single agents or in combination with other drugs.

In accordance with a first aspect, the invention relates to compounds of formula (I)

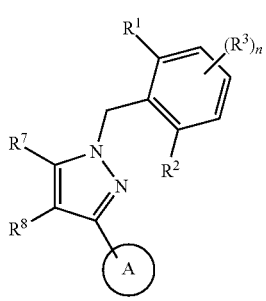

in which

represents a

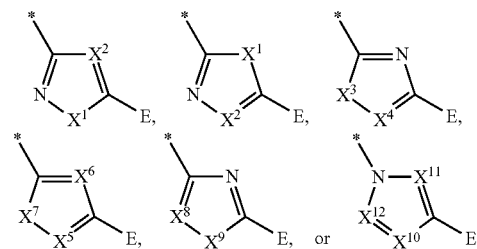

group, whereby the * is the point of attachment,
wherein
$X^1$ is $NR^{18}$, O, or S,
$X^2$ is $CR^4$, or N,
$X^3$ is $NR^{18}$, O, or S,
$X^4$ is $CR^4$, or N,
$X^5$ is $CR^4$, or N,
$X^6$ is $CR^4$,
$X^7$ is $NR^{18}$,
$X^8$ is $CR^4$,
$X^9$ is $NR^{18}$, O, or S,
$X^{10}$ is $CR^4$, or N,
$X^{11}$ is $CR^4$, or N,
$X^{12}$ is $CR^4$, or N,
in which group
E represents a

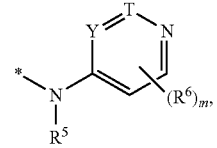

group,
whereby the * is the point of attachment,
T is CH, $CR^{17}$ or N,
Y is CH, $CR^{17}$ or N,
whereby one or both of T and Y represent CH or $CR^{17}$,
and
$R^1/R^2$ are independently from each other hydrogen, or halogen,
$R^3$ is independently from each other 1-6C-alkyl, 1-6C-alkoxy, halogen, 2-6C-alkenyl, 3-6C-cycloalkyl, 1-6C-haloalkoxy, or C(O)OH,
n is 0, 1, 2 or 3,
or
$R^3$ is -(1-6C-alkylene)-S—$R^{14}$, -(1-6C-alkylene)-S(O)—$R^{14}$, -(1-6C-alkylene)-S(O)$_2$—$R^{14}$, -(1-6C-alkylene)-S(=O)(=$NR^{15}$)$R^{14}$, —O-(1-6C-alkylene)-S—$R^{14}$, —O-(1-6C-alkylene)-S(O)—$R^{14}$, —O-(1-6C-alkylene)-S(O)$_2$—$R^{14}$, or —O-(1-6C-alkylene)-S(=O)(=$NR^{15}$)$R^{14}$,
and
n is 1,
$R^4$ is independently from each other
(a) hydrogen,
(b) hydroxy,
(c) 1-6C-alkoxy optionally substituted with
(c1) 1 or 2 hydroxy,
(c2) —$NR^9R^{10}$,
(c3) —S—$R^{14}$,
(c4) —S(O)—$R^{14}$, (c5) —S(O)₂—R¹⁴,
(c6) —S(=O)(=NR¹⁵)R¹⁴,
(c7) —S(O)₂NR⁹R¹⁰,
(d)

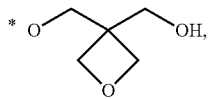

whereby the * is the point of attachment,
(e)

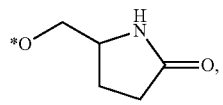

whereby the * is the point of attachment,
(f) cyano, or
(g) —S(O)₂-(1-4C-alkyl),
R⁵ is
(a) hydrogen,
(b) 2-6C-hydroxyalkyl,
(c)

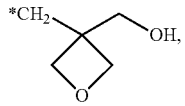

whereby the * is the point of attachment,
(d) —C(O)-(1-6C-alkyl),
(e) —C(O)-(1-6C-alkylene)-O-(1-6C-alkyl), or
(f) —C(O)-(1-6C-alkylene)-O-(1-6C-alkylene)-O-(1-6C-alkyl),
R⁶ is independently from each other halogen, cyano, —C(O)NR¹¹R¹², or —C(O)OR¹³,
m is 0, 1, or 2,
R⁷ is hydrogen, halogen, cyano, 1-6C-alkyl, 2-6C-alkenyl, 1-6C-alkoxy, 1-6C-haloalkoxy, 3-6C-cycloalkyl, —C(O)NR¹¹R¹² or —NR⁹R¹⁰,
R⁸ is hydrogen, halogen, cyano, 1-6C-alkyl, 2-6C-alkenyl, 1-6C-alkoxy, 1-6C-haloalkoxy, 3-6C-cycloalkyl or —NR⁹R¹⁰,
or
R⁷ and R⁸ form together with the two carbon atoms to which they are attached a 6-membered aromatic ring, which is optionally substituted independently one or more times with halogen or 1-3C-alkyl,
or
R⁷ and R⁸ form together a n-propylene or a n-butylene group,
R⁹, R¹⁰ are independently from each other hydrogen, 1-6C-alkyl or together with the nitrogen atom to which they are attached form a 4-6-membered heterocyclic ring optionally containing one further heteroatom selected from the group consisting of O, S or N,
R¹¹, R¹² are independently from each other hydrogen, 1-6C-alkyl, 2-6C-hydroxyalkyl, or (1-4C-alkyl)-S(O)₂-(1-4C-alkyl), R¹³ is independently from each other hydrogen or 1-4C-alkyl,
R¹⁴ is independently from each other a group selected from 1-6C-alkyl, 3-7C-cycloalkyl, phenyl and benzyl,
wherein said group is optionally substituted with one or two or three substituents, identically or differently, selected from the group of hydroxy, halogen, or —NR⁹R¹⁰,
R¹⁵ is independently from each other hydrogen, cyano, or —C(O)R¹⁶,
R¹⁶ is 1-6C-alkyl, or 1-6C-haloalkyl,
R¹⁷ is independently from each other halogen, cyano, —C(O)NR¹¹R¹², or —C(O)OR¹³,
R¹⁸ is
  (a) hydrogen,
  (b) 1-6C-alkyl optionally substituted with
    (b1) 1 or 2 hydroxy,
    (b2) 1-6C-alkoxy,
    (b3) —C(O)OR¹³,
    (b4) —C(O)NR¹¹R¹²,
    (b5) —NR⁹R¹⁰,
    (b6) —S—R¹⁴,
    (b7) —S(O)—R¹⁴,
    (b8) —S(O)₂—R¹⁴,
    (b9) —S(=O)(=NR¹⁵)R¹⁴,
    (b10) —S(O)₂NR⁹R¹⁰,
  (c) —S(O)₂-(1-4C-alkyl),
  (d) —C(O)-(1-6C-alkyl),
or an N-oxide, a salt, a tautomer or a stereoisomer of said compound, or a salt of said N-oxide, tautomer or stereoisomer.

In accordance with a second aspect, the invention relates to compounds of formula (I) wherein

represents a

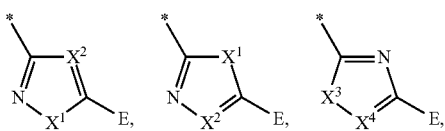

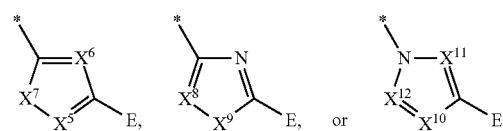

group, whereby the * is the point of attachment,
  wherein
    X¹ is NR¹⁸, O, or S,
    X² is CR⁴, or N,
    X³ is NR¹⁸, O, or S,
    X⁴ is CR⁴, or N,
    X⁵ is CR⁴, or N,
    X⁶ is CR⁴,
    X⁷ is NR¹⁸,
    X⁸ is CR⁴,
    X⁹ is NR¹⁸, O, or S, $X^{10}$ is $CR^4$, or N,
$X^{11}$ is $CR^4$, or N,
$X^{12}$ is $CR^4$, or N,
in which group
E represents a

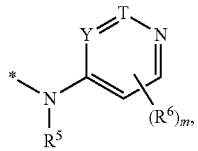

group,
whereby the * is the point of attachment,
T is CH, $CR^{17}$ or N,
Y is CH, $CR^{17}$ or N,
whereby one or both of T and Y represent CH or $CR^{17}$,
and
$R^1/R^2$ are independently from each other hydrogen, or halogen,
$R^3$ is independently from each other 1-3C-alkoxy,
n is 0, 1, 2, or 3,
or
  $R^3$ is -(1-4C-alkylene)-S—$R^{14}$, -(1-4C-alkylene)-S(O)—$R^{14}$, -(1-4C-alkylene)-S(O)$_2$—$R^{14}$, -(1-4C-alkylene)-S(=O)(=N$R^{15}$)$R^{14}$, —O-(1-4C-alkylene)-S—$R^{14}$, —O-(1-4C-alkylene)-S(O)—$R^{14}$, —O-(1-4C-alkylene)-S(O)$_2$—$R^{14}$, or —O-(1-4C-alkylene)-S(=O)(=N$R^{15}$)$R^{14}$,
and
n is 1,
$R^4$ is independently from each other
  (a) hydrogen,
  (b) hydroxy,
  (c) 1-4C-alkoxy optionally substituted with
    (c1) 1 or 2 hydroxy,
    (c2) —N$R^9R^{10}$,
    (c3) —S—$R^{14}$,
    (c4) —S(O)—$R^{14}$,
    (c5) —S(O)$_2$—$R^{14}$,
    (c6) —S(=O)(=N$R^{15}$)$R^{14}$,
    (c7) —S(O)$_2$N$R^9R^{10}$,
  (f) cyano, or
  (g) —S(O)$_2$-(1-4C-alkyl),
$R^5$ is hydrogen,
  $R^6$ is independently from each other halogen, cyano, —C(O)N$R^{11}R^{12}$, or —C(O)O$R^{13}$,
m is 0, 1, or 2,
$R^7$ is hydrogen, halogen, cyano, 1-3C-alkyl, 2-3C-alkenyl, 1-3C-alkoxy, 1-3C-haloalkoxy, 3-6C-cycloalkyl, —C(O)N$R^{11}R^{12}$ or —N$R^9R^{10}$,
$R^8$ is hydrogen, halogen, cyano, 1-3C-alkyl, 2-3C-alkenyl, 1-3C-alkoxy, 1-3C-haloalkoxy, 3-6C-cycloalkyl or —N$R^9R^{10}$,
or
$R^7$ and $R^8$ form together with the two carbon atoms to which they are attached a 6-membered aromatic ring, which is optionally substituted independently one or more times with halogen or 1-3C-alkyl,
$R^9$, $R^{10}$ are independently from each other hydrogen or 1-3C-alkyl, or together with the nitrogen atom to which they are attached form a 4-6-membered heterocyclic ring optionally containing one further heteroatom selected from the group consisting of O, S or N,
$R^{11}$, $R^{12}$ are independently from each other hydrogen, 1-3C-alkyl, or 2-3C-hydroxyalkyl,
$R^{13}$ is independently from each other hydrogen or 1-3C-alkyl,
$R^{14}$ is independently from each other a group selected from 1-3C-alkyl, and 3-7C-cycloalkyl,
$R^{15}$ is independently from each other hydrogen, cyano, or —C(O)$R^{16}$,
$R^{16}$ is methyl, or trifluoromethyl,
$R^{17}$ is independently from each other halogen, cyano, —C(O)N$R^{11}R^{12}$, or —C(O)O$R^{13}$,
$R^{18}$ is
  (a) hydrogen,
  (b) 1-4C-alkyl optionally substituted with
    (b1) 1 or 2 hydroxy,
    (b2) 1-3C-alkoxy,
    (b3) —C(O)O$R^{13}$,
    (b4) —C(O)N$R^{11}R^{12}$,
    (b5) —N$R^9R^{10}$,
    (b6) —S—$R^{14}$,
    (b7) —S(O)—$R^{14}$,
    (b8) —S(O)$_2$—$R^{14}$,
    (b9) —S(=O)(=N$R^{15}$)$R^{14}$,
    (b10) —S(O)$_2$N$R^9R^{10}$,
  (c) —S(O)$_2$-(1-4C-alkyl),
  (d) —C(O)-(1-3C-alkyl),
or an N-oxide, a salt, a tautomer or a stereoisomer of said compound, or a salt of said N-oxide, tautomer or stereoisomer.

Another aspect of the invention are compounds of formula (I), wherein

represents a

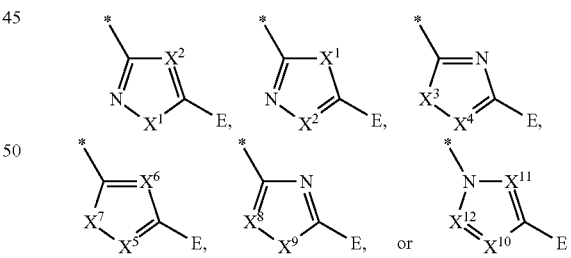

group, whereby the * is the point of attachment,
wherein
  $X^1$ is $NR^{18}$, O, or S,
  $X^2$ is $CR^4$, or N,
  $X^3$ is $NR^{18}$, O, or S,
  $X^4$ is $CR^4$, or N,
  $X^5$ is $CR^4$, or N,
  $X^6$ is $CR^4$,
  $X^7$ is $NR^{18}$,
  $X^8$ is $CR^4$,
  $X^9$ is $NR^{18}$, O, or S,
  $X^{10}$ is $CR^4$, or N, $X^{11}$ is $CR^4$, or N,
$X^{12}$ is $CR^4$, or N,
in which group
E represents a

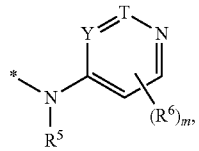

group,
whereby the * is the point of attachment,
T is CH, $CR^{17}$ or N,
Y is CH, $CR^{17}$ or N,
whereby one or both of T and Y represent CH or $CR^{17}$,
and
$R^1/R^2$ are independently from each other hydrogen, or halogen,
$R^3$ is 1-3C-alkoxy,
n is 0, or 1,
$R^4$ is independently from each other
  (a) hydrogen,
  (c) 1-4C-alkoxy optionally substituted with
    (c1) hydroxy,
    (c3) —S—$R^{14}$,
    (c4) —S(O)—$R^{14}$,
    (c5) —S(O)$_2$—$R^{14}$,
    (c6) —S(=O)(=N$R^{15}$)$R^{14}$, or
    (c7) —S(O)$_2$N$R^9R^{10}$,
$R^5$ is hydrogen,
$R^6$ is —C(O)N$R^{11}R^{12}$, or —C(O)O$R^{13}$,
m is 0, or 1,
$R^7$ is 3-6C-cycloalkyl,
$R^8$ is 1-3C-alkyl,
or
$R^7$ and $R^8$ form together with the two carbon atoms to which they are attached a 6-membered aromatic ring, which is optionally substituted independently one or more times with halogen or 1-3C-alkyl,
$R^9$, $R^{10}$ are independently from each other hydrogen or 1-3C-alkyl, or together with the nitrogen atom to which they are attached form a 4-6-membered heterocyclic ring optionally containing one further heteroatom selected from the group consisting of O, S or N,
$R^{11}$, $R^{12}$ are independently from each other hydrogen, or 1-3C-alkyl,
$R^{13}$ is independently from each other hydrogen or 1-3C-alkyl,
$R^{14}$ is 1-3C-alkyl,
$R^{15}$ is hydrogen,
$R^{17}$ is independently from each other —C(O)N$R^{11}R^{12}$, or —C(O)O$R^{13}$,
$R^{18}$ is
  (a) hydrogen,
  (b) 1-4C-alkyl optionally substituted with
    (b1) hydroxy,
    (b2) 1-3C-alkoxy,
    (b3) —C(O)O$R^{13}$,
    (b4) —C(O)N$R^{11}R^{12}$,
    (b5) —N$R^9R^{10}$,
    (b6) —S—$R^{14}$,
    (b7) —S(O)—$R^{14}$,
    (b8) —S(O)$_2$—$R^{14}$,
    (b9) —S(=O)(=N$R^{15}$)$R^{14}$,
  (d) —C(O)-(1-3C-alkyl),
or an N-oxide, a salt, a tautomer or a stereoisomer of said compound, or a salt of said N-oxide, tautomer or stereoisomer.

A further aspect of the invention relates to compounds of formula (I)
wherein

represents a

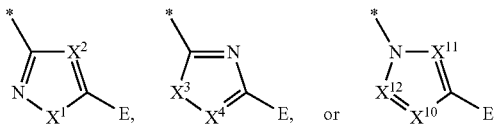

group, whereby the * is the point of attachment,
  wherein
    $X^1$ is $NR^{18}$, or S,
    $X^2$ is $CR^4$, or N,
    $X^3$ is $NR^{18}$,
    $X^4$ is N,
    $X^{10}$ is $CR^4$,
    $X^{11}$ is $CR^4$,
    $X^{12}$ is N,
  in which group
    E represents a

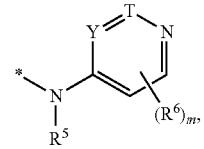

group,
whereby the * is the point of attachment,
T is CH,
Y is CH, or N,
and
$R^1/R^2$ are independently from each other hydrogen, or fluoro,
$R^3$ is ethoxy,
n is 0, or 1,
$R^4$ is
  (a) hydrogen,
$R^5$ is hydrogen,
$R^6$ is —C(O)O$R^{13}$,
m is 0, or 1,
$R^7$ is cyclopropyl,
$R^8$ is methyl,
or
$R^7$ and $R^8$ form together with the two carbon atoms to which they are attached a 6-membered aromatic ring,
$R^9$, $R^{10}$ together with the nitrogen atom to which they are attached form a morpholine ring
$R^{13}$ is independently from each other hydrogen or ethyl, $R^{14}$ is methyl,
$R^{18}$ is
(a) hydrogen,
(b) 1-2C-alkyl optionally substituted with
  (b1) hydroxy,
  (b2) methoxy,
  (b3) —C(O)OR$^{13}$,
  (b5) —NR$^9$R$^{10}$,
  (b8) —S(O)$_2$—R$^{14}$,
(d) acetyl,
or an N-oxide, a salt, a tautomer or a stereoisomer of said compound, or a salt of said N-oxide, tautomer or stereoisomer.

A further aspect of the invention relates to compounds of formula (I) selected from the group consisting of:

5'-cyclopropyl-1'-(4-ethoxy-2,6-difluorobenzyl)-4'-methyl-1-[2-(morpholin-4-yl)-ethyl]-N-(pyrimidin-4-yl)-1H,1'H-3,3'-bipyrazol-5-amine, 1-[5'-cyclopropyl-1'-(4-ethoxy-2,6-difluorobenzyl)-4'-methyl-5-(pyrimidin-4-ylamino)-1H,1'H-3,3'-bipyrazol-1-yl]ethanone,

[5'-cyclopropyl-1'-(4-ethoxy-2,6-difluorobenzyl)-4'-methyl-5-(pyrimidin-4-ylamino)-1H,1'H-3,3'-bipyrazol-1-yl]acetic acid, 5'-cyclopropyl-1'-(4-ethoxy-2,6-difluorobenzyl)-1,4'-di methyl-N-(pyrimidin-4-yl)-1H,1'H-3,3'-bipyrazol-5-amine, N-{3-[5-cyclopropyl-1-(4-ethoxy-2,6-difluorobenzyl)-4-methyl-1H-pyrazol-3-yl]-1-(2-methoxyethyl)-1H-1,2,4-triazol-5-yl}pyrimidin-4-amine, 5'-cyclopropyl-1'-(4-ethoxy-2,6-difluorobenzyl)-4'-methyl-1-[2-(methylsulfonyl)-ethyl]-N-(pyrimidin-4-yl)-1H,1'H-3,3'-bipyrazol-5-amine, 5'-cyclopropyl-1'-(4-ethoxy-2,6-difluorobenzyl)-1,4'-di methyl-N-(pyridin-4-yl)-1H,1'H-3,3'-bipyrazol-5-amine, N-{3-[5-cyclopropyl-1-(4-ethoxy-2,6-difluorobenzyl)-4-methyl-1H-pyrazol-3-yl]-1-(2-methoxyethyl)-1H-1,2,4-triazol-5-yl}pyridin-4-amine, 2-{3-[5-cyclopropyl-1-(4-ethoxy-2,6-difluorobenzyl)-4-methyl-1H-pyrazol-3-yl]-5-(pyridin-4-ylamino)-1H-1,2,4-triazol-1-yl}ethanol, N-{3-[5-cyclopropyl-1-(4-ethoxy-2,6-difluorobenzyl)-4-methyl-1H-pyrazol-3-yl]-1H-1,2,4-triazol-5-yl}pyridin-4-amine, ethyl 4-({3-[5-cyclopropyl-1-(4-ethoxy-2,6-difluorobenzyl)-4-methyl-1H-pyrazol-3-yl]-1-(2-methoxyethyl)-1H-1,2,4-triazol-5-yl}amino)nicotinate, N-{3-[1-(4-ethoxy-2,6-difluorobenzyl)-1H-indazol-3-yl]-1-(2-methoxyethyl)-1H-1,2,4-triazol-5-yl}pyridin-4-amine, N-{5-[1-(4-ethoxy-2,6-difluorobenzyl)-1H-indazol-3-yl]-1-(2-methoxyethyl)-1H-1,2,4-triazol-3-yl}pyridin-4-amine, N-{1-[1-(4-ethoxy-2,6-difluorobenzyl)-1H-indazol-3-yl]-1H-pyrazol-4-yl}pyrimidin-4-amine, and N-{3-[1-(2-fluorobenzyl)-1H-indazol-3-yl]-1,2,4-thiadiazol-5-yl}pyridin-4-amine, or an N-oxide, a salt, a tautomer or a stereoisomer of said compound, or a salt of said N-oxide, tautomer or stereoisomer.

One aspect of the invention are compounds of formula (I) as described in the examples, as characterized by their names in the title, as claimed in claim 5 and/or their structures as well as the subcombinations of all residues specifically disclosed in the compounds of the examples.

Another aspect of the present invention are the intermediates used for the synthesis of the compounds of formula (I) and the use of such intermediates for the synthesis of the compounds of formula (I) or a N-oxide, a salt, a tautomer or a stereoisomer of said compound, or a salt of said N-oxide, tautomer or stereoisomer.

Further aspect of the invention are compounds of formula (I), which are present as their salts.

Another embodiment of the invention are compounds according to the claims as disclosed in the Claims section wherein the definitions are limited according to the preferred or more preferred definitions as disclosed below or specifically or especially disclosed residues of the exemplified compounds and subcombinations thereof.

If embodiments of the invention as disclosed herein relate to compounds of formula (I), it is understood that those embodiments refer to the compounds of formula (I) as disclosed in any of the claims and the examples.

A further aspect of the invention relates to compounds of formula (I)
wherein

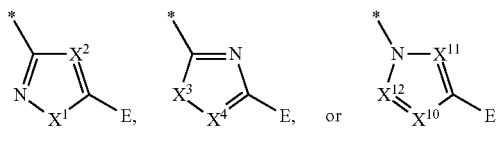

represents a

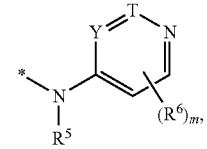

group, whereby the * is the point of attachment,
wherein
  $X^1$ is NR$^{18}$, or S,
  $X^2$ is CR$^4$, or N,
  $X^3$ is NR$^{18}$,
  $X^4$ is N,
  $X^{10}$ is CR$^4$,
  $X^{11}$ is CR$^4$,
  $X^{12}$ is N,
in which group
  E represents a group,
whereby the * is the point of attachment,
T is CH,
Y is CH, or N,
and
$R^1/R^2$ are independently of each other hydrogen, or halogen,
$R^3$ is 1-6C-alkoxy,
n is 0, or 1,
$R^4$ is hydrogen, $R^5$ is hydrogen,
$R^6$ is $C(O)OR^{13}$,
m is 0, or 1,
$R^7$ is 3-6C-cycloalkyl,
$R^8$ is 1-6C-alkyl,
or
$R^7$ and $R^8$ form together with the two carbon atoms to which they are attached a 6-membered aromatic ring,
$R^9$, $R^{10}$ together with the nitrogen atom to which they are attached form a 4-6-membered heterocyclic ring optionally containing one further heteroatom selected from the group consisting of O,
$R^{13}$ is hydrogen or 1-4C-alkyl,
$R^{14}$ is 1-6C-alkyl,
$R^{18}$ is
  (a) hydrogen,
  (b) 1-6C-alkyl optionally substituted with
    (b1) hydroxy,
    (b2) 1-6C-alkoxy,
    (b3) —$C(O)OR^{13}$,
    (b5) —$NR^9R^{10}$,
    (b8) —$S(O)_2$—$R^{14}$,
  (d) —$C(O)$-(1-6C-alkyl),
or an N-oxide, a salt, a tautomer or a stereoisomer of said compound, or a salt of said N-oxide, tautomer or stereoisomer.

Another aspect of the invention are compounds of formula (I), as defined supra, in which

represents a

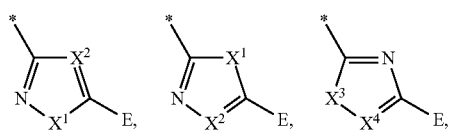

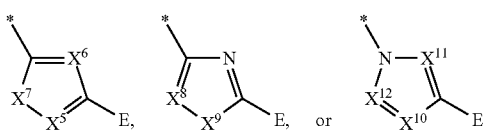

group, whereby the * is the point of attachment,
wherein
  $X^1$ is $NR^{18}$, O, or S,
  $X^2$ is $CR^4$, or N,
  $X^3$ is $NR^{18}$, O, or S,
  $X^4$ is $CR^4$, or N,
  $X^5$ is $CR^4$, or N,
  $X^6$ is $CR^4$,
  $X^7$ is $NR^{18}$,
  $X^8$ is $CR^4$,
  $X^9$ is $NR^{18}$, O, or S,
  $X^{10}$ is $CR^4$, or N,
  $X^{11}$ is $CR^4$, or N,
  $X^{12}$ is $CR^4$, or N,
in which group
E represents a

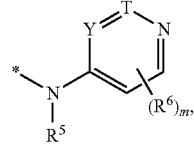

group,
whereby the * is the point of attachment,
T is CH, $CR^{17}$ or N,
Y is CH, $CR^{17}$ or N,
whereby one or both of T and Y represent CH or $CR^{17}$.

Another aspect of the invention are compounds of formula (I), as defined supra, in which

represents a

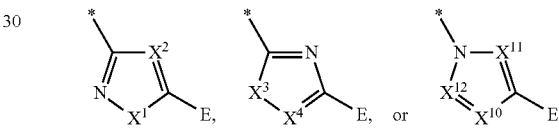

group, whereby the * is the point of attachment,
wherein
  $X^1$ is $NR^{18}$, or S,
  $X^2$ is $CR^4$, or N,
  $X^3$ is $NR^{18}$,
  $X^4$ is N,
  $X^{10}$ is $CR^4$,
  $X^{11}$ is $CR^4$,
  $X^{12}$ is N,
in which group
E represents a

group,
whereby the * is the point of attachment,
T is CH,
Y is CH, or N.

Another aspect of the invention are compounds of formula (I), as defined supra, in which

represents a

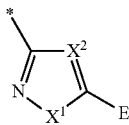

group, whereby the * is the point of attachment,
wherein
X¹ is NR¹⁸, or S,
X² is CR⁴, or N,
in which group
E represents a

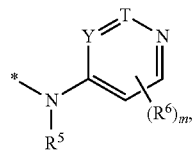

group,
whereby the * is the point of attachment,
T is CH,
Y is CH, or N.

Another aspect of the invention are compounds of formula (I), as defined supra, in which

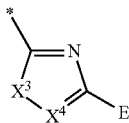

represents a

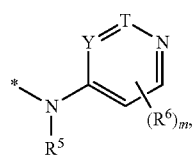

group, whereby the * is the point of attachment,
wherein
X³ is NR¹⁸,
X⁴ is N,
in which group
E represents a

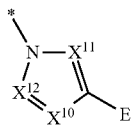

group,
whereby the * is the point of attachment,
T is CH,
Y is CH, or N.

Another aspect of the invention are compounds of formula (I), as defined supra, in which

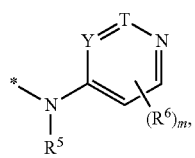

represents a

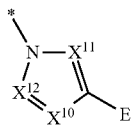

group, whereby the * is the point of attachment,
wherein
X¹⁰ is CR⁴,
X¹¹ is CR⁴,
X¹² is N,
in which group
E represents a

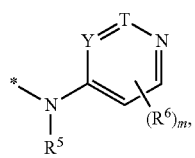

group,
whereby the * is the point of attachment,
T is CH,
Y is CH, or N.

Another aspect of the invention are compounds of formula (I), as defined supra, in which
R¹ is hydrogen, or halogen.

Another aspect of the invention are compounds of formula (I), as defined supra, in which
R¹ is hydrogen, or fluoro.

Another aspect of the invention are compounds of formula (I), as defined supra, in which
R¹ is hydrogen.

Another aspect of the invention are compounds of formula (I), as defined supra, in which
R¹ is fluoro.

Another aspect of the invention are compounds of formula (I), as defined supra, in which
R² is hydrogen, or halogen.

Another aspect of the invention are compounds of formula (I), as defined supra, in which
R² is hydrogen, or fluoro.

Another aspect of the invention are compounds of formula (I), as defined supra, in which
R² is hydrogen.

Another aspect of the invention are compounds of formula (I), as defined supra, in which
R² is fluoro.

Another aspect of the invention are compounds of formula (I), as defined supra, in which
R³ is 1-6C-alkyl, 1-6C-alkoxy, halogen, 2-6C-alkenyl, 3-6C-cycloalkyl, 1-6C-haloalkoxy, or C(O)OH.

Another aspect of the invention are compounds of formula (I), as defined supra, in which
$R^3$ is 1-3C-alkoxy.

Another aspect of the invention are compounds of formula (I), as defined supra, in which
$R^3$ is ethoxy.

Another aspect of the invention are compounds of formula (I), as defined supra, in which
n is 0, 1, 2 or 3.

Another aspect of the invention are compounds of formula (I), as defined supra, in which
n is 0, or 1.

Another aspect of the invention are compounds of formula (I), as defined supra, in which
n is 1.

Another aspect of the invention are compounds of formula (I), as defined supra, in which
n is 0.

Another aspect of the invention are compounds of formula (I), as defined supra, in which
$R^3$ is -(1-6C-alkylene)-S—$R^{14}$, -(1-6C-alkylene)-S(O)—$R^{14}$, -(1-6C-alkylene)-S(O)$_2$—$R^{14}$, -(1-6C-alkylene)-S(=O)(=N$R^{15}$)$R^{14}$, —O-(1-6C-alkylene)-S—$R^{14}$, —O-(1-6C-alkylene)-S(O)—$R^{14}$, —O-(1-6C-alkylene)-S(O)$_2$—$R^{14}$, or —O-(1-6C-alkylene)-S(=O)(=N$R^{15}$)$R^{14}$,
and
n is 1.

Another aspect of the invention are compounds of formula (I), as defined supra, in which
$R^3$ is -(1-4C-alkylene)-S—$R^{14}$, -(1-4C-alkylene)-S(O)—$R^{14}$, -(1-4C-alkylene)-S(O)$_2$—$R^{14}$, -(1-4C-alkylene)-S(=O)(=N$R^{15}$)$R^{14}$, —O-(1-4C-alkylene)-S—$R^{14}$, —O-(1-4C-alkylene)-S(O)—$R^{14}$, —O-(1-4C-alkylene)-S(O)$_2$—$R^{14}$, or —O-(1-4C-alkylene)-S(=O)(=N$R^{15}$)$R^{14}$,
and
n is 1.

Another aspect of the invention are compounds of formula (I), as defined supra, in which
$R^4$ is
(a) hydrogen,
(b) hydroxy,
(c) 1-6C-alkoxy optionally substituted with
  (c1) 1 or 2 hydroxy,
  (c2) —N$R^9R^{10}$,
  (c3) —S—$R^{14}$,
  (c4) —S(O)—$R^{14}$,
  (c5) —S(O)$_2$—$R^{14}$,
  (c6) —S(=O)(=N$R^{15}$)$R^{14}$,
  (c7) —S(O)$_2$N$R^9R^{10}$,
(d)

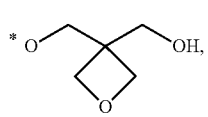

whereby the * is the point of attachment,
(e)

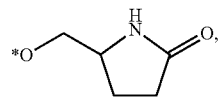

whereby the * is the point of attachment,
(f) cyano, or
(g) —S(O)$_2$-(1-4C-alkyl).

Another aspect of the invention are compounds of formula (I), as defined supra, in which
$R^4$ is
(a) hydrogen,
(b) hydroxy,
(c) 1-4C-alkoxy optionally substituted with
  (c1) 1 or 2 hydroxy,
  (c2) —N$R^9R^{10}$,
  (c3) —S—$R^{14}$,
  (c4) —S(O)—$R^{14}$,
  (c5) —S(O)$_2$—$R^{14}$,
  (c6) —S(=O)(=N$R^{15}$)$R^{14}$,
  (c7) —S(O)$_2$N$R^9R^{10}$,
(f) cyano, or
(g) —S(O)$_2$-(1-4C-alkyl).

Another aspect of the invention are compounds of formula (I), as defined supra, in which
$R^4$ is
(a) hydrogen,
(c) 1-4C-alkoxy optionally substituted with
  (c1) hydroxy,
  (c3) —S—$R^{14}$,
  (c4) —S(O)—$R^{14}$,
  (c5) —S(O)$_2$—$R^{14}$,
  (c6) —S(=O)(=N$R^{15}$)$R^{14}$, or
  (c7) —S(O)$_2$N$R^9R^{10}$.

Another aspect of the invention are compounds of formula (I), as defined supra, in which
$R^4$ is hydrogen.

Another aspect of the invention are compounds of formula (I), as defined supra, in which
$R^5$ is
(a) hydrogen,
(b) 2-6C-hydroxyalkyl,
(c)

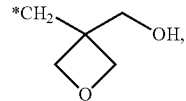

whereby the * is the point of attachment,
(d) —C(O)-(1-6C-alkyl),
(e) —C(O)-(1-6C-alkylene)-O-(1-6C-alkyl), or
(f) —C(O)-(1-6C-alkylene)-O-(1-6C-alkylene)-O-(1-6C-alkyl).

Another aspect of the invention are compounds of formula (I), as defined supra, in which
$R^5$ is hydrogen.

Another aspect of the invention are compounds of formula (I), as defined supra, in which
$R^6$ is halogen, cyano, C(O)N$R^{11}R^{12}$, or C(O)O$R^{13}$.

Another aspect of the invention are compounds of formula (I), as defined supra, in which
$R^6$ is halogen or cyano.

Another aspect of the invention are compounds of formula (I), as defined supra, in which
$R^6$ is C(O)N$R^{11}R^{12}$, or C(O)O$R^{13}$.

Another aspect of the invention are compounds of formula (I), as defined supra, in which
$R^6$ is C(O)O$R^{13}$.

Another aspect of the invention are compounds of formula (I), as defined supra, in which
m is 0, 1, or 2.

Another aspect of the invention are compounds of formula (I), as defined supra, in which
m is 0, or 1.

Another aspect of the invention are compounds of formula (I), as defined supra, in which
m is 1.

Another aspect of the invention are compounds of formula (I), as defined supra, in which
m is 0.

Another aspect of the invention are compounds of formula (I), as defined supra, in which
$R^7$ is hydrogen, halogen, cyano, 1-6C-alkyl, 2-6C-alkenyl, 1-6C-alkoxy, 1-6C-haloalkoxy, 3-6C-cycloalkyl, C(O)NR$^{11}$R$^{12}$ or NR$^9$R$^{10}$.

Another aspect of the invention are compounds of formula (I), as defined supra, in which
$R^7$ is hydrogen, halogen, cyano, 1-3C-alkyl, 2-3C-alkenyl, 1-3C-alkoxy, 1-3C-haloalkoxy, 3-6C-cycloalkyl, C(O)NR$^{11}$R$^{12}$ or NR$^9$R$^{10}$.

Another aspect of the invention are compounds of formula (I), as defined supra, in which
$R^7$ is 3-6C-cycloalkyl.

Another aspect of the invention are compounds of formula (I), as defined supra, in which
$R^7$ is cyclopropyl.

Another aspect of the invention are compounds of formula (I), as defined supra, in which
$R^7$ is hydrogen, halogen, cyano, 1-6C-alkyl, 2-6C-alkenyl, 1-6C-alkoxy, 1-6C-haloalkoxy, 3-6C-cycloalkyl.

Another aspect of the invention are compounds of formula (I), as defined supra, in which
$R^8$ is hydrogen, halogen, cyano, 1-6C-alkyl, 2-6C-alkenyl, 1-6C-alkoxy, 1-6C-haloalkoxy, 3-6C-cycloalkyl or NR$^9$R$^{10}$.

Another aspect of the invention are compounds of formula (I), as defined supra, in which
$R^8$ is hydrogen, halogen, cyano, 1-3C-alkyl, 2-3C-alkenyl, 1-3C-alkoxy, 1-3C-haloalkoxy, 3-6C-cycloalkyl or NR$^9$R$^{10}$.

Another aspect of the invention are compounds of formula (I), as defined supra, in which
$R^8$ is 1-3C-alkyl.

Another aspect of the invention are compounds of formula (I), as defined supra, in which
$R^8$ is methyl.

Another aspect of the invention are compounds of formula (I), as defined supra, in which
$R^8$ is hydrogen, halogen, cyano, 1-3C-alkyl, 2-3C-alkenyl, 1-3C-alkoxy, 1-3C-haloalkoxy or 3-6C-cycloalkyl.

Another aspect of the invention are compounds of formula (I), as defined supra, in which
$R^7$ and $R^8$ form together with the two carbon atoms to which they are attached a 6-membered aromatic ring, which is optionally substituted independently one or more times with halogen or 1-3C-alkyl.

Another aspect of the invention are compounds of formula (I), as defined supra, in which
$R^7$ and $R^8$ form together with the two carbon atoms to which they are attached a 6-membered aromatic ring.

Another aspect of the invention are compounds of formula (I), as defined supra, in which
$R^7$ and $R^8$ form together a n-propylene or a n-butylene group.

Another aspect of the invention are compounds of formula (I), as defined supra, in which
$R^9$ is hydrogen or 1-6C-alkyl.

Another aspect of the invention are compounds of formula (I), as defined supra, in which
$R^9$ is hydrogen or 1-3C-alkyl.

Another aspect of the invention are compounds of formula (I), as defined supra, in which
$R^{10}$ is hydrogen or 1-6C-alkyl.

Another aspect of the invention are compounds of formula (I), as defined supra, in which
$R^{10}$ is hydrogen or 1-3C-alkyl.

Another aspect of the invention are compounds of formula (I), as defined supra, in which
$R^9$ and $R^{10}$ together with the nitrogen atom to which they are attached form a 4-6-membered heterocyclic ring optionally containing one further heteroatom selected from the group consisting of 0, S or N, Another aspect of the invention are compounds of formula (I), as defined supra, in which
$R^9$ and $R^{10}$ together with the nitrogen atom to which they are attached form a morpholine ring.

Another aspect of the invention are compounds of formula (I), as defined supra, in which
$R^{11}$ is hydrogen, 1-6C-alkyl, 2-6C-hydroxyalkyl, or (1-4C-alkyl)-S(O)$_2$-(1-4C-alkyl).

Another aspect of the invention are compounds of formula (I), as defined supra, in which
$R^{11}$ is hydrogen, 1-3C-alkyl, or 2-3C-hydroxyalkyl.

Another aspect of the invention are compounds of formula (I), as defined supra, in which
$R^{11}$ is hydrogen, or 1-3C-alkyl.

Another aspect of the invention are compounds of formula (I), as defined supra, in which
$R^{12}$ is hydrogen, 1-6C-alkyl, 2-6C-hydroxyalkyl, or (1-4C-alkyl)-S(O)$_2$-(1-4C-alkyl).

Another aspect of the invention are compounds of formula (I), as defined supra, in which
$R^{12}$ is hydrogen, or 1-3C-alkyl.

Another aspect of the invention are compounds of formula (I), as defined supra, in which
$R^{12}$ is hydrogen, 1-3C-alkyl, or 2-3C-hydroxyalkyl.

Another aspect of the invention are compounds of formula (I), as defined supra, in which
$R^{13}$ is hydrogen or 1-4C-alkyl.

Another aspect of the invention are compounds of formula (I), as defined supra, in which
$R^{13}$ is hydrogen or 1-3C-alkyl.

Another aspect of the invention are compounds of formula (I), as defined supra, in which
$R^{13}$ is hydrogen or ethyl.

Another aspect of the invention are compounds of formula (I), as defined supra, in which
$R^{13}$ is hydrogen.

Another aspect of the invention are compounds of formula (I), as defined supra, in which
$R^{13}$ is ethyl.

Another aspect of the invention are compounds of formula (I), as defined supra, in which
$R^{14}$ is a group selected from 1-6C-alkyl, 3-7C-cycloalkyl, phenyl, benzyl, wherein said group is optionally substituted with one or two or three substituents, identically or differently, selected from the group of hydroxy, halogen, or NR$^9$R$^{10}$.

Another aspect of the invention are compounds of formula (I), as defined supra, in which
$R^{14}$ is a group selected from 1-3C-alkyl, and 3-7C-cycloalkyl.

Another aspect of the invention are compounds of formula (I), as defined supra, in which
$R^{14}$ is 1-3C-alkyl.

Another aspect of the invention are compounds of formula (I), as defined supra, in which
$R^{14}$ is methyl.

Another aspect of the invention are compounds of formula (I), as defined supra, in which
$R^{15}$ is hydrogen, cyano, or $C(O)R^{16}$.

Another aspect of the invention are compounds of formula (I), as defined supra, in which
$R^{15}$ is hydrogen.

Another aspect of the invention are compounds of formula (I), as defined supra, in which
$R^{16}$ is 1-6C-alkyl, or 1-6C-haloalkyl.

Another aspect of the invention are compounds of formula (I), as defined supra, in which
$R^{16}$ is methyl, or trifluoromethyl.

Another aspect of the invention are compounds of formula (I), as defined supra, in which
$R^{16}$ is methyl.

Another aspect of the invention are compounds of formula (I), as defined supra, in which
$R^{16}$ is trifluoromethyl.

Another aspect of the invention are compounds of formula (I), as defined supra, in which
$R^{17}$ is halogen, cyano, $C(O)NR^{11}R^{12}$, or $C(O)OR^{13}$.

Another aspect of the invention are compounds of formula (I), as defined supra, in which
$R^{17}$ is $C(O)NR^{11}R^{12}$, or $C(O)OR^{13}$.

Another aspect of the invention are compounds of formula (I), as defined supra, in which
$R^{17}$ is $C(O)NR^{11}R^{12}$.

Another aspect of the invention are compounds of formula (I), as defined supra, in which
$R^{17}$ is $C(O)OR^{13}$.

Another aspect of the invention are compounds of formula (I), as defined supra, in which
$R^{18}$ is
(a) hydrogen,
(b) 1-6C-alkyl optionally substituted with
  (b1) 1 or 2 hydroxy,
  (b2) 1-6C-alkoxy,
  (b3) —$C(O)OR^{13}$,
  (b4) —$C(O)NR^{11}R^{12}$,
  (b5) —$NR^9R^{10}$,
  (b6) —S—$R^{14}$,
  (b7) —S(O)—$R^{14}$,
  (b8) —$S(O)_2$—$R^{14}$,
  (b9) —$S(=O)(=NR^{15})R^{14}$,
  (b10) —$S(O)_2NR^9R^{10}$,
(c) —$S(O)_2$-(1-4C-alkyl),
(d) —C(O)-(1-6C-alkyl).

Another aspect of the invention are compounds of formula (I), as defined supra, in which
$R^{18}$ is
(a) hydrogen,
(b) 1-4C-alkyl optionally substituted with
  (b1) 1 or 2 hydroxy,
  (b2) 1-3C-alkoxy,
  (b3) —$C(O)OR^{13}$,
  (b4) —$C(O)NR^{11}R^{12}$,
  (b5) —$NR^9R^{10}$,
  (b6) —S—$R^{14}$,
  (b7) —S(O)—$R^{14}$,
  (b8) —$S(O)_2$—$R^{14}$,
  (b9) —$S(=O)(=NR^{15})R^{14}$,
  (b10) —$S(O)_2NR^9R^{10}$,
(c) —$S(O)_2$-(1-4C-alkyl),
(d) —C(O)-(1-3C-alkyl).

Another aspect of the invention are compounds of formula (I), as defined supra, in which
$R^{18}$ is
(a) hydrogen,
(b) 1-4C-alkyl optionally substituted with
  (b1) hydroxy,
  (b2) 1-3C-alkoxy,
  (b3) —$C(O)OR^{13}$,
  (b4) —$C(O)NR^{11}R^{12}$,
  (b5) —$NR^9R^{10}$,
  (b6) —S—$R^{14}$,
  (b7) —S(O)—$R^{14}$,
  (b8) —$S(O)_2$—$R^{14}$,
  (b9) —$S(=O)(=NR^{15})R^{14}$,
(d) —C(O)-(1-3C-alkyl).

Another aspect of the invention are compounds of formula (I), as defined supra, in which
$R^{18}$ is
(a) hydrogen,
(b) 1-2C-alkyl optionally substituted with
  (b1) hydroxy,
  (b2) methoxy,
  (b3) —$C(O)OR^{13}$,
  (b5) —$NR^9R^{10}$,
  (b8) —$S(O)_2$—$R^{14}$,
(d) acetyl.

DEFINITIONS

Constituents which are optionally substituted as stated herein, may be substituted, unless otherwise noted, one or more times, independently from one another at any possible position. When any variable occurs more than one time in any constituent, each definition is independent. For example, when $R^3$, $R^4$, $R^6$, $R^9$, $R^{10}$, $R^{11}$, $R^{12}$, $R^{13}$, $R^{14}$, $R^{15}$ in and/or $R^{17}$ occur more than one time in any compound of formula (I) each definition of $R^3$, $R^4$, $R^6$, $R^9$, $R^{10}$, $R^{11}$, $R^{12}$, $R^{13}$, $R^{14}$, $R^{15}$ and $R^{17}$ is independent.

Unless defined otherwise in the claims and in the description, the constituents defined below can optionally be substituted, one or more times, identically or differently, with a substituent selected from:
hydroxy, halogen, cyano, 1-6C-alkyl, 1-4C-haloalkyl, 1-6C-alkoxy, —$NR^9R^{10}$, cyano, (=O), —$C(O)NR^{11}R^{12}$, —$C(O)OR^{13}$. An alkyl constituent being multiply substituted by halogen includes also a completely halogenated alkyl moiety such as e.g. $CF_3$.

Should a constituent be composed of more than one part, e.g. —O-(1-6C-alkyl)-(3-7C-cycloalkyl), the position of a possible substituent can be at any of these parts at any suitable position. A hyphen at the beginning or at the end of the constituent marks the point of attachment to the rest of the molecule. Should a ring be substituted the substituent could be at any suitable position of the ring, also on a ring nitrogen atom if suitable.

The term "comprising" when used in the specification includes "consisting of".

If it is referred to "as mentioned above" or "mentioned above" within the description it is referred to any of the disclosures made within the specification in any of the preceding pages.

"suitable" within the sense of the invention means chemically possible to be made by methods within the knowledge of a skilled person.

"1-6C-alkyl" is a straight-chain or branched alkyl group having 1 to 6 carbon atoms. Examples are methyl, ethyl, n-propyl, iso-propyl, n-butyl, iso-butyl, sec-butyl and tert-butyl, pentyl, hexyl, preferably 1-4 carbon atoms (1-4C-alkyl), more preferably 1-3 carbon atoms (1-3C-alkyl). Other alkyl constituents mentioned herein having another number of carbon atoms shall be defined as mentioned above taking into account the different length of their chain. Those parts of constituents containing an alkyl chain as a bridging moiety between two other parts of the constituent which usually is called an "alkylene" moiety is defined in line with the definition for alkyl above including the preferred length of the chain e.g. methylene, ethylene, n-propylene, iso-propylene, n-butylene, isobutylene, tert-butylene.

"2-6C-alkenyl" is a straight chain or branched alkenyl radical having 2 to 6 carbon atoms. Examples are the but-2-enyl, but-3-enyl (homoallyl), prop-1-enyl, prop-2-enyl (allyl) and the ethenyl (vinyl) radicals.

"Halogen" within the meaning of the present invention is iodine, bromine, chlorine or fluorine, preferably "halogen" within the meaning of the present invention is chlorine or fluorine.

"1-6C-haloalkyl" is a straight-chain or branched alkyl group having 1 to 6 carbon atoms in which at least one hydrogen is substituted by a halogen atom. Examples are chloromethyl or 2-bromoethyl. For a partially or completely fluorinated C1-C4-alkyl group, the following partially or completely fluorinated groups are considered, for example: fluoromethyl, difluoromethyl, trifluoromethyl, fluoroethyl, 1,1-difluoroethyl, 1,2-difluoroethyl, 1,1,1-trifluoroethyl, tetrafluoroethyl, and penta-fluoroethyl, whereby difluoromethyl, trifluoromethyl, or 1,1,1-trifluoroethyl are preferred. All possible partially or completely fluorinated 1-6C-alkyl groups are considered to be encompassed by the term 1-6C-haloalkyl.

"1-6C-hydroxyalkyl" is a straight-chain or branched alkyl group having 1 to 6 carbon atoms in which at least one hydrogen atom is substituted by a hydroxy group. Examples are hydroxymethyl, 1-hydroxyethyl, 2-hydroxyethyl, 1,2-dihydroxyethyl, 3-hydroxypropyl, 2-hydroxypropyl, 2,3-dihydroxypropyl, 3-hydroxy-2-methyl-propyl, 2-hydroxy-2-methyl-propyl, 1-hydroxy-2-methyl-propyl.

"1-6C-alkoxy" represents radicals, which in addition to the oxygen atom, contain a straight-chain or branched alkyl radical having 1 to 6 carbon atoms. Examples which may be mentioned are the hexoxy, pentoxy, butoxy, isobutoxy, sec-butoxy, tert-butoxy, propoxy, isopropoxy, ethoxy and methoxy radicals, preferred are methoxy, ethoxy, propoxy, isopropoxy. In case the alkoxy group may be substituted, substituents as defined (c1)-(c7) may be situated at any carbon atom of the alkoxy group being chemically suitable.

"1-6C-haloalkoxy" represents radicals, which in addition to the oxygen atom, contain a straight-chain or branched alkyl radical having 1 to 6 carbon atoms in which at least one hydrogen is substituted by a halogen atom. Examples are —O—CFH$_2$, —O—CF$_2$H, —O—CF$_3$, —O—CH$_2$—CFH$_2$, —O—CH$_2$—CF$_2$H, —O—CH$_2$—CF$_3$. Preferred are —O—CF$_2$H, —O—CF$_3$, —O—CH$_2$—CF$_3$.

"3-7C-cycloalkyl" stands for cyclopropyl, cyclobutyl, cyclopentyl, cyclohexyl or cycloheptyl, preferably cyclopropyl.

The NR$^9$R$^{10}$ group includes, for example, NH$_2$, N(H)CH$_3$, N(CH$_3$)$_2$, —N(H)CH$_2$CH$_3$ and —N(CH$_3$)CH$_2$CH$_3$.

The —C(O)NR$^{11}$R$^{12}$ group includes, for example, —C(O)NH$_2$, —C(O)N(H)CH$_3$, —C(O)N(CH$_3$)$_2$, —C(O)N(H)CH$_2$CH$_3$, —C(O)N(CH$_3$)CH$_2$CH$_3$ or —C(O)N(CH$_2$CH$_3$)$_2$. If R$^{11}$ or R$^{12}$ are not hydrogen, they may be substituted by hydroxy.

The —C(O)OR$^{13}$ group includes, for example, —C(O)OH, —C(O)OCH$_3$, —C(O)OC$_2$H$_5$, —C(O)OC$_3$H$_7$, —C(O)OCH(CH$_3$)$_2$, —C(O)OC$_4$H$_9$.

A "heterocyclic ring" represents a monocyclic, nonaromatic heterocyclic radical containing, 4 to 6 ring atoms, and 1 or 2 heteroatoms and/or hetero groups independently selected from the series consisting of N, O, S, SO, SO$_2$. The heterocyclyl radicals can be saturated or partially unsaturated and, unless stated otherwise, may be optionally substituted, one or more times, identically or differently, with a substituent selected from: 1-4C-alkyl, 1-4C-haloalkyl, 1-4C-alkoxy, hydroxy, fluorine or (=O) whereby the 1-4C-alkyl may be optionally further substituted with hydroxy and the double bonded oxygen atom leads to a carbonyl group together with the carbon atom of the heterocyclyl ring at any suitable position. Particularly preferred heterocyclic radicals are 4- to 6-membered monocyclic saturated heterocyclyl radicals having up to two hetero atoms from the series consisting of O, N and S, more preferred 5- to 6-membered heterocyclic radicals. The following may be mentioned by way of example and by preference: pyrrolidinyl, 3-hydroxypyrrolidinyl, piperidinyl, 3-hydroxypiperidinyl, 4-hydroxypiperidinyl, 3-fluoropiperidinyl, 3,3-difluoropiperidinyl, 4-fluoropiperidinyl, 4,4-difluoropiperidinyl, piperazinyl, N-methyl-piperazinyl, N-(2-hydroxyethyl)-piperazinyl, morpholinyl, thiomorpholinyl.

"6-membered aromatic ring" represents a phenyl ring.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or may achieve a combination of both effects.

Salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

One aspect of the invention are salts of the compounds according to the invention including all inorganic and organic acid addition salts, especially all pharmaceutically acceptable inorganic and organic acid addition salts, particularly all pharmaceutically acceptable inorganic and organic acid addition salts customarily used in pharmacy. Another aspect of the invention are the salts with di- and tricarboxylic acids.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)-benzoates, butyrates, salicylates, sulfosalicylates, lactates, maleates, laurates, malates, fumarates, succinates, oxalates, malonates, pyruvates, acetoacetates, tartarates, stearates, benzensulfonates, toluenesulfonates, methanesulfonates, trifluoromethansulfonates, 3-hydroxy-2-naphthoates, benzenesulfonates, naphthalinedisulfonates and trifluoroacetates.

Examples of salts with bases include, but are not limited to, lithium, sodium, potassium, calcium, aluminum, magnesium, titanium, meglumine, ammonium, salts optionally derived from $NH_3$ or organic amines having from 1 to 16 C-atoms such as e.g. ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and guanidinium salts.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x $CF_3COOH$", "x $Na^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

The salts include water-insoluble and, particularly, water-soluble salts.

According to the person skilled in the art the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

Any such combination of a compound of formula (I) of the present invention with an anti-cancer agent as defined below is an embodiment of the invention.

The term "(chemotherapeutic) anti-cancer agents", includes but is not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, copanlisib, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, enzalutamide, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, roniciclib, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The compounds according to the invention and their salts can exist in the form of tautomers which are included in the embodiments of the invention. Tautomers, sometimes referred to as proton-shift tautomers, are two or more compounds that are related by the migration of a hydrogen atom accompanied by the switch of one or more single bonds and one or more adjacent double bonds. The compounds of this invention may exist in one or more tautomeric forms.

The compounds of the invention may, depending on their structure, exist in different stereoisomeric forms. These forms include configurational isomers or optionally conformational isomers (enantiomers and/or diastereoisomers including those of atropisomers). The present invention therefore includes enantiomers, diastereoisomers as well as mixtures thereof. From those mixtures of enantiomers and/or disastereoisomers pure stereoisomeric forms can be isolated with methods known in the art, preferably methods of chromatography, especially high pressure liquid chromatography (HPLC) using achiral or chiral phase. The invention further includes all mixtures of the stereoisomers mentioned above independent of the ratio, including the racemates.

Furthermore, the present invention includes all possible crystalline forms, polymorphs of the compounds of the present invention, either as single polymorphs, or as a mixture of more than one polymorph, in any ratio.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

It has now been found, and this constitutes the basis of the present invention, that said compounds of the present invention have surprising and advantageous properties.

In particular, said compounds of the present invention have surprisingly been found to effectively inhibit Bub1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1 kinase, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The intermediates used for the synthesis of the compounds of claims 1-5 as described below, as well as their use for the synthesis of the compounds of claims 1-5, are one further aspect of the present invention. Preferred intermediates are the Intermediate Examples as disclosed below.

General Procedures

The compounds according to the invention can be prepared according to the following schemes 1 through 12.

The schemes and procedures described below illustrate synthetic routes to the compounds of general formula (I) of the invention and are not intended to be limiting. It is obvious to the person skilled in the art that the order of transformations as exemplified in the Schemes can be modified in various ways. The order of transformations exemplified in the Schemes is therefore not intended to be limiting. In addition, interconversion of any of the substituents, $R^1$, $R^2$, $R^3$, $R^4$, $R^5$, $R^6$, $R^7$, $R^{17}$ or $R^{18}$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

One route for the preparation of compounds of general formula (Ia) is described in Scheme 1a. In instances where this route is not feasible, Scheme 1b can be applied.

Scheme 1a

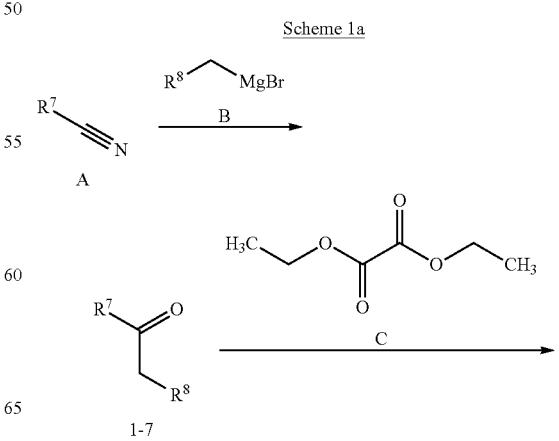

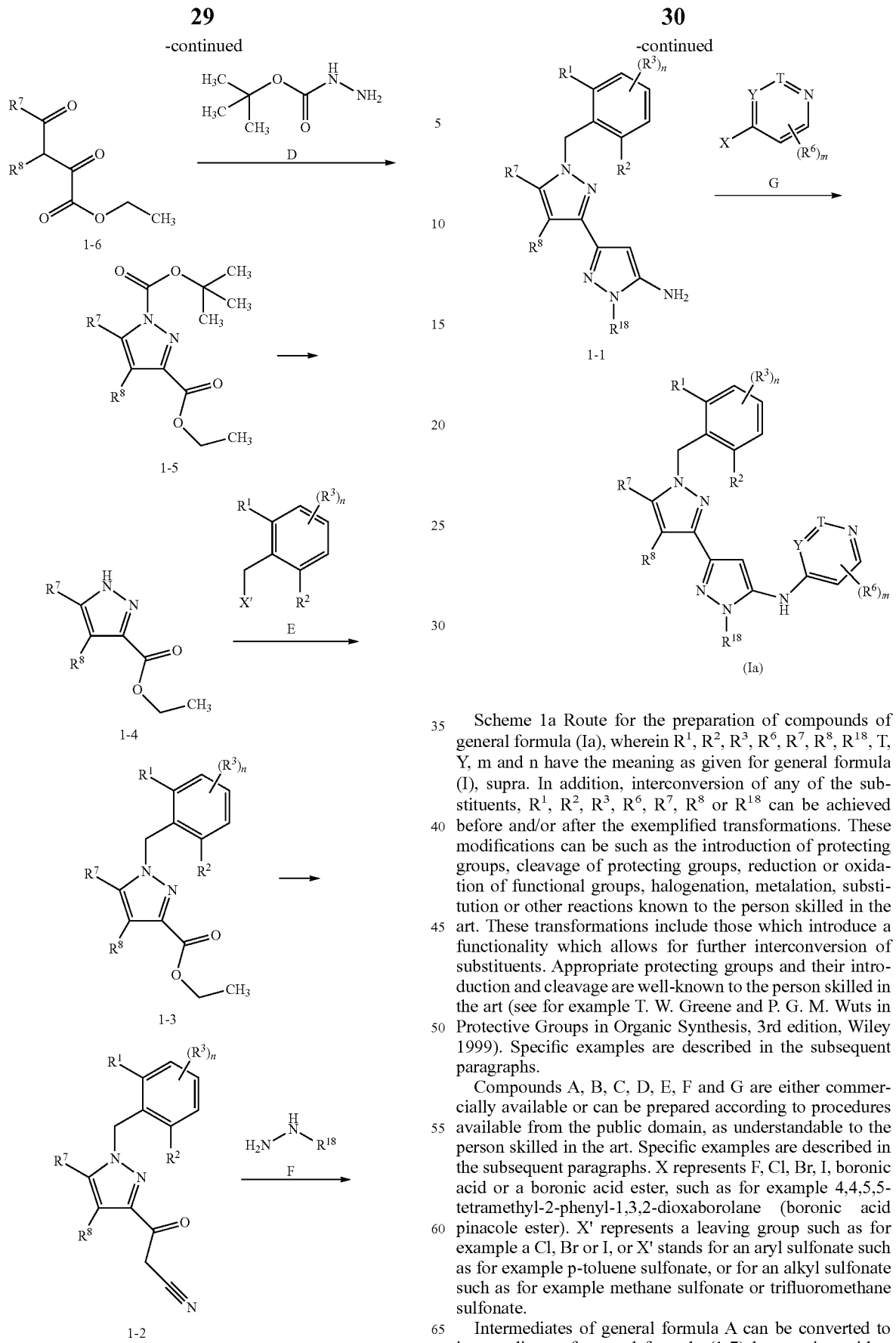

Scheme 1a Route for the preparation of compounds of general formula (Ia), wherein $R^1$, $R^2$, $R^3$, $R^6$, $R^7$, $R^8$, $R^{18}$, T, Y, m and n have the meaning as given for general formula (I), supra. In addition, interconversion of any of the substituents, $R^1$, $R^2$, $R^3$, $R^6$, $R^7$, $R^8$ or $R^{18}$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Specific examples are described in the subsequent paragraphs.

Compounds A, B, C, D, E, F and G are either commercially available or can be prepared according to procedures available from the public domain, as understandable to the person skilled in the art. Specific examples are described in the subsequent paragraphs. X represents F, Cl, Br, I, boronic acid or a boronic acid ester, such as for example 4,4,5,5-tetramethyl-2-phenyl-1,3,2-dioxaborolane (boronic acid pinacole ester). X' represents a leaving group such as for example a Cl, Br or I, or X' stands for an aryl sulfonate such as for example p-toluene sulfonate, or for an alkyl sulfonate such as for example methane sulfonate or trifluoromethane sulfonate.

Intermediates of general formula A can be converted to intermediates of general formula (1-7) by reaction with a suitable organometallic compound, such as, for example bromo(ethyl)magnesium, in a suitable solvent system, such as, for example, diethylether, at a temperature between 0° C. and boiling point of the respective solvent, preferably the reaction is carried out under reflux.

Intermediates of general formula (1-7) can be converted to intermediates of general formula (1-6) by reaction with a suitable oxalate (C), such as, for example diethyl oxalate, in the presence of a suitable base, such as, for example bis-(trimethylsilyl)lithiumamide, in a suitable solvent system, such as, for example, diethylether, at a temperature between −78° C. and room temperature, preferably the reaction is carried out at room temperature.

Compounds of general formula (1-6) are converted to intermediates of general formula (1-5) by treatment with tert-butyl hydrazinecarboxylate (D), in a suitable solvent system, such as, for example, ethanol, in a temperature range from room temperature to the boiling point of the respective solvent, preferably the reaction is carried out at the boiling point of the respective solvent.

Compounds of general formula (1-5) are converted to intermediates of general formula (1-4) by reaction under acidic conditions, such as, for example, by reaction with hydrochloric acid, in a suitable solvent system, such as, for example, dioxane, in a temperature range from 0° C. to room temperature, preferably the reaction is carried out at room temperature.

Intermediates of general formula (1-4) can be reacted with a suitably substituted benzyl halide or benzyl sulfonate of general formula (E), such as, for example, a benzyl bromide, in a suitable solvent system, such as, for example, tetrahydrofuran, in the presence of a suitable base, such as, for example, sodium hydride in a temperature range from 0° C. to the boiling point of the respective solvent, preferably the reaction is carried out at room temperature, to furnish compounds of general formula (1-3).

Intermediates of general formula (1-3) can be converted into intermediates of general formula (1-2) by reacting with deprotonated acetonitrile. Deprotonation of acetonitrile is carried out with a suitable base such as for example n-butyllithium in a suitable solvent system, such as, for example, tetrahydrofuran, in a temperature range from −78° C. to room temperature, preferably the reaction is carried at −78° C.

Intermediates of general formula (1-2) can be reacted with a suitably substituted hydrazine of general formula (F), such as, for example monomethylhydrazine, in a suitable solvent system, such as, for example, methanol, in a temperature range from room temperature to the boiling point of the respective solvent to furnish compounds of general formula (1-1).

Intermediates of general formula (1-1) can be reacted with a suitable halogen-substituted heteroaryl compounds of the general formula (G), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis-(diphenyl-phosphane), in a suitable solvent system, such as, for example, N,N-dimethylformamide, in a temperature range from room temperature to the boiling point of the respective solvent, preferably the reaction is carried out at 100° C. to furnish compounds of general formula (Ia). Alternatively the following palladium catalysts can be used:

allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands:

racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethyl-phosphonium tetrafluoroborate, 2-(di-tert-butylphosphino) biphenyl, tri-tert-butyl-phosphonium tetrafluoroborate, tri-2-furylphosphine, tris(2,4-di-tert-butylphenyl)-phosphite, tri-o-tolylphosphine.

Scheme 1b

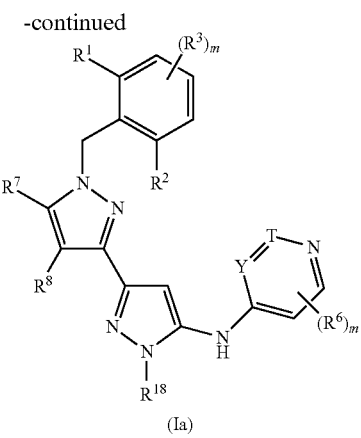

(Ia)

Scheme 1b. Alternative route for the preparation of compounds of general formula (Ia), wherein $R^1$, $R^2$, $R^3$, $R^6$, $R^7$, $R^8$, $R^{18}$, T, Y, m and n have the meaning as given for general formula (Ia), supra. In addition, interconversion of any of the substituents, $R^1$, $R^2$, $R^3$, $R^6$, $R^7$, $R^8$ or $R^{18}$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Specific examples are described in the subsequent paragraphs.

Compounds F and G are either commercially available or can be prepared according to procedures available from the public domain, as understandable to the person skilled in the art. Specific examples are described in the subsequent paragraphs. X represents F, Cl, Br, I, boronic acid or a boronic acid ester, such as for example 4,4,5,5-tetramethyl-2-phenyl-1,3,2-dioxaborolane (boronic acid pinacole ester).

Intermediates of general formula (1-2) can be reacted with a suitably substituted hydrazine of general formula (F), such as, for example (2-methanesulfonylethyl)hydrazine hydrochloride, in a suitable solvent system, such as, for example, acetic acid, in a temperature range from room temperature to the boiling point of the respective solvent to furnish compounds of general formula (1-1a).

Intermediates of general formula (1-1a) can be converted into intermediates of the general formula (1-1) by reaction with a suitable acid, such as, for example, aqueous hydrogen chloride in a suitable solvent such as, for example, methanol in a temperature range from room temperature to the boiling point of the respective solvent, preferably the reaction is carried out at 60° C. to furnish compounds of general formula (1-1).

Intermediates of general formula (Ia) can be reacted with a suitable halogen-substituted heteroaryl of the general formula (G), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis(diphenylphosphane), in a suitable solvent system, such as, for example, N,N-dimethylformamide, in a temperature range from room temperature to the boiling point of the respective solvent, preferably the reaction is carried out at 100° C. to furnish compounds of general formula (Id). Alternatively the following palladium catalysts can be used: allylpalladium chloride dimmer, dichlorobis(benzonitrile)palladium (II), palladium (II) acetate, palladium (II) chloride, tetrakis(triphenylphosphine)palladium (0), tris(dibenzylideneacetone) dipalladium (0) or the following ligands:

racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethyl-phosphonium tetrafluoroborate, 2-(di-tert-butylphosphino) biphenyl, tri-tert-butyl-phosphonium tetrafluoroborate, tri-2-furylphosphine, tris(2,4-di-tert-butylphenyl)-phosphite, tri-o-tolylphosphine.

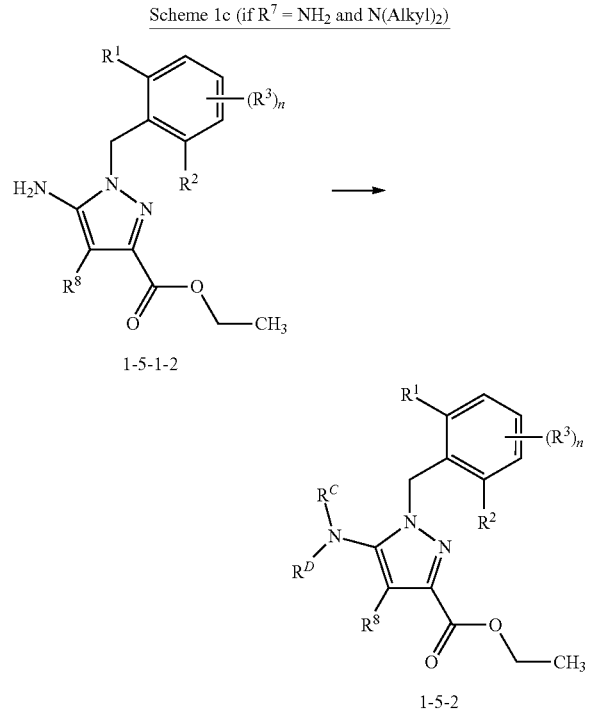

Scheme 1c. Route for the preparation of compounds of general formula (1-5-2), (wherein $R^1$, $R^2$, $R^3$, $R^8$ and n have the meaning as given for general formula (I), supra. $R^C$ and $R^D$ represent Alkyl-groups, especially 1-4C-alkyl whereby the alkyl residues may be same or different.

Intermediates (1-5-1-2) can be prepared following the procedure depicted in Bioorg Med Chem Lett, 2001, 11/6, 781-784.

Intermediates of general formula (1-5-1-2) can be converted to intermediates of general formula (1-5-2) by reaction with a suitable alkylating agent, such as, for example, iodomethane, in the presence of a suitable base, such as, for example, lithiumhydride, in a suitable solvent system, such as, for example, N,N-dimethylformamide, at a temperature between 0° C. and the boiling point of the respective solvent, preferably the reaction is carried out at room temperature.

Alternatively, intermediates of general formula (1-5-1-2) can be alkylated by reductive amination conditions to intermediates of general formula (1-5-2), such as, for example, formaldehyde, palladium on charcoal and hydrogen in a suitable solvent system, such as, for example, tetrahydrofuran, at a temperature between 0° C. and the boiling point of the respective solvent, preferably the reaction is carried out at room temperature.

Intermediates of general formulae (1-5-1-2) and (1-5-2) can be converted to compounds of the general formula (I) by the methods depicted in Schemes 1a and 2.

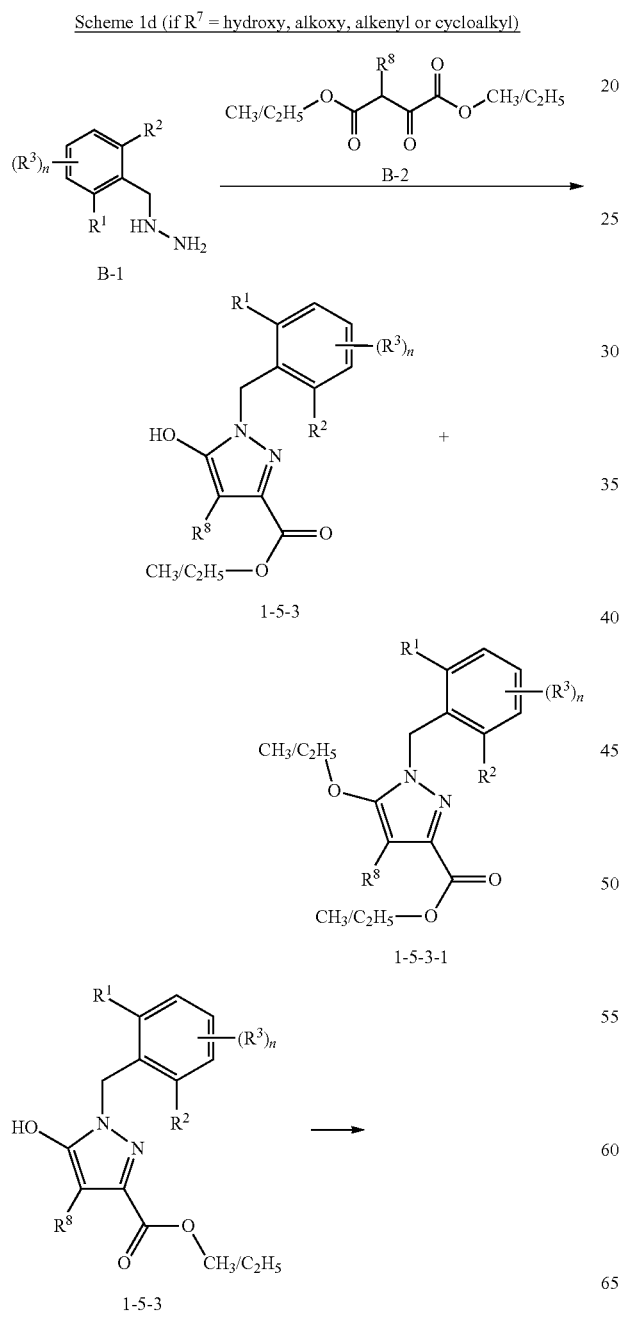

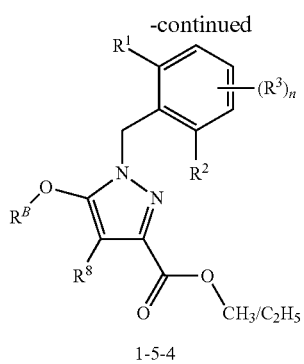

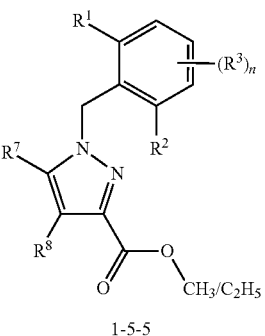

Scheme 1d. Route for the preparation of compounds of general formulae (1-5-3), (1-5-3-1), (1-5-4) and (1-5-5), wherein $R^1$, $R^2$, $R^3$, $R^8$ and n have the meaning as given for general formula (I), supra. $OR^B$ represents a leaving group, such as for example trifluoromethylsulfonate.

Compounds B-1 and B-2 are either commercially available or can be prepared according to procedures available from the public domain, as understandable to the person skilled in the art.

A suitably substituted Benzylhydrazine (B-1) can be reacted with a suitably substituted Oxalacetate (B-2) in a suitable solvent system, such as, for example, acetic acid and dioxane, at temperatures ranging from 0° C. to the boiling point of the respective solvent, preferably the reaction is carried out at 90° C., to furnish 1-benzyl-5-hydroxy-1H-pyrazole-3-carboxylate intermediates of general formula (1-5-3). As side products methyl or ethyl ethers (1-5-3-1) can be isolated.

Intermediates of general formula (1-5-3) can be converted to intermediates of general formula (1-5-4) by reaction with a suitable sulfonic acid derivative, such as, for example, triflic anhydride, in the presence of a suitable base, such as, for example, pyridine, in a suitable solvent system, such as, for example, dichloromethane, at a temperature between 0° C. and the boiling point of the respective solvent, preferably the reaction is carried out at room temperature.

Intermediates of general formula (1-5-4) can be converted to intermediates of general formula (1-5-5), wherein $R^7$ has the meaning of alkenyl or cycloalkyl, by reaction with boronic acids or boronic acid pinacole esters, such as, for example cyclopropylboronic acid, in the presence of a suitable base, such as, for example sodium carbonate, and a suitable palladium catalyst, such as for example tetrakis(triphenylphosphine)palladium(0), in a suitable solvent system, such as, for example, 1,2-dimethoxyethan, in a temperature range from room temperature to the boiling point of the respective solvent, preferably the reaction is carried out at 75° C.

Compounds, wherein $R^7$ has the meaning of alkoxy and haloalkoxy can be obtained from hydroxy-compounds of general formula (1-5-3) by conventional procedures, such as by reaction with a suitable alkylating agent, such as, for example, iodomethane, in the presence of a suitable base, such as, for example, potassium carbonate, in a suitable solvent system, such as, for example, acetone, at a temperature between 0° C. and the boiling point of the respective solvent, preferably the reaction is carried out at room temperature.

These compounds as well as Intermediates of general formulae (1-5-3), (1-5-4) and (1-5-5) can be converted to compounds of the general formula (I) by the methods depicted in schemes 1a and 2.

Scheme 1e (if $R^7$ = hydrogen, alkyl or cycloalkyl, and $R^8$ = halogen)

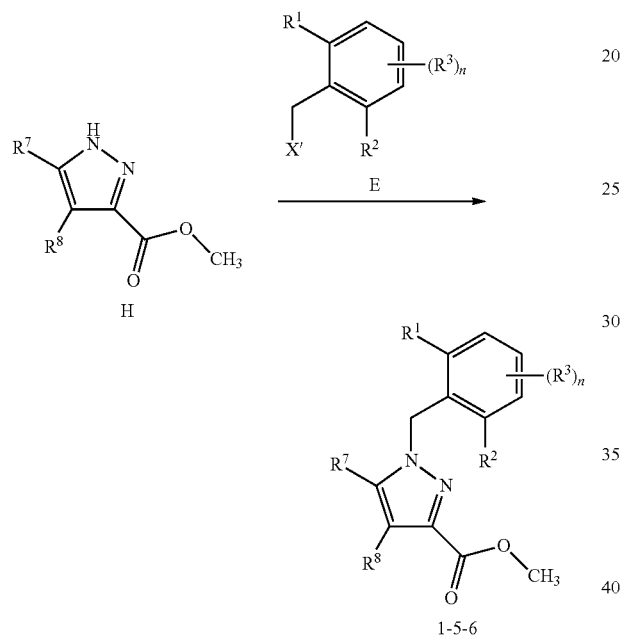

1-5-6

Scheme 1e. Route for the preparation of compounds of general formula (1-5-6), wherein $R^1$, $R^2$, $R^3$, and n have the meaning as given for general formula (I), supra. $R^7$ has the meaning of hydrogen, alkyl or cycloalkyl and $R^8$ has the meaning of fluoro, chloro or bromo.

Compounds E are either commercially available or can be prepared according to procedures available from the public domain, as understandable to the person skilled in the art. Specific examples are described in the subsequent paragraphs. X' represents a leaving group such as for example a Cl, Br or I, or X' stands for an aryl sulfonate such as for example p-toluene sulfonate, or for an alkyl sulfonate such as for example methane sulfonate or trifluoromethane sulfonate.

Compounds of formula H are commercially available or described in the literature (e.g. CAS-Reg.-No.: 1291177-21-3, 1281872-47-6, 1232838-31-1, 1005584-90-6, 681034-80-0).

Compounds of formula H can be converted to Intermediates of the general formula (1-5-6) by the method depicted in Scheme 1a.

Intermediates of general formula (1-5-6), can be converted to compounds of the general formula (I) by the methods depicted in Schemes 1a and 2.

Scheme 1f (if $R^8$ = $NO_2$, $NH_2$ or $N(Alkyl)_2$)

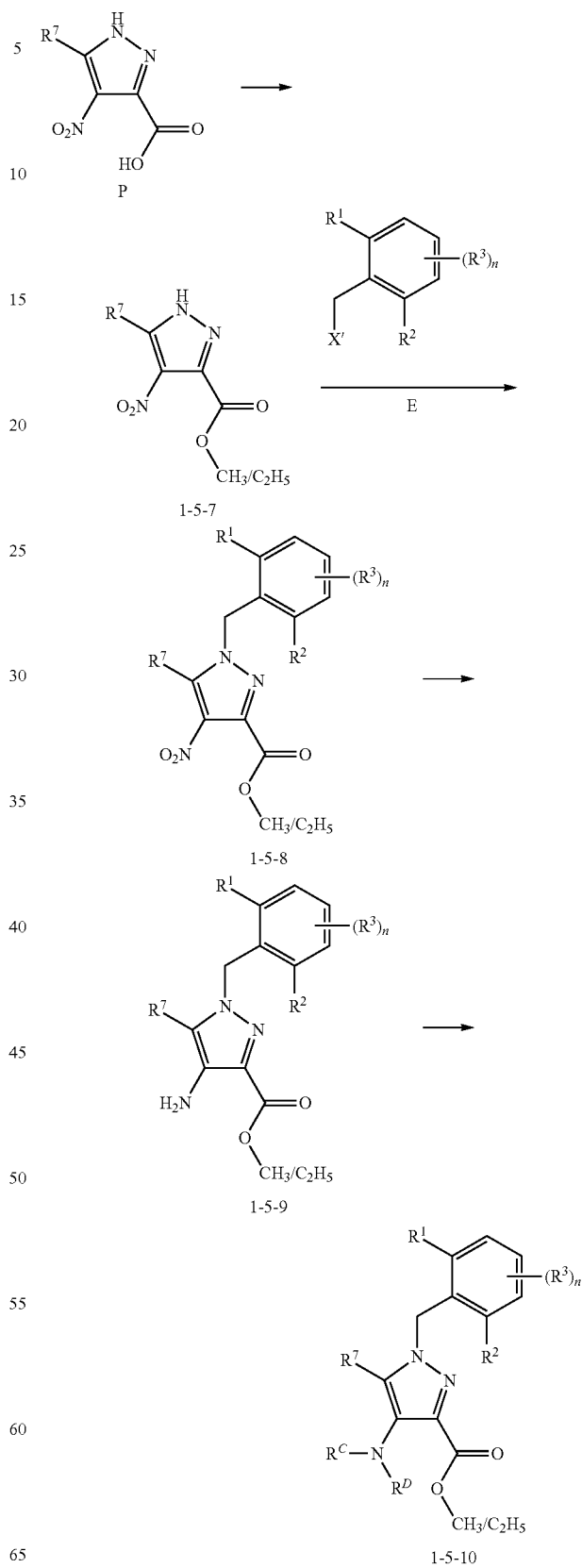

1-5-7

1-5-8

1-5-9

1-5-10

Scheme 1f. Route for the preparation of compounds of general formula (1-5-10), wherein $R^1$, $R^2$, $R^3$, $R^7$ and n have the meaning as given for general formula (I), supra. $R^C$ and $R^D$ represent Alkyl-groups, especially 1-4C-alkyl whereby the alkyl residues may be same or different.

Compounds P and E are either commercially available or can be prepared according to procedures available from the public domain, as understandable to the person skilled in the art. Specific examples are described in the subsequent paragraphs. X' represents a leaving group such as for example a Cl, Br or I, or X' stands for an aryl sulfonate such as for example p-toluene sulfonate, or for an alkyl sulfonate such as for example methane sulfonate or trifluoromethane sulfonate.

A suitably substituted pyrazole with a carboxylic acid function (P) can be esterificated with a suitably methylating or ethylation reagent, such as, for example (trimethylsilyl) diazomethane, in a suitable solvent system, such as, for example, tetrahydrofuran and methanol, at temperatures ranging from 0° C. to the boiling point of the respective solvent, preferably the reaction is carried out at 0° C., to furnish intermediates of general formula (1-5-7).

Intermediates of general formula (1-5-7) can be reacted with a suitably substituted benzyl halide or benzyl sulfonate of general formula (E), such as, for example, a benzyl bromide, in a suitable solvent system, such as, for example, tetrahydrofuran, in the presence of a suitable base, such as, for example, sodium hydride in a temperature range from room temperature to the boiling point of the respective solvent, preferably the reaction is carried out at room temperature, to furnish compounds of general formula (1-5-8).

Intermediates of general formula (1-5-8) can be converted to intermediates of general formula (1-5-9) by reaction with a suitable reduction agent, such as, for example, raney nickel and hydrazine hydrate, in a suitable solvent system, such as, for example, methanol, at a temperature between 0° C. and the boiling point of the respective solvent, preferably the reaction is carried out at room temperature.

Intermediates of general formula (1-5-9) can be converted to intermediates of general formula (1-5-10) by reaction with a suitable alkylating agent, such as, for example, iodomethane, in the presence of a suitable base, such as, for example, lithiumhydride, in a suitable solvent system, such as, for example, N,N-dimethylformamide, at a temperature between 0° C. and the boiling point of the respective solvent, preferably the reaction is carried out at room temperature.

Alternatively, intermediates of general formula (1-5-9) can be alkylated by reductive amination conditions to intermediates of general formula (1-5-10), such as, for example, formaldehyde, palladium on charcoal and hydrogen, in a suitable solvent system, such as, for example, tetrahydrofuran, at a temperature between 0° C. and the boiling point of the respective solvent, preferably the reaction is carried out at room temperature.

Intermediates of general formulae (1-5-10) can be converted to compounds of the general formula (I) by the methods depicted in Schemes 1a and 2.

Compounds of general formula (Ib) can be synthesised according to the procedure depicted in Scheme 2.

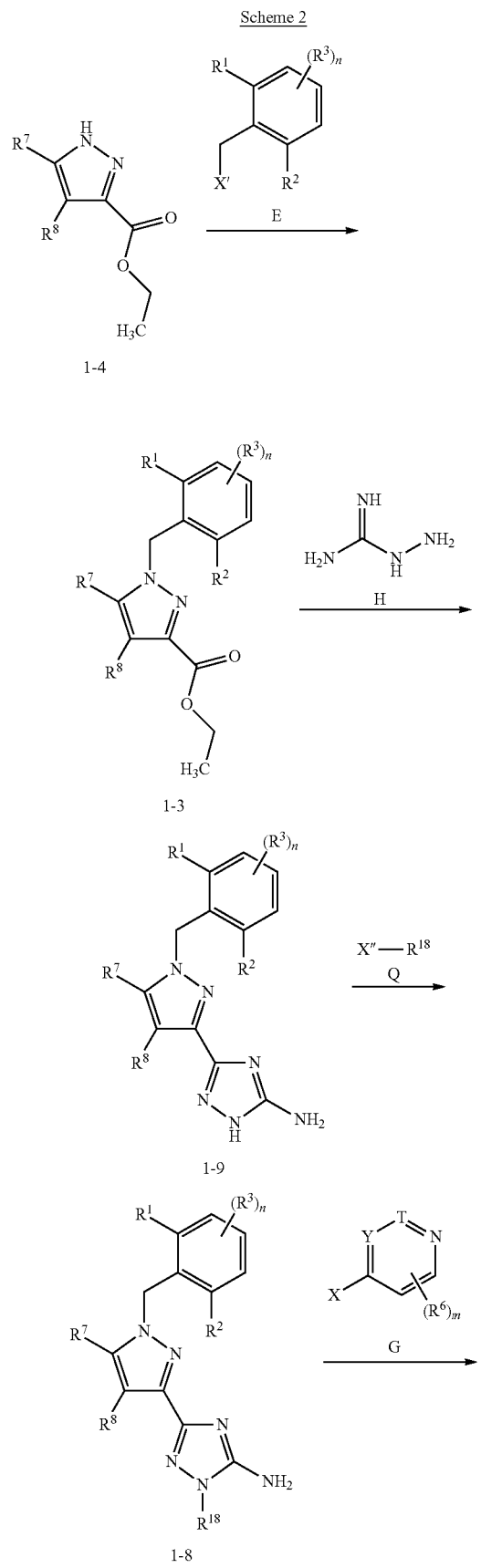

Scheme 2

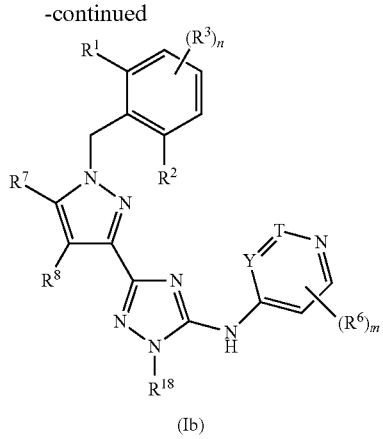

(Ib)

Scheme 2. Route for the preparation of compounds of general formula (Ib), wherein $R^1$, $R^2$, $R^3$, $R^6$, $R^7$, $R^8$, $R^{18}$, T, Y, T m and n have the meaning as given for general formula (I), supra. In addition, interconversion of any of the substituents, $R^1$, $R^2$, $R^3$, $R^6$, $R^7$, $R^8$ and $R^{18}$, can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Further specific examples are described in the subsequent paragraphs.

Compounds E, G, H, and Q are either commercially available or can be prepared according to procedures available from the public domain, as understandable to the person skilled in the art. Specific examples are described in the subsequent paragraphs. X represents F, Cl, Br, I, boronic acid or a boronic acid ester, such as for example 4,4,5,5-tetramethyl-2-phenyl-1,3,2-dioxaborolane (boronic acid pinacole ester). X' and X'' represent leaving groups such as for example a Cl, Br or I, or X' and X'' stand for an aryl sulfonate such as for example p-toluene sulfonate, or for an alkyl sulfonate such as for example methane sulfonate or trifluoromethane sulfonate.

Intermediates of general formula (1-4) can be reacted with a suitably substituted benzyl halide or benzyl sulfonate of general formula (E), such as, for example, a benzyl bromide, in a suitable solvent system, such as, for example, tetrahydrofuran, in the presence of a suitable base, such as, for example, sodium hydride in a temperature range from 0° C. to the boiling point of the respective solvent, preferably the reaction is carried out at room temperature, to furnish compounds of general formula (1-3).

Intermediates of general formula (1-3) can be reacted with aminoguanidine in a suitable solvent system, such as, for example, methanol, in a temperature range from room temperature to the boiling point of the respective solvent, to furnish compounds of general formula (1-9).

Intermediates of general formula (1-9) can be reacted with a suitable alkylating agent of general formula (Q), such as, for example, 2-bromoethyl methyl ether, in the presence of a suitable base, such as, for example, potassium carbonate, in a suitable solvent system, such as, for example, N,N-dimethylformamide, at a temperature between 0° C. and the boiling point of the respective solvent, preferably the reaction is carried out at 60° C. to furnish compounds of general formula (1-8).

Intermediates of general formula (1-8) can be reacted with a suitable halogen-substituted heteroaryl compounds of the general formula (G), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis-(diphenyl-phosphane), in a suitable solvent system, such as, for example, N,N-dimethylformamide, in a temperature range from room temperature to the boiling point of the respective solvent, preferably the reaction is carried out at 105° C. to furnish compounds of general formula (Ib). Alternatively the following palladium catalysts can be used:

allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands:

racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethyl-phosphonium tetrafluoroborate, 2-(di-tert-butylphosphino) biphenyl, tri-tert-butyl-phosphonium tetrafluoroborate, tri-2-furylphosphine, tris(2,4-di-tert-butylphenyl)-phosphite, tri-o-tolylphosphine.

Compounds of general formula (Ic) can be synthesised according to the procedure depicted in Scheme 3.

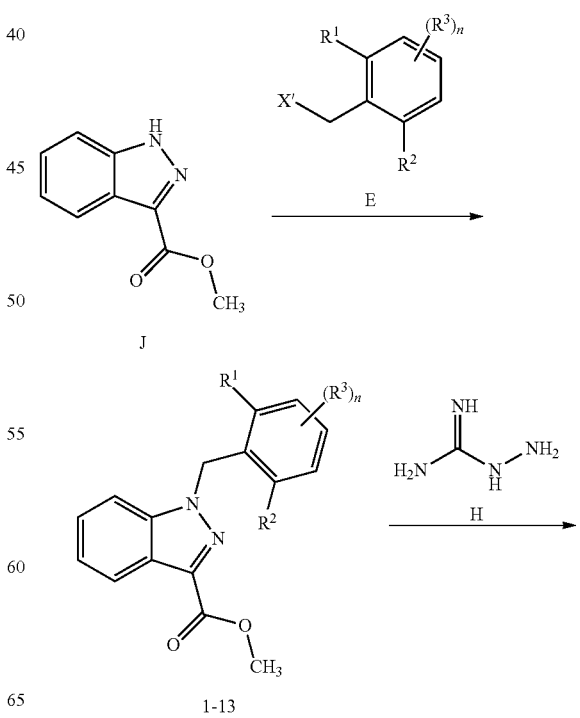

Scheme 3

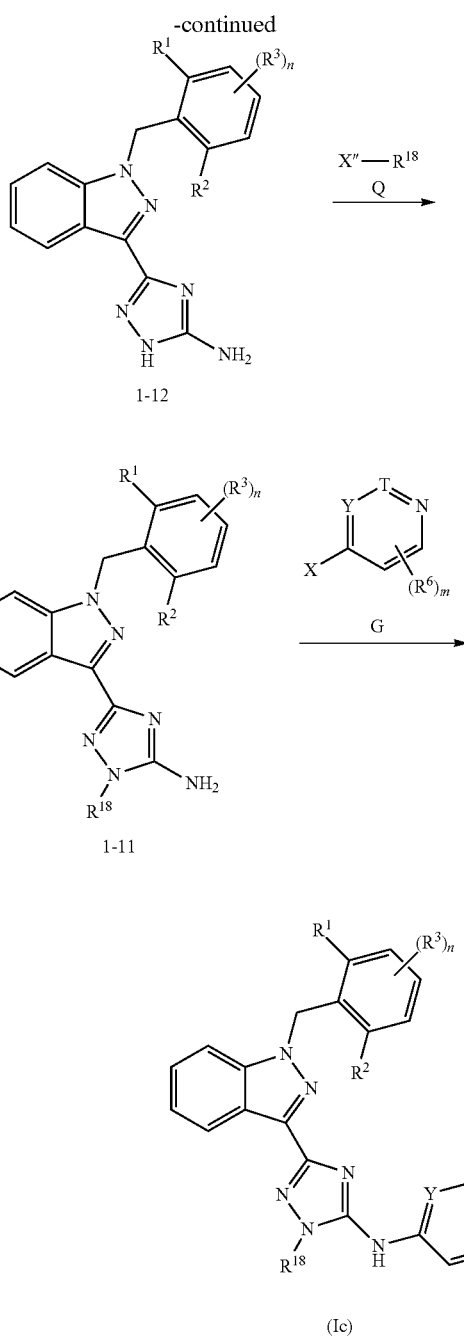

well-known to the person skilled in the art (see for example T. W. Greene and P. G. M. Wuts in Protective Groups in Organic Synthesis, 3rd edition, Wiley 1999). Further specific examples are described in the subsequent paragraphs.

Compounds E, Q and G are either commercially available or can be prepared according to procedures available from the public domain, as understandable to the person skilled in the art. Specific examples are described in the subsequent paragraphs. X represents F, Cl, Br, I, boronic acid or a boronic acid ester, such as for example 4,4,5,5-tetramethyl-2-phenyl-1,3,2-dioxaborolane (boronic acid pinacole ester). X' and X" represent leaving groups such as for example a Cl, Br or I, or X' and X" stand for an aryl sulfonate such as for example p-toluene sulfonate, or for an alkyl sulfonate such as for example methane sulfonate or trifluoromethane sulfonate.

Compound J (CAS Registry Number: 43120-28-1) can be reacted with a suitably substituted benzyl halide or benzyl sulfonate of general formula (E), such as, for example, a benzyl bromide, in a suitable solvent system, such as, for example, tetrahydrofuran, in the presence of a suitable base, such as, for example, sodium hydride in a temperature range from 0° C. to the boiling point of the respective solvent, preferably the reaction is carried out at room temperature, to furnish compounds of general formula (1-13).

Intermediates of general formula (1-13) can be reacted with compound H, aminoguanidine, in a suitable solvent system, such as, for example, methanol, in a temperature range from room temperature to the boiling point of the respective solvent, to furnish compounds of general formula (1-12).

Intermediates of general formula (1-12) can be reacted with a suitable alkylating agent of general formula (Q), such as, for example, 2-bromoethyl methyl ether, in the presence of a suitable base, such as, for example, potassium carbonate, in a suitable solvent system, such as, for example, N,N-dimethylformamide, at a temperature between 0° C. and the boiling point of the respective solvent, preferably the reaction is carried out at 60° C. to furnish compounds of general formula (1-11).

Intermediates of general formula (1-11) can be reacted with a suitable halogen-substituted heteroaryl compounds of the general formula (G), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis-(diphenylphosphane), in a suitable solvent system, such as, for example, N,N-dimethylformamide, in a temperature range from room temperature to the boiling point of the respective solvent, preferably the reaction is carried out at 105° C. to furnish compounds of general formula (Ic). Alternatively the following palladium catalysts can be used: allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands: racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethyl-phosphonium tetrafluoroborate, 2-(di-tert-butylphosphino)

Scheme 3. Route for the preparation of compounds of general formula (I), wherein $R^1$, $R^2$, $R^3$, $R^6$, $R^{18}$, T, Y, T m and n have the meaning as given for general formula (I), supra. In addition, interconversion of any of the substituents, $R^1$, $R^2$, $R^3$, $R^6$ and $R^{18}$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are biphenyl, tri-tert-butyl-phosphonium tetrafluoroborate, tri-2-furylphosphine, tris(2,4-di-tert-butylphenyl)-phosphite, tri-o-tolylphosphine.

Compounds of general formula (Id) can be synthesised from compounds of general formula E and K, according to the procedure depicted in Scheme 4.

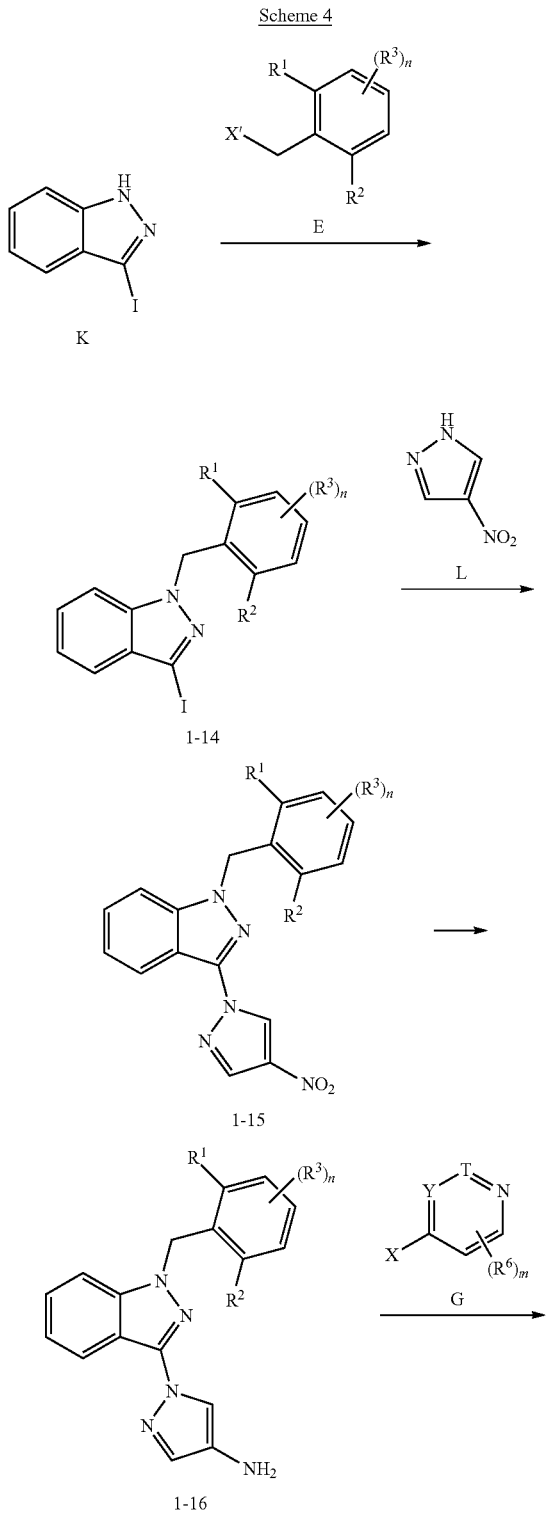

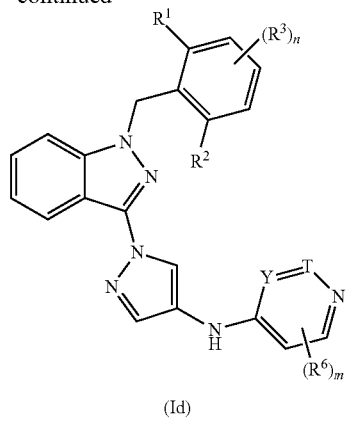

Scheme 4. Route for the preparation of compounds of general formula (I), wherein $R^1$, $R^2$, $R^3$, $R^6$, T, Y, m and n have the meaning as given for general formula (I), supra. In addition, interconversion of any of the substituents, $R^1$, $R^2$, $R^3$, $R^4$, $R^6$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Further specific examples are described in the subsequent paragraphs.

Compounds E and G are either commercially available or can be prepared according to procedures available from the public domain, as understandable to the person skilled in the art. Specific examples are described in the subsequent paragraphs. X represents F, Cl, Br, I, boronic acid or a boronic acid ester, such as for example 4,4,5,5-tetramethyl-2-phenyl-1,3,2-dioxaborolane (boronic acid pinacole ester). X' represents a leaving group such as for example a Cl, Br or I, or X' stands for an aryl sulfonate such as for example p-toluene sulfonate, or for an alkyl sulfonate such as for example methane sulfonate or trifluoromethane sulfonate.

Compound K (CAS Registry Number: 66607-27-0) can be reacted with a suitably substituted benzyl halide or benzyl sulfonate of general formula (E), such as, for example, a benzyl bromide, in a suitable solvent system, such as, for example, tetrahydrofuran, in the presence of a suitable base, such as, for example, cesium carbonate, in a temperature range from 0° C. to the boiling point of the respective solvent, preferably the reaction is carried out at room temperature, to furnish compounds of general formula (1-14).

Intermediates of general formula (1-14) can be reacted with compound L, 4-nitro-1H-pyrazole (CAS Registry Number: 2075-46-9), in a suitable solvent system, such as, for example, N,N-dimethylformamide, in the presence of a suitable base, such as, for example, cesium carbonate, and in the presence of copper (II) oxide and iron (III) acetyl acetonate, in a temperature range from room temperature to the boiling point of the respective solvent, preferably the reaction is carried out at 90° C., to furnish compounds of general formula (1-15).

Intermediates of general formula (1-15) can be reduced to the corresponding amino compounds, for example by reaction with raney nickel and hydrazine, in a suitable solvent system, such as, for example, methanol, in a temperature range from room temperature to the boiling point of the respective solvent, preferably the reaction is carried out at room temperature, to furnish compounds of general formula (1-16).

Intermediates of general formula (1-16) can be reacted with a suitable halogen-substituted heteroaryl compounds of the general formula (G), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis-(diphenylphosphane), in a suitable solvent system, such as, for example, N,N-dimethylformamide, in a temperature range from room temperature to the boiling point of the respective solvent, preferably the reaction is carried out at 105° C. to furnish compounds of general formula (Id). Alternatively the following palladium catalysts can be used:

allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands:

racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethyl-phosphonium tetrafluoroborate, 2-(di-tert-butylphosphino)biphenyl, tri-tert-butyl-phosphonium tetrafluoroborate, tri-2-furylphosphine, tris(2,4-di-tert-butylphenyl)-phosphite, tri-o-tolylphosphine.

Compounds of general formula (Ie) can be synthesised according to the procedure depicted in Scheme 5.

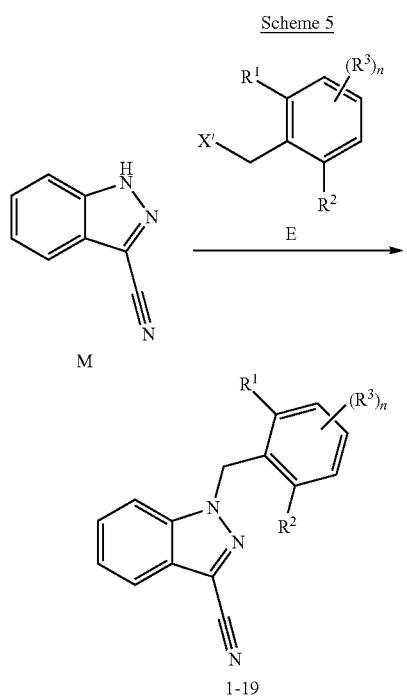

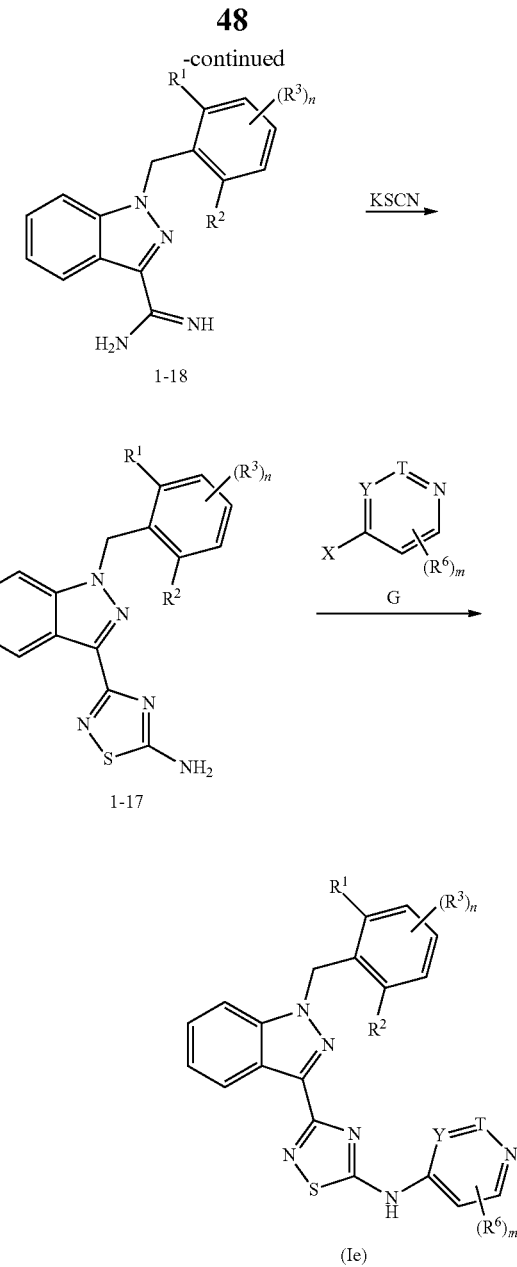

Scheme 5. Route for the preparation of compounds of general formula (I), wherein $R^1$, $R^2$, $R^3$, $R^6$ T, Y, m and n have the meaning as given for general formula (I), supra. In addition, interconversion of any of the substituents, $R^1$, $R^2$, $R^3$, $R^6$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Further specific examples are described in the subsequent paragraphs.

Compounds E and G are either commercially available or can be prepared according to procedures available from the public domain, as understandable to the person skilled in the art. Specific examples are described in the subsequent paragraphs. X represents F, Cl, Br, I, boronic acid or a boronic acid ester, such as for example 4,4,5,5-tetramethyl-2-phenyl-1,3,2-dioxaborolane (boronic acid pinacole ester). X' represents a leaving group such as for example a Cl, Br or I, or X' stands for an aryl sulfonate such as for example p-toluene sulfonate, or for an alkyl sulfonate such as for example methane sulfonate or trifluoromethane sulfonate.

Compound M (CAS Registry Number: 50264-88-5) can be reacted with a suitably substituted benzyl halide or benzyl sulfonate of general formula (E), such as, for example, a benzyl bromide, in a suitable solvent system, such as, for example, tetrahydrofuran, in the presence of a suitable base, such as, for example, cesium carbonate, in a temperature range from 0° C. to the boiling point of the respective solvent, preferably the reaction is carried out at room temperature, to furnish compounds of general formula (1-19).

Intermediates of general formula (1-19) can be converted to intermediates of general formula (1-18) by reaction with a suitable alcoholate, such as, for example sodium methanolate, in a suitable solvent system, such as, for example, the corresponding alcohol, e.g. methanol, at a temperature between room temperature and the boiling point of the respective solvent, preferably the reaction is carried out at room temperature, and subsequent treatment with a suitable source of ammonium, such as for example, ammonium chloride in the presence of a suitable acid, such as for example acetic acid in a temperature range from room temperature to the boiling point of the respective solvent, preferably the reaction is carried out at 50° C.

Intermediates of general formula (1-18) can be reacted with potassium thiocyanate in a suitable solvent system, such as, for example, methanol, in a temperature range from 0° C. to 50° C., preferably the reaction is carried out in a temperature range from 0° C. to room temperature, to furnish compounds of general formula (1-17).

Intermediates of general formula (1-17) can be reacted with a suitable halogen-substituted heteroaryl compounds of the general formula (G), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis-(diphenylphosphane), in a suitable solvent system, such as, for example, N,N-dimethylformamide, in a temperature range from room temperature to the boiling point of the respective solvent, preferably the reaction is carried out at 105° C. to furnish compounds of general formula (Ie). Alternatively the following palladium catalysts can be used: allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands: racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethyl-phosphonium tetrafluoroborate, 2-(di-tert-butylphosphino) biphenyl, tri-tert-butyl-phosphonium tetrafluoroborate, tri-2-furylphosphine, tris(2,4-di-tert-butylphenyl)-phosphite, tri-o-tolylphosphine.

Compounds of general formula (Ia-1) can be converted into compounds of general formulae (If), (Ig) and (Ih) according to the procedure depicted in Scheme 6.

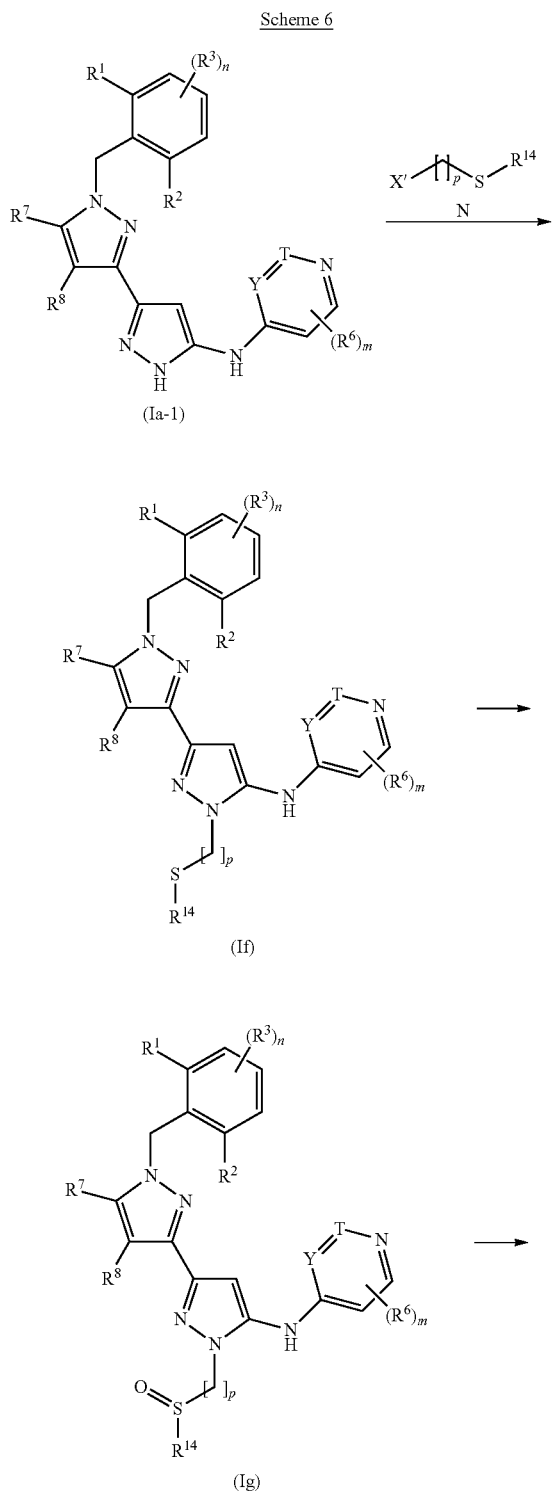

Scheme 6

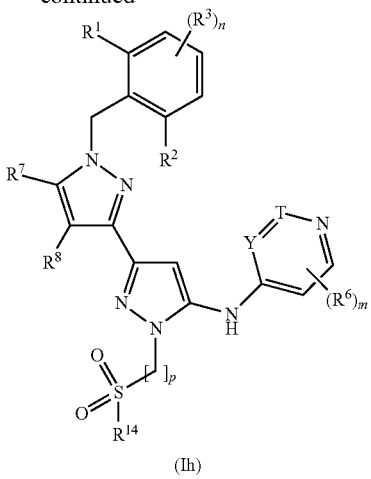

(Ih)

Scheme 6. Process for the preparation of compounds of general formulae (If), (Ig) and (Ih), wherein $R^1$, $R^2$, $R^3$, $R^6$, $R^7$, $R^8$, $R^{14}$, T, Y, m and n have the meaning as given for general formula (I), supra. p represents an integer from 1 to 6. In addition, interconversion of any of the substituents, $R^1$, $R^2$, $R^3$, $R^7$ and $R^8$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Compounds of general formula (N) are either commercially available or can be prepared according to procedures available from the public domain, as understandable to the person skilled in the art. X' represents F, Cl, Br, I or a sulfonate, e.g. trifluoromethylsulfonate or p-toluolsulfonate.

Compounds of general formula (Ia-1) can be reacted with a suitable halo-alkyl-alkyl-sulfide of the general formula (N), such as, for example 3-chloropropyl methyl sulfide, in the presence of a suitable base, such as, for example potassium carbonate, in a suitable solvent system, such as, for example, N,N-dimethylformamide, in a temperature range from room temperature to the boiling point of the respective solvent, preferably the reaction is carried out at 60° C. to furnish compounds of general formula (If).

Compounds of general formula (If) are converted to compounds of general formula (Ig) by treatment with a suitable oxidation agent, such as for example meta-chloroperbenzoic acid, in a suitable solvent, such as, for example, chloroform, in a temperature range from 0° C. to the boiling point of the respective solvent, preferably the reaction is carried out at 0° C.

Compounds of general formula (Ig) can be converted into compounds of general formula (Ih) by treatment with a suitable oxidation agent, such as for example hydrogen peroxide and the reagent diethyl azodicarboxylate, in a suitable solvent, such as, for example, tetrahydrofuran, in a temperature range from 0° C. to the boiling point of the respective solvent, preferably the reaction is carried out at 50° C.

Compounds of general formula (Ib-1) can be converted into compounds of general formulae (Ij), (Ik) and (Im) according to the procedure depicted in Scheme 7.

Scheme 7

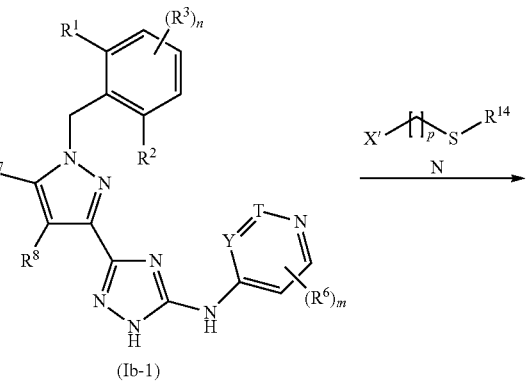

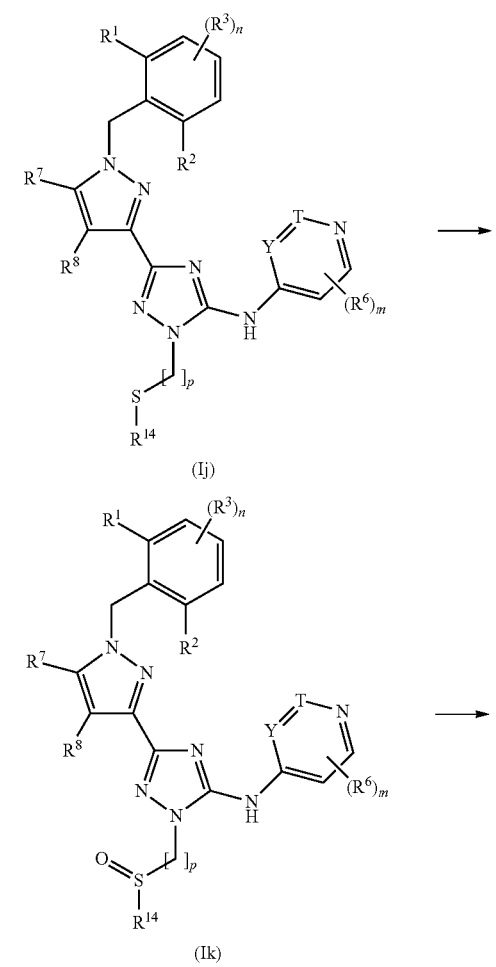

-continued

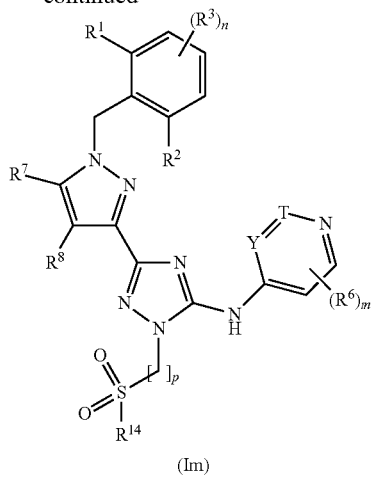

(Im)

Scheme 7. Process for the preparation of compounds of general formulae (Ij), (Ik) and (Im), wherein $R^1$, $R^2$, $R^3$, $R^6$, $R^7$, $R^8$, $R^{14}$, T, Y, m and n have the meaning as given for general formula (I), supra. p represents an integer from 1 to 6. X' represents F, Cl, Br, I or a sulfonate, e.g. trifluoromethylsulfonate or p-toluolsulfonate.

Compounds of general formula (Ib-1) can be transformed to compounds of the general formula (Ij) in analogy to the method described in Scheme 6. Compounds of general formula (Ij) can be transformed to compounds of the general formula (Ik) in analogy to the method described in Scheme 6. Compounds of general formula (Ik) can be transformed to compounds of the general formula (Im) in analogy to the method described in Scheme 6.

Compounds of general formulae (In) and (Io) can be synthesized from compounds of general formula (Ig) according to the procedure depicted in Scheme 8.

Scheme 8

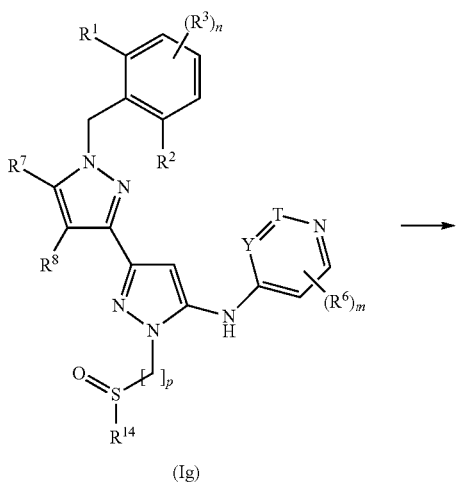

(Ig)

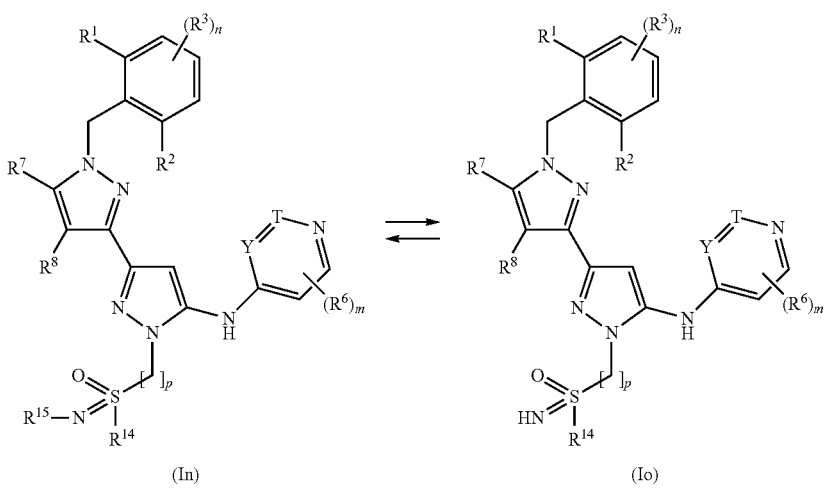

(In)    (Io)

Scheme 8 Route for the preparation of compounds of general formulae (In), and (Io), wherein $R^1$, $R^2$, $R^3$, $R^6$, $R^7$, $R^8$, $R^9$, $R^{14}$, $R^{15}$, T, Y, m and n have the meaning as given for general formula (I), supra, and p is an integer from 1 to 6. In addition, interconversion of any of the substituents, $R^1$, $R^2$, $R^3$, $R^6$, $R^7$, $R^8$, $R^9$, and $R^{15}$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Intermediates of general formula (Ig) can be reacted to the protected sulfoximine with a suitable reagent mixture, such as, for example 2,2,2-trifluoro acetamide, iodo-benzene diacetate and magnesium oxide, with a suitable catalyst, such as, for example, rhodium(II) acetate dimer, in a suitable solvent system, such as, for example, dichloromethane, in a temperature range from 0° C. to the boiling point of the respective solvent, preferably the reaction is carried out at room temperature to furnish the protected compounds. Deprotection can be accomplished under suitable conditions, such as, for example in the case of trifluoroacetate, a suitable base, such as, for example, potassium carbonate, in a suitable solvent system, such as, for example, methanol, in a temperature range from 0° C. to the boiling point of the respective solvent, preferably the reaction is carried out at room temperature to furnish the compounds of general formula (Io). The sulfoximines of general formula (Io) can be N-functionalized by several methods to furnish sulfoximines of general formula (In).

For the preparation of N-functionalized sulfoximines multiple methods are known:

Alkylation: see for example: a) U. Lücking et al, US 2007/0232632; b) C. R. Johnson, J. Org. Chem. 1993, 58, 1922; c) C. Bolm et al, Synthesis 2009, 10, 1601.

Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.

Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C. Bolm et al, J. Org. Chem. 2005, 70, 2346; e) U. Lücking et al, WO2007/71455.

Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.

Reaction with sulfonylchlorides: see for example: a) D. J. Cram et al, J. Am. Chem. Soc. 1970, 92, 7369; b) C. R. Johnson et al, J. Org. Chem. 1978, 43, 4136; c) A. C. Barnes, J. Med. Chem. 1979, 22, 418; d) D. Craig et al, Tet. 1995, 51, 6071; e) U. Lücking et al, US2007/191393.

Reaction with chloroformates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800.

Compounds of general formulae (Ip) and (Iq) can be synthesized from compounds of general formula (Ig) according to the procedure depicted in Scheme 9.

Scheme 9

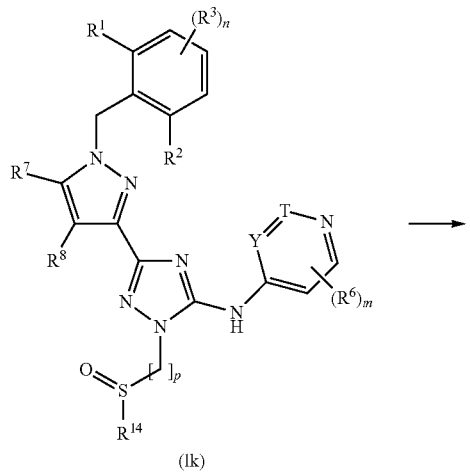

(Ik)

-continued

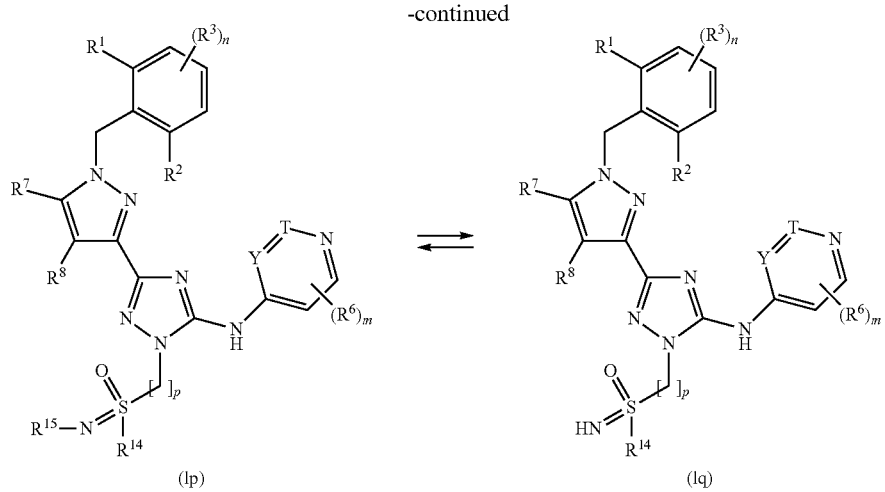

(Ip)                                      (Iq)

Scheme 9. Route for the preparation of compounds of general formulae (Ip), and (Iq), wherein $R^1$, $R^2$, $R^3$, $R^6$, $R^7$, $R^8$, $R^9$, $R^{14}$, $R^{15}$, T, Y, T m and n have the meaning as given for general formula (I), supra, and p is an integer from 1 to 6.

Compounds of general formula (Ik) can be transformed to compounds of the general formulae (Ip) and (Iq) in analogy to the method described in Scheme 8. The sulfoximines of general formula (Iq) can be N-functionalized by several methods to furnish sulfoximines of general formula (In).

For the preparation of N-functionalized sulfoximines multiple methods are known:

Alkylation: see for example: a) U. Lücking et al, US 2007/0232632; b) C. R. Johnson, J. Org. Chem. 1993, 58, 1922; c) C. Bolm et al, Synthesis 2009, 10, 1601.

Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.

Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C. Bolm et al, J. Org. Chem. 2005, 70, 2346; e) U. Lücking et al, WO2007/71455.

Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.

Reaction with sulfonylchlorides: see for example: a) D. J. Cram et al, J. Am. Chem. Soc. 1970, 92, 7369; b) C. R. Johnson et al, J. Org. Chem. 1978, 43, 4136; c) A. C. Barnes, J. Med. Chem. 1979, 22, 418; d) D. Craig et al, Tet. 1995, 51, 6071; e) U. Lücking et al, US2007/191393.

Reaction with chloroformates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800.

Intermediates of general formula (1-33) can be synthesized from compounds of general formula (Ir) which are compounds of formula (I) wherein $R^3$=methoxy or ethoxy, via debenzylation according to the procedure depicted in Scheme 10.

Scheme 10

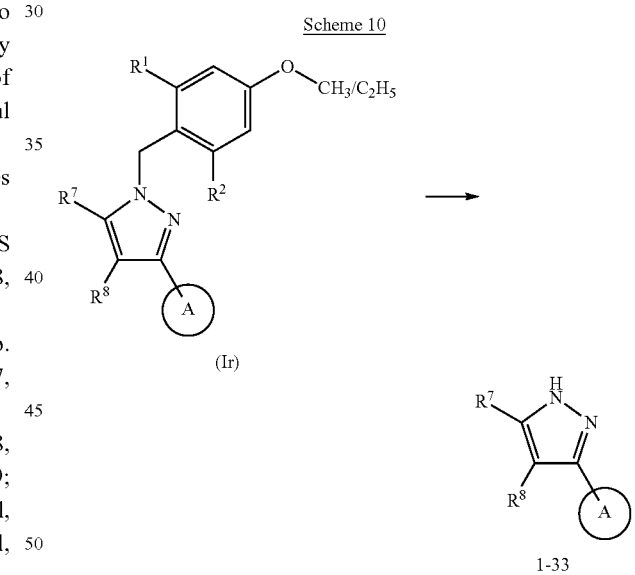

Scheme 10. Route for the preparation of compounds of general formula (1-33), wherein the group A and the substituents $R^1$, $R^2$, $R^7$ and $R^8$ have the meaning as given for general formula (I), supra.

Compounds of general formula (Ir) are converted to intermediates of general formula (1-33) by treatment with a suitable acid system, such as, for example a mixture of trifluoroacetic acid and trifluoromethanesulfonic acid, in a suitable solvent, such as, for example, dichloroethan, in a temperature range from room temperature to the boiling point of the respective solvent, preferably the reaction is carried out at room temperature.

Compounds of general formulae (Is), (It), (Iu) can be synthesized from compounds of general formulae (1-31) and (1-33) according to the procedure depicted in Scheme 11.

Scheme 11

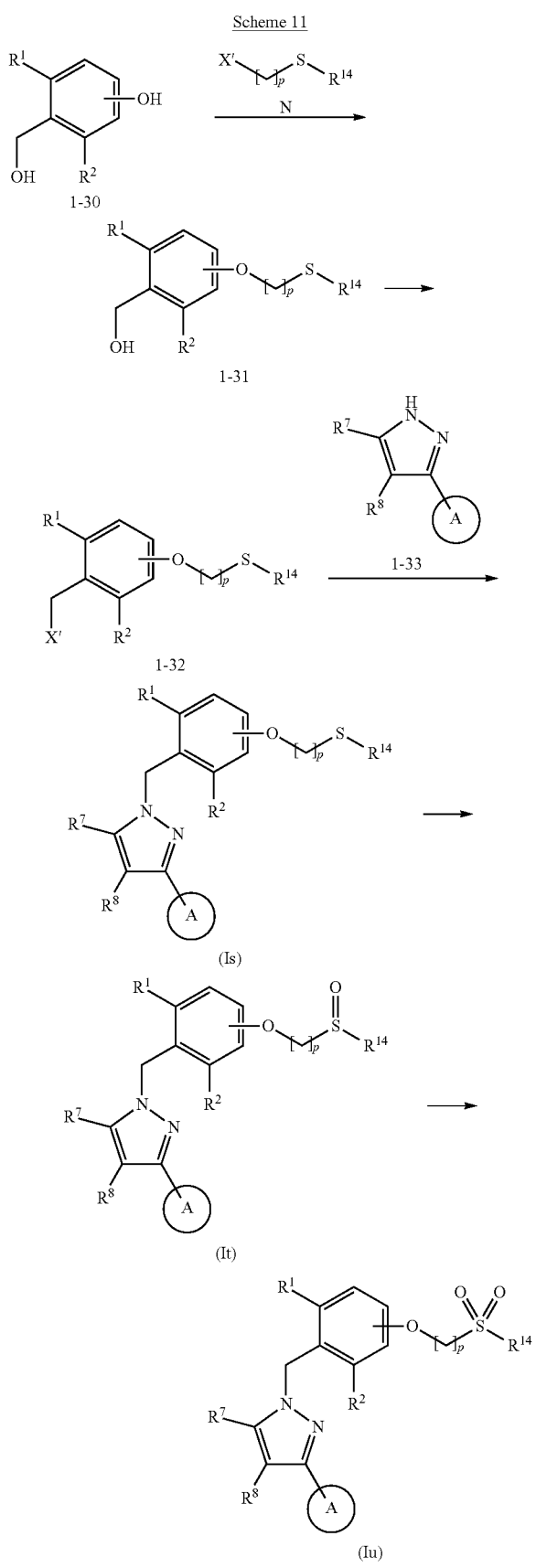

Scheme 11. Route for the preparation of compounds of general formulae (Is), (It) and (Iu), wherein the group A and the substituents $R^1$, $R^2$, $R^7$, $R^8$, $R^{14}$, $R^{15}$ and m have the meaning as given for general formula (I), supra, and p represents an integer from 1 to 6. In addition, interconversion of any of the group A and the substituents $R^1$, $R^2$, $R^7$, $R^8$ and $R^{15}$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Compounds of general formula (N) are either commercially available or can be prepared according to procedures available from the public domain, as understandable to the person skilled in the art. X' represents F, Cl, Br, I or a sulfonate, e.g. trifluoromethylsulfonate or p-toluolsulfonate.

Intermediates of general formula (1-30) can be reacted with a suitable halo-alkyl-alkyl-sulfide of the general formula (N), such as, for example 3-chloropropyl methyl sulfide, in the presence of a suitable base, such as, for example potassium carbonate, in a suitable solvent system, such as, for example, N,N-dimethylformamide, in a temperature range from room temperature to the boiling point of the respective solvent, preferably the reaction is carried out at 60° C. to furnish compounds of general formula (1-31).

Intermediates of general formula (1-31) can be transformed into intermediates of the general formula (1-32), where X' represents a leaving group, by reaction for example with a suitable halogenation reagent, such as, for example, hydrogen bromide, in a suitable solvent system, such as, for example, diethylether, in a temperature range from room temperature to the boiling point of the respective solvent, preferably the reaction is carried out at room temperature to furnish the intermediate of general formula (1-32).

Intermediates of general formula (1-33) can be reacted with a suitably substituted benzyl halide or benzyl sulfonate of general formula (1-32), such as, for example, a benzyl bromide, in a suitable solvent system, such as, for example, tetrahydrofuran, in the presence of a suitable base, such as, for example, sodium hydride in a temperature range from room temperature to the boiling point of the respective solvent, preferably the reaction is carried out at room temperature, to furnish compounds of general formula (Is).

Compounds of general formula (Is) can be oxidized with a suitable oxidation agent, such as, for example meta-chloroperbenzoic acid, in a suitable solvent system, such as, for example, chloroform, in a temperature range from 0° C. to the boiling point of the respective solvent, preferably the reaction is carried out at 0° C. to furnish compounds of general formula (It).

Compounds of general formula (It) can be converted into compounds of general formula (Iu) by treatment with a suitable oxidation agent, such as for example hydrogen peroxide and the reagent diethyl azodicarboxylate, in a suitable solvent, such as, for example, tetrahydrofuran, in a temperature range from 0° C. to the boiling point of the respective solvent, preferably the reaction is carried out at 50° C.

Compounds of general formulae (Iv) and (Iw) can be synthesized from compounds of general formulae (It) according to the procedure depicted in Scheme 12.

Scheme 12

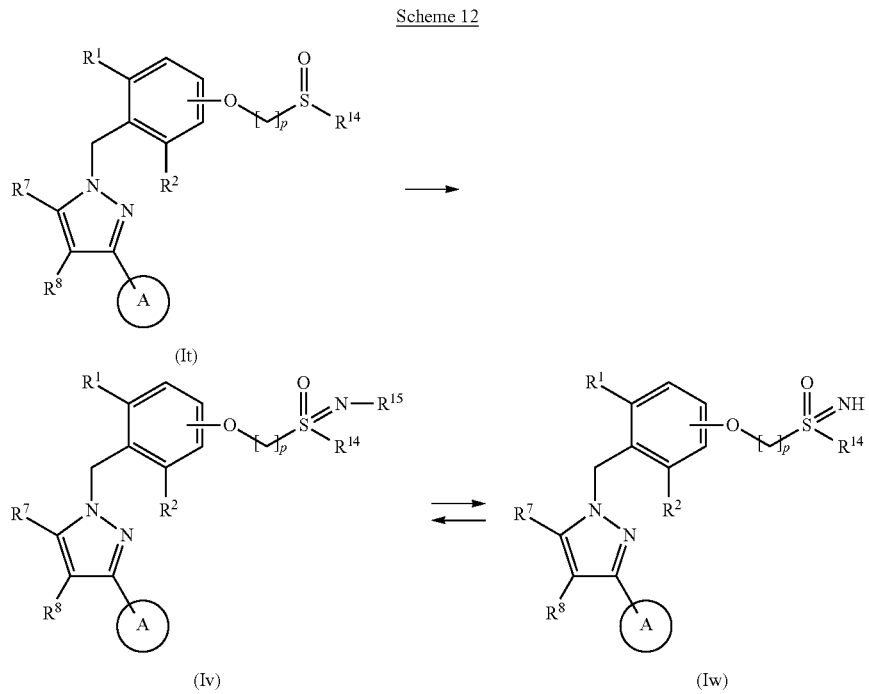

Scheme 12. Route for the preparation of compounds of general formulae (Iv) and (Iw), wherein the group A and the substituents $R^1$, $R^2$, $R^7$, $R^8$, $R^{14}$, $R^{15}$ and m have the meaning as given for general formula (I), supra, and p represents an integer from 1 to 6. In addition, interconversion of any of the group A and the substituents $R^1$, $R^2$, $R^7$, $R^8$ and $R^{15}$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Compounds of general formula (It) can be reacted to the protected sulfoximine with a suitable reagent mixture, such as, for example 2,2,2-trifluoro acetamide, iodo-benzene diacetate and magnesium oxide, with a suitable catalyst, such as, for example, rhodium(II) acetate dimer, in a suitable solvent system, such as, for example, dichloromethane, in a temperature range from 0° C. to the boiling point of the respective solvent, preferably the reaction is carried out at room temperature to furnish the protected compounds. Deprotection can be accomplished under suitable conditions, such as, for example in the case of trifluoroacetate, a suitable base, such as, for example, potassium carbonate, in a suitable solvent system, such as, for example, methanol, in a temperature range from 0° C. to the boiling point of the respective solvent, preferably the reaction is carried out at room temperature of furnish the compounds of general formula (Iw). The sulfoximines of general formula (Iw) can be N-functionalized by several methods to furnish sulfoximines of general formula (Iv).

For the preparation of N-functionalized sulfoximines multiple methods are known:

Alkylation: see for example: a) U. Lücking et al, US 2007/0232632; b) C. R. Johnson, J. Org. Chem. 1993, 58, 1922; c) C. Bolm et al, Synthesis 2009, 10, 1601.

Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.

Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C. Bolm et al, J. Org. Chem. 2005, 70, 2346; e) U. Lücking et al, WO2007/71455.

Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.

Reaction with sulfonylchlorides: see for example: a) D. J. Cram et al, J. Am. Chem. Soc. 1970, 92, 7369; b) C. R. Johnson et al, J. Org. Chem. 1978, 43, 4136; c) A. C. Barnes, J. Med. Chem. 1979, 22, 418; d) D. Craig et al, Tet. 1995, 51, 6071; e) U. Lücking et al, US2007/191393.

Reaction with chloroformates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800.

One preferred aspect of the invention is the process for the preparation of the compounds of claims 1-5 according to the Examples.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the examples section.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1 to 5 according to the examples.

Optionally, compounds of the formula (I) can be converted into their salts, or, optionally, salts of the compounds of the formula (I) can be converted into the free compounds. Corresponding processes are customary for the skilled person.

Optionally, compounds of the formula (I) can be converted into their N-oxides. The N-oxide may also be introduced by way of an intermediate. N-oxides may be prepared by treating an appropriate precursor with an oxidizing agent, such as meta-chloroperbenzoic acid, in an appropriate solvent, such as dichloromethane, at suitable temperatures, such as from 0° C. to 40° C., whereby room temperature is generally preferred. Further corresponding processes for forming N-oxides are customary for the skilled person.

Commercial Utility

As mentioned supra, the compounds of the present invention have surprisingly been found to effectively inhibit Bub1 finally resulting in apoptosis and cell death and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, anum, endocrine glands (e.g. thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumors in said organs and corresponding secondary tumors in distant organs ("tumor metastases"). Haematological tumors can e.g be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

One aspect of the invention is the use of the compounds according to formula (I) for the treatment of cervical cancer, breast cancer, ovarian cancer, non-small cell lung cancer (NSCLC), prostate cancer, colon cancer, pancreas cancer, osteo sacroma, acute myelogenous leucemia, Burkitt lymphoma, multiple myeloma, melanoma.

One aspect of the invention is the use of the compounds according to formula (I) for the treatment of cervical cancer, non-small cell lung cancer (NSCLC), prostate cancer, colon cancer, melanoma, particularly cervical cancer.

Another aspect of the invention is the use of the compounds according to formula (I) for the treatment of cervical cancer, NSCLC, prostate cancer, colon cancer and melanoma, particularly cervical cancer as well as a method of treatment of cervical cancer, NSCLC, prostate cancer, colon cancer and melanoma, particularly cervical cancer, comprising administering an effective amount of a compound of formula (I). Another aspect of the invention is the use of the compounds according to formula (I) for the treatment of cervical cancer as well as a method of treatment of cervical cancer comprising administering an effective amount of a compound of formula (I).

In accordance with an aspect of the present invention therefore the invention relates to a compound of general formula I, or an N-oxide, a salt, a tautomer or a stereoisomer of said compound, or a salt of said N-oxide, tautomer or stereoisomer particularly a pharmaceutically acceptable salt thereof, or a mixture of same, as described and defined herein, for use in the treatment or prophylaxis of a disease, especially for use in the treatment of a disease.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of hyperproliferative disorders or disorders responsive to induction of cell death, e.g. apoptosis, especially for the treatment of a hyperproliferative disorder or a disorder responsive to induction of cell death, e.g. apoptosis.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, especially the treatment, wherein the diseases are haematological tumours, solid tumours and/or metastases thereof.

Another aspect of the present invention is the use of a compound of formula (I) or a stereoisomer, a tautomer, an N-oxide, a hydrate, a solvate, or a salt thereof, particularly a pharmaceutically acceptable salt thereof, or a mixture of same, as described herein, in the manufacture of a medicament for the treatment or prophylaxis of a disease, wherein such disease is a hyperproliferative disorder or a disorder responsive to induction of cell death e.g. apoptosis. In an embodiment the disease is a haematological tumour, a solid tumour and/or metastases thereof. In another embodiment the disease is cervical-, breast-, non-small cell lung-, prostate-, colon- and melanoma tumor and/or metastases thereof, in a preferred aspect the disease is cervical tumor.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce cell death e.g. apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death, e.g. apoptosis, of such cell types.

In one aspect, the diseases of said method are haematological tumours, solid tumour and/or metastases thereof. In another aspect the diseases of said method are cervical cancer, NSCLC, prostate cancer, colon cancer and melanoma, particularly cervical cancer.

The compounds of the present invention can be used in particular in therapy and prevention i.e. prophylaxis, especially in therapy of tumour growth and metastases, especially in solid tumours of all indications and stages with or without pre-treatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haematological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents—examples include but are not limited to nitrogen and argon;

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate), flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas), plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. Solution:

A 5 mg/mL solution of the desired compound of this invention can be made using sterile, injectable water, and the pH is adjusted if necessary. The solution is diluted for administration to 1-2 mg/mL with sterile 5% dextrose and is administered as an i.v. infusion over about 60 minutes.

Lyophilised Powder for i.v. Administration:

A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension:

The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haematological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

Experimental Part

The following table lists the abbreviations used in this paragraph and in the Intermediate Examples and Examples section as far as they are not explained within the text body.

| Abbreviation | Meaning |
| --- | --- |
| br | broad |
| CI | chemical ionisation |
| d | doublet |
| dd | doublet of doublet |
| DAD | diode array detector |
| DCM | dichloromethane |
| DMF | N,N-dimethylformamide |
| DMSO | dimethyl sulfoxide |
| ELSD | Evaporative Light Scattering Detector |

| Abbreviation | Meaning |
|---|---|
| eq. | equivalent |
| ESI | electrospray (ES) ionisation |
| h | hours |
| HPLC | high performance liquid chromatography |
| LC-MS | liquid chromatography mass spectrometry |
| m | multiplet |
| min | minutes |
| MS | mass spectrometry |
| NMR | nuclear magnetic resonance spectroscopy : chemical shifts (δ) are given in ppm. The chemical shifts were corrected by setting the DMSO signal to 2.50 ppm using unless otherwise stated. |
| PDA | Photo Diode Array |
| PoraPak ™; | a HPLC column obtainable from Waters |
| q | quartet |
| r.t. or rt | room temperature |
| RT | retention time (as measured either with HPLC or UPLC) in minutes |
| s | singlet |
| SM | starting material |
| SQD | Single-Quadrupol-Detector |
| t | triplet |
| THF | tetrahydrofuran |
| UPLC | ultra performance liquid chromatography |

Other abbreviations have their meanings customary per se to the skilled person. The various aspects of the invention described in this application are illustrated by the following examples which are not meant to limit the invention in any way.

Specific Experimental Descriptions

NMR peak forms in the following specific experimental descriptions are stated as they appear in the spectra, possible higher order effects have not been considered. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash NH$_2$ silica gel in combination with a Isolera® autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated in vacuo" refers to use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only, and are not to be construed as limiting the scope of the invention in any manner. All publications mentioned herein are incorporated by reference in their entirety.

Analytical LC-MS Conditions

LC-MS-data given in the subsequent specific experimental descriptions refer (unless otherwise noted) to the following conditions:

| | |
|---|---|
| System: | Waters Acquity UPLC-MS: Binary Solvent Manager, Sample Manager/Organizer, Column Manager, PDA, ELSD, SQD 3001 or ZQ4000 |
| Column: | Acquity UPLC BEH C18 1.7 50 × 2.1 mm |
| Solvent: | A1 = water + 0.1% vol. formic acid (99%) |
| | A2 = water + 0.2% vol. ammonia (32%) |
| | B1 = acetonitrile |
| Gradient: | 0-1.6 min 1-99% B, 1.6-2.0 min 99% B |
| Flow: | 0.8 mL/min |
| Temperature: | 60° C. |
| Injection: | 2.0 µL |
| Detection: | DAD scan range 210-400 nm -> Peaktable |
| | ELSD |
| | MS ESI+, ESI– Switch -> various scan ranges (Report Header) |
| Methods: | Method 1: A1 + B1 = C:\MassLynx\Mass_100_1000.flp |
| | Method 2: A1 + B1 = C:\MassLynx\Mass_160_1000.flp |
| | Method 3: A1 + B1 = C:\MassLynx\Mass_160_2000.flp |
| | Method 4: A1 + B1 = C:\MassLynx\Mass_160_1000_BasicReport.flp |
| | Method 5: A2 + B1 = C:\MassLynx\NH$_3$_Mass_100_1000.flp |
| | Method 6: A2 + B1 = C:\MassLynx\NH$_3$_Mass_160-_1000_BasicReport.flp |

Preparative HPLC Conditions

"Purification by preparative HPLC" in the subsequent specific experimental descriptions refers to (unless otherwise noted) the following conditions:

Analytics (Pre- and Post Analytics: Method B):

| System: | Waters Aqcuity UPLC-MS: Binary Solvent Manager, Sample Manager/Organizer, Column Manager, PDA, ELSD, SQD 3001 |
|---|---|
| Column: | Aqcuity BEH C18 1.7 50 × 2.1 mm |
| Solvent: | A = water + 0.1% vol. formic acid (99%) B = acetonitrile |
| Gradient: | 0-1.6 min 1-99% B, 1.6-2.0 min 99% B |
| Flow: | 0.8 mL/min |
| Temperature: | 60° C. |
| Injection: | 2 µL |
| Detection: | DAD scan range 210-400 nm MS ESI+, ESI−, scan range 160-1000 m/z ELSD |
| Methods: | Purify_pre.flp Purify_post.flp |

Preparation:

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = water + 0.1% vol. formic acid (99%) B = acetonitrile |
| Gradient: | 0-1 min 1% B, 1-8 min 1-99% B, 8-10 min 99% B |
| Flow: | 50 mL/min |
| Temperature: | RT |
| Solution: | max. 250 mg/2.5 mL dimethyl sufoxide or DMF |
| Injection: | 1 × 2.5 mL |
| Detection: | DAD scan range 210-400 nm MS ESI+, ESI−, scan range 160-1000 m/z |

Chiral HPLC Conditions

If not specified otherwise, chiral HPLC-data given in the subsequent specific experimental descriptions refer to the following conditions:

Analytics:

| System: | Dionex: Pump 680, ASI 100, Waters: UV-Detektor 2487 |
|---|---|
| Column: | Chiralpak IC 5 µm 150 × 4.6 mm |
| Solvent: | hexane/ethanol 80:20 + 0.1% diethylamine |
| Flow: | 1.0 mL/min |
| Temperature: | 25° C. |
| Solution: | 1.0 mg/mL ethanol/methanol 1:1 |
| Injection: | 5.0 µL |
| Detection: | UV 280 nm |

Preparation:

| System: | Agilent: Prep 1200, 2xPrep Pump, DLA, MWD, Prep FC, ESA: Corona |
|---|---|
| Column: | Chiralpak IC 5 µm 250 × 30 mm |
| Solvent: | hexane/ethanol 80:20 + 0.1% diethylamine |
| Flow: | 40 mL/min |
| Temperature: | RT |
| Solution: | 660 mg/5.6 mL ethanol |
| Injection: | 8 × 0.7 mL |
| Detection: | UV 280 nm |

Flash Column Chromatography Conditions

"Purification by (flash) column chromatography" as stated in the subsequent specific experimental descriptions refers to the use of a Biotage Isolera purification system. For technical specifications see "Biotage product catalogue" on www.biotage.com.

Determination of Optical Rotation Conditions

Optical rotations were measured in dimethyl sulfoxide at 589 nm wavelength, 20° C., concentration 1.0000 g/100 mL, integration time 10 s, film thickness 100.00 mm.

EXAMPLES

Synthetic Intermediates

Intermediate 1-1-1

Preparation of 5'-cyclopropyl-1'-(4-ethoxy-2,6-difluorobenzyl)-4'-methyl-1-[2-(morpholin-4-yl)ethyl]-1H,1'H-3,3'-bipyrazol-5-amine

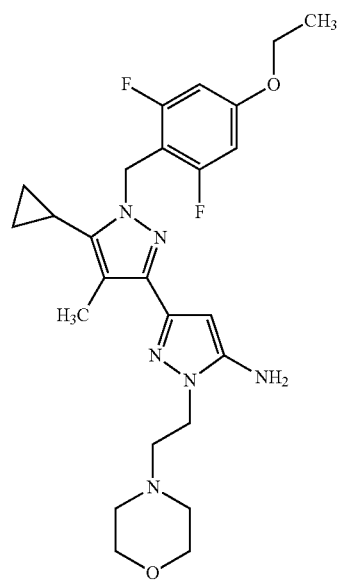 [SMILES: CCOc1cc(F)c(Cn2nc(-c3cc(N)n(CCN4CCOCC4)n3)c(C)c2C2CC2)c(F)c1]

A solution of compound 1-2-1 (500 mg, 1.39 mmol, 1.0 eq.), 4-(2-hydrazinylethyl)morpholine (202 mg, 1.39 mmol 1.0 eq.) and triethylamine (186 µL, 1.33 mmol, 0.96 eq.) in ethanol (8.0 mL) was refluxed under an argon atmosphere overnight. To the reaction mixture was added triethylamine (186 µL, 1.33 mmol, 0.96 eq.) again and the mixture was refluxed overnight once more. After cooling to room temperature the mixture was concentrated in vacuo and the residue was purified by preparative HPLC to yield the desired compound 1-1-1 analytically pure (117 mg, 17%).

$^1$H NMR (300 MHz, DMSO-$d_6$) δ [ppm]=0.67 (d, 2H), 0.99 (dd, 2H), 1.30 (t, 3H), 1.61-1.69 (m, 1H), 2.13 (s, 3H), 2.35-2.43 (m, 4H), 2.59 (t, 2H), 3.49-3.61 (m, 4H), 3.95 (t, 2H), 4.04 (q, 2H), 5.15 (s, 2H), 5.26 (s, 2H), 5.39 (s, 1H), 6.72 (d, 2H).

The following compounds were prepared according to the same procedure from the indicated starting materials (SM=starting material):

| | | | |
|---|---|---|---|
| 1-1-2 SM = 1-2-1 | 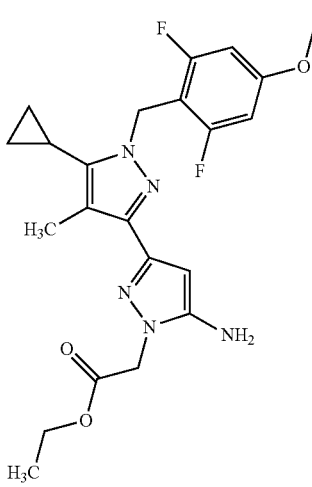 | ethyl [5-amino-5'-cyclopropyl-1'-(4-ethoxy-2,6-difluorobenzyl)-4'-methyl-1H,1'H-3,3'-bipyrazol-1-yl]acetate | ¹H-NMR (400 MHz, DMSO-d₆): δ [ppm] = 0.63-0.71 (m, 2 H), 0.95-1.04 (m, 2 H), 1.19 (t, 3 H), 1.31 (t, 3 H), 1.59-1.72 (m, 1 H), 2.12 (s, 3 H), 4.05 (q, 2 H), 4.12 (q, 2 H), 4.73 (s, 2 H), 5.18 (s, 2 H), 5.27 (s, 2 H), 5.41 (s, 1 H), 6.67-6.75 (m, 2 H). |

Intermediate 1-1-3

Preparation of 1-[5-amino-5'-cyclopropyl-1'-(4-ethoxy-2,6-difluorobenzyl)-4'-methyl-1H,1'H-3,3'-bipyrazol-1-yl]ethanone

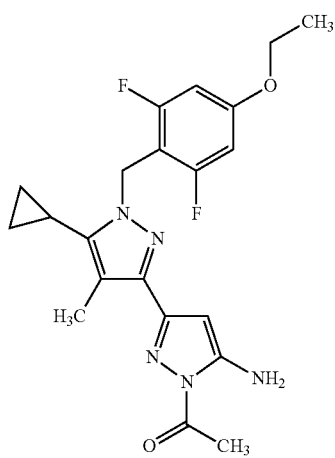 [SMILES: CCOc1cc(F)c(Cn2nc(-c3cc(N)n(C(C)=O)n3)c(C)c2C2CC2)c(F)c1]

A solution of nitrile 1-2-1 (121 mg, 337 µmol, 1.3 eq.) and acethydrazide (90%, 30.5 mg, 370 µmol, 1.1 eq.) in acetic acid (1.05 mL, 33.7 mmol, 100 eq) was stirred overnight at 90 to 110° C. Although the reaction was not completed, the mixture was diluted with water. Thereby a precipitate was formed which was filtrated off and washed subsequent with water and some ethanol. The crude product was purified by flash chromatography to obtain the desired compound 1-1-3 as white solid (27 mg, 18%).

¹H-NMR (400 MHz, DMSO-d₆): δ [ppm]=0.65-0.75 (m, 2H), 0.97-1.06 (m, 2H), 1.31 (t, 3H), 1.62-1.71 (m, 1H), 1.99 (s, 3H), 2.08 (br. s, 3H), 4.01-4.09 (m, 2H), 5.34 (s, 2H), 6.58 (br. s, 1H), 6.69-6.75 (m, 2H), 10.32 (br. s, 1H), 12.26 (s, 1H).

Intermediate 1-1-4

Preparation of N-{5'-cyclopropyl-1'-(4-ethoxy-2,6-difluorobenzyl)-4'-methyl-1-[2-(methylsulfonyl)ethyl]-1H,1'H-3,3'-bipyrazol-5-yl}acetamide

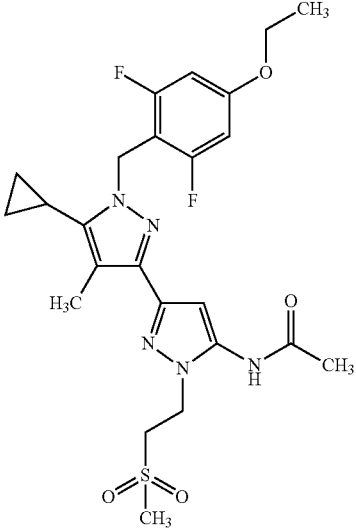 [SMILES: CCOc1cc(F)c(Cn2nc(-c3cc(NC(C)=O)n(CCS(C)(=O)=O)n3)c(C)c2C2CC2)c(F)c1]

To a solution of nitrile 1-2-1 (421 mg, 1.71 mmol, 1.0 eq.) in acetic acid (6.7 mL, 117 mmol, 100 eq.) was added (2-methanesulfonylethyl)hydrazine hydrochloride (307 mg, 1.75 mmol, 1.5 eq.). The reaction mixture was stirred at 90° C. for 4 days. After cooling to room temperature the mixture was diluted with water and concentrated in vacuo. The residue was purified by flash chromatography to yield analytically pure the desired compound (134 mg, 22%).

¹H-NMR (300 MHz, DMSO-d₆): δ [ppm]=0.63-0.76 (m, 2H), 0.96-1.07 (m, 2H), 1.30 (t, 3H), 1.57-1.74 (m, 1H), 2.08 (s, 3H), 2.18 (s, 3H), 2.91 (s, 3H), 3.61 (t, 2H), 4.04 (q, 2H), 4.41 (t, 2H), 5.30 (s, 2H), 6.31 (s, 1H), 6.73 (d, 2H), 10.00 (s, 1H).

Intermediate 1-1-5

Preparation of 5'-cyclopropyl-1'-(4-ethoxy-2,6-difluorobenzyl)-4'-methyl-1-[2-(methylsulfonyl)ethyl]-1H,1'H-3,3'-bipyrazol-5-amine

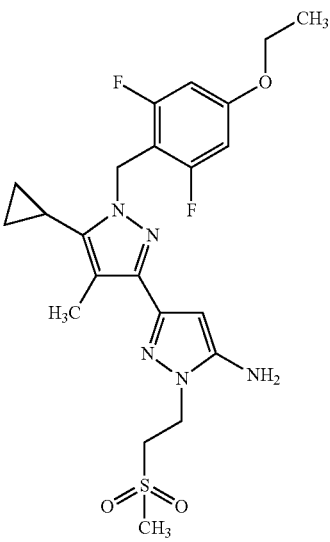 [SMILES: CCOc1cc(F)c(Cn2nc(-c3cc(N)n(CCS(C)(=O)=O)n3)c(C)c2C2CC2)c(F)c1]

To a solution of compound 1-1-4 (116 mg, 222 μmol, 1.0 eq.) in methanol (900 μL) was added 2M aqueous hydrochloric acid (111 μL, 222 μmol, 1.0 eq.). The mixture was stirred at 60° C. for 3 days and subsequent concentrated in vacuo to obtain the desired amine (100 mg, 90%).

$^1$H-NMR (400 MHz, DMSO-$d_6$): δ [ppm]=0.70 (dd, 2H), 1.02 (dd, 2H), 1.31 (t, 3H), 1.58-1.71 (m, 1H), 2.14 (s, 3H), 3.00 (s, 3H), 3.60 (s, 2H), 4.05 (d, 2H), 4.43 (s, 2H), 5.35 (s, 2H), 5.67 (s, 1H), 6.73 (d, 2H)

Intermediate 1-1-6

Preparation of 5'-cyclopropyl-1'-(4-ethoxy-2,6-difluorobenzyl)-1,4'-dimethyl-1H,1'H-3,3'-bipyrazol-5-amine

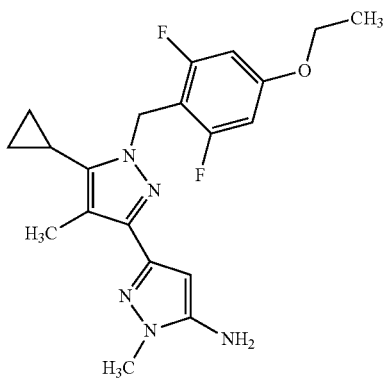 [SMILES: CCOc1cc(F)c(Cn2nc(-c3cc(N)n(C)n3)c(C)c2C2CC2)c(F)c1]

120 mg of 3-[5-cyclopropyl-1-(4-ethoxy-2,6-difluorobenzyl)-4-methyl-1H-pyrazol-3-yl]-3-oxopropanenitrile 1-2-1 (0.334 mmol, 1.0 eq.) and 23 mg of methyl-hydrazine (0.501 mmol, 1.5 eq.) were dissolved in 1 mL methanol in microwave tube. The reaction mixture stirred at 160° C. for 15 min in a microwave oven, afterwards it was concentrated in vacuo. The residue was purified by chromatography to provide 54 mg (40%, 0.14 mmol) of the 97% pure target compound.

$^1$H-NMR (400 MHz, DMSO-$d_6$): δ [ppm]=0.58-0.68 (m, 2H), 0.91-1.00 (m, 2H), 1.27 (t, 3H), 1.55-1.67 (m, 1H), 2.10 (s, 3H), 3.46 (s, 3H), 4.01 (q, 2H), 5.04 (s, 2H), 5.22 (s, 2H), 5.36 (s, 1H), 6.64-6.74 (m, 2H).

Intermediate 1-2-1

Preparation of 3-[5-cyclopropyl-1-(4-ethoxy-2,6-difluorobenzyl)-4-methyl-1H-pyrazol-3-yl]-3-oxo-propanenitrile

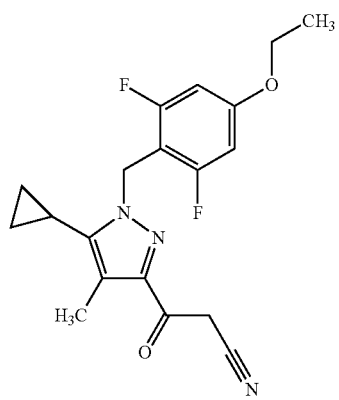 [SMILES: CCOc1cc(F)c(Cn2nc(C(=O)CC#N)c(C)c2C2CC2)c(F)c1]

A 1.6 M solution of n-butyllithium in hexane (36.9 mL, 59.0 mmol, 2.0 eq.) was dropped to a solution of dry acetonitrile (6.2 mL, 118 mmol, 4.0 eq.) in THF (250 mL) at −78° C. The colored mixture was stirred for 1 h at this temperature. Afterwards a solution of compound 1-3-1 (10.3 g, 29.5 mmol, 1.0 eq.) in THF (50 mL) was added. The reaction mixture was allowed to warm up to room temperature and was stirred for 2 h. The mixture was diluted with ethyl acetate and extracted with water. The aqueous layer was extracted again two times with ethyl acetate. The combined organic layers were washed with brine, dried over magnesium sulfate and concentrated in vacuo to give the desired compound 1-2-1 (10.6 g, 98%), which was used without further purification.

$^1$H NMR (300 MHz, DMSO-$d_6$) δ [ppm]=0.64-0.77 (m, 2H), 0.97-1.07 (m, 2H), 1.31 (t, 3H), 1.61-1.70 (m, 1H), 2.12-2.22 (m, 3H), 4.05 (q, 2H), 4.30 (s, 2H), 5.41 (s, 2H), 6.67-6.82 (m, 2H).

Intermediate 1-3-1

Preparation of methyl 5-cyclopropyl-1-(4-ethoxy-2,6-difluorobenzyl)-4-methyl-1H-pyrazole-3-carboxylate

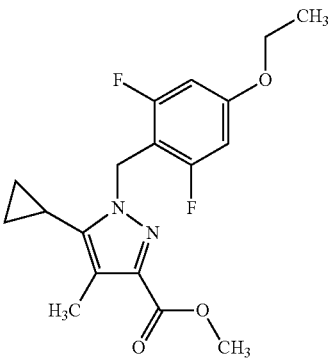 [SMILES: CCOc1cc(F)c(Cn2nc(C(=O)OC)c(C)c2C2CC2)c(F)c1]

To a solution of ester 1-4-1 (90.0 g, 463.4 mmol, 1.0 eq.) in THF (900 mL) was added sodium hydride (60% in mineral oil, 22.2 g, 1.2 eq.) in portions to keep the temperature between 0-5° C. under an argon atmosphere. The ice bath was removed and the reaction mixture was stirred for 30 min to give a slightly brown colored suspension. Afterwards 4-ethoxy-2,6-difluorbenzylbromide (116 g, 463 mmol, 1.0 eq.) was added and the reaction mixture was stirred for 2 h at room temperature. The mixture was carefully diluted with methanol and subsequent dropped into water containing some sodium chloride (2 L). The layers were separated. The aqueous layer was washed three times with ethyl acetate. The combined organic layers were washed with half-saturated sodium chloride solution, dried over magnesium sulfate and concentrated in vacuo to give the crude product, which was purified by digestion with pentan/diethylether 1:1. The desired compound 1-3-1 was obtained, containing 8% of the corresponding ethyl ester (135 g, 83%).

$^1$H NMR (300 MHz, DMSO-$d_6$) δ [ppm]=0.63-0.74 (m, 2H), 0.96-1.08 (m, 2H), 1.24-1.36 (m, 3H), 1.61-1.74 (m, 1H), 2.16 (s, 3H), 3.71 (s, 3H), 4.05 (q, 2H), 5.36 (s, 2H), 6.64-6.82 (m, 2H).

Intermediate 1-4-1

Preparation of ethyl 5-cyclopropyl-4-methyl-1H-pyrazole-3-carboxylate

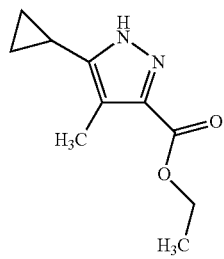

To 10.0 g of ethyl 4-cyclopropyl-3-methyl-2,4-dioxobutanoate 1-6-1 (51 mmol, 1.0 eq.) in 100 mL ethanol were added 3.16 g hydrazine hydrate (80%, 50.4 mmol, 1.0 eq.). The reaction mixture was stirred at 70° C. for 1 h under nitrogen. The solids were filtered off and the filtrate was concentrated in vacuo. The residue was dissolved in 100 mL diethyl ether and 50 mL 2 M hydrochloric acid in diethyl ether was added. After stirring for 2 hours at rt the product was filtered off and dried at 40° C. in vacuo to provide 7.40 g (32 mmol, 66%) of analytically pure target compound.

$^1$H-NMR (300 MHz, DMSO-$d_6$): δ [ppm]=0.62-0.72 (m, 2H), 0.81-0.87 (m, 2H), 1.24 (t, 3H), 1.69-1.83 (m, 1H), 2.16 (s, 3H), 4.21 (q, 2H)

Intermediate 1-6-1

Preparation of ethyl 4-cyclopropyl-3-methyl-2,4-dioxobutanoate

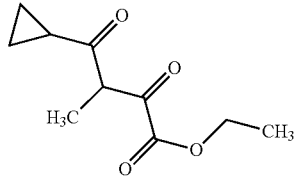

165 mL of an 1 M solution of bis(trimethylsilyl)lithiumamid in THF (166 mmol, 1.10 eq.) were added to 500 mL of diethyl ether and cooled down to 78° C. 14.8 g of 1-cyclopropylpropan-1-one 1-7-1 (150 mmol, 1.0 eq.) were dissolved in 100 mL of diethyl ether and added dropwise at −78° C. The mixture was stirred for one hour at −78° C. and then 24.5 mL of diethyl oxalate (181 mmol, 1.2 eq.) were added dropwise. The cooling bath was removed and the mixture was stirred for 24 hours at rt. 500 mL of aqueous 1M hydrogen chloride solution was added and the mixture was extracted with DCM, dried over a silicone filter and concentrated in vacuo to provide 27.2 g (137 mmol, 91%) of the target compound as crude product. The crude product was used for the following step without further purification.

Intermediate 1-7-1

Preparation of 1-cyclopropylpropan-1-one

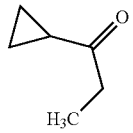

198 mL of a 3M ethylmagnesium bromide solution in diethyl ether (596 mmol, 1.0 eq.) was cooled to 0° C. and 44.2 mL of cyclopropanecarbonitrile dissolved in 80 mL of dry diethyl ether was added dropwise. The mixture was stirred at reflux for 6 hours. It was hydrolysed with aqueous saturated ammonium chloride solution and stirred for 24 hours at rt. The resulting suspension was filtered off and washed with diethyl ether. The filtrate was dried over sodium sulfate and concentrated in vacuo (at 40° C. bath temperature and 600 mbar). Distillation of the crude product in vacuo provided 36.9 g (376 mmol, 63%) of analytically pure target compound.

$^1$H-NMR (400 MHz, DMSO-$d_6$): δ [ppm]=0.73-0.84 (m, 4H), 0.91 (t, 3H), 1.91-2.02 (m, 1H), 2.52 (q, 2H).

Intermediate 1-8-1

Preparation of 3-[5-cyclopropyl-1-(4-ethoxy-2,6-difluorobenzyl)-4-methyl-1H-pyrazol-3-yl]-1-(2-methoxyethyl)-1H-1,2,4-triazol-5-amine

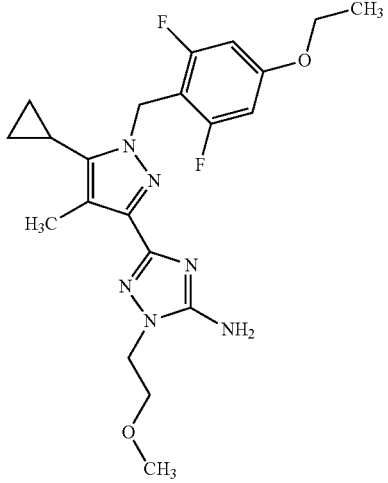 [SMILES: CCOc1cc(F)c(Cn2nc(-c3nc(N)n(CCOC)n3)c(C)c2C2CC2)c(F)c1]

623 mg of 3-[5-cyclopropyl-1-(4-ethoxy-2,6-difluorobenzyl)-4-methyl-1H-pyrazol-3-yl]-1H-1,2,4-triazol-5-amine hydrochloride 1-9-1 (1.5 mmol, 1.0 eq.) were dissolved in 12 mL DMF. 1.05 g of potassium carbonate (7.58 mmol, 5.0 eq.) and 211 mg 2-bromoethyl methyl ether (1.5 mmol, 1.0 eq.) were added and the reaction mixture was stirred at 60° C. overnight. Water and ethyl acetate were added and the layers were separated. The aqueous layer was extracted with ethyl acetate twice. The combined organic layers were dried over a silicon filter and the filtrate was concentrated in vacuo to provide the crude product. The crude product was purified by chromatography to yield 301 mg (41%, 0.62 mmol) of the 89% pure target compound.

$^1$H-NMR (300 MHz, DMSO-$d_6$): δ [ppm]=0.60-0.71 (m, 2H), 0.92-1.04 (m, 2H), 1.27 (t, 3H), 1.57-1.73 (m, 1H), 2.13 (s, 3H), 3.18 (s, 3H), 3.55 (t, 2H), 3.90-4.09 (m, 4H), 5.24 (s, 2H), 6.05 (s, 2H), 6.64-6.77 (m, 2H).

The following compounds were prepared according to the same procedure from the indicated starting materials (SM=starting material):

| | | | |
|---|---|---|---|
| 1-8-2<br>SM =<br>1-9-1 | 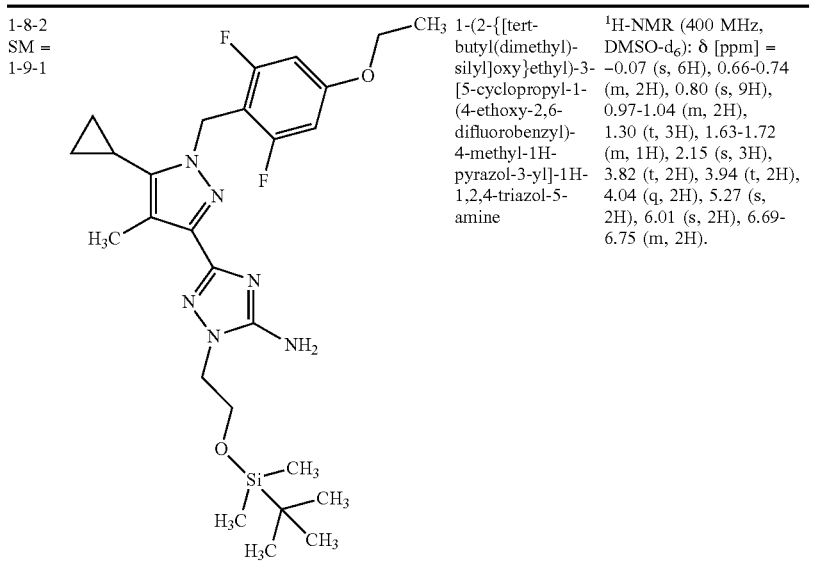 | 1-(2-{[tert-butyl(dimethyl)-silyl]oxy}ethyl)-3-[5-cyclopropyl-1-(4-ethoxy-2,6-difluorobenzyl)-4-methyl-1H-pyrazol-3-yl]-1H-1,2,4-triazol-5-amine | $^1$H-NMR (400 MHz, DMSO-$d_6$): δ [ppm] = −0.07 (s, 6H), 0.66-0.74 (m, 2H), 0.80 (s, 9H), 0.97-1.04 (m, 2H), 1.30 (t, 3H), 1.63-1.72 (m, 1H), 2.15 (s, 3H), 3.82 (t, 2H), 3.94 (t, 2H), 4.04 (q, 2H), 5.27 (s, 2H), 6.01 (s, 2H), 6.69-6.75 (m, 2H). |

Intermediate 1-9-1

Preparation of 3-[5-cyclopropyl-1-(4-ethoxy-2,6-difluorobenzyl)-4-methyl-1H-pyrazol-3-yl]-1H-1,2,4-triazol-5-amine hydrochloride

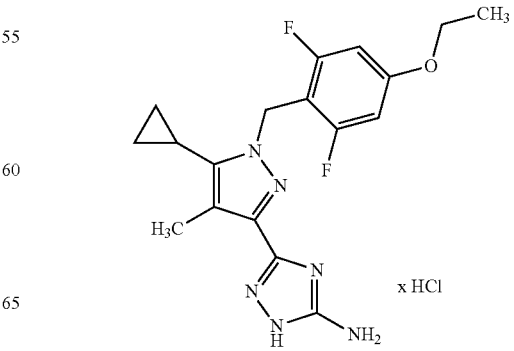

0.76 g of sodium (33 mmol, 4.0 eq.) were added slowly to 35 mL methanol and stirred under nitrogen until sodium completely disappeared. Then the solution was cooled to 0° C. and 4.1 g of aminoguanidine hemisulfate (16 mmol, 2.0 eq.) were added and stirred for 10 min. Afterwards 3.0 g of ethyl 5-cyclopropyl-1-(4-ethoxy-2,6-difluorobenzyl)-4-methyl-1H-pyrazole-3-carboxylate 1-10-1 (8.2 mmol, 1.0 eq.) dissolved in 15 mL methanol were added dropwise, the reaction mixture was allowed to warm to rt and stirred under reflux overnight. The reaction mixture was cooled to 0° C. until a precipitate was built, filtered off and washed with methanol. The combined filtrate was concentrated in vacuo, purified by chromatography to provide 97% pure target compound (1.06 g, 31%, 2.54 mmol).

$^1$H-NMR (300 MHz, DMSO-$d_6$): δ [ppm]=0.60-0.72 (m, 2H), 0.94-1.00 (m, 2H), 1.27 (t, 3H), 1.55-1.72 (m, 1H), 2.13 (s, 3H), 4.01 (q, 2H), 5.26 (br. s, 2H), 5.84 (br. s, 2H), 6.66-6.74 (m, 2H), 11.84 (br. s, 1H).

Intermediate 1-10-1

Preparation of ethyl 5-cyclopropyl-1-(4-ethoxy-2,6-difluorobenzyl)-4-methyl-1H-pyrazole-3-carboxylate

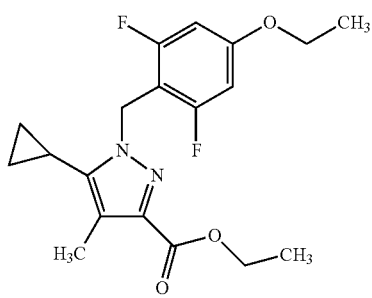 [SMILES: CCOC(=O)c1nn(Cc2c(F)cc(OCC)cc2F)c(C2CC2)c1C]

A solution of ethyl 5-cyclopropyl-4-methyl-1H-pyrazole-3-carboxylate 1-4-1 (46.9 g, 266 mmol, 1.0 eq.) in THF (588 mL) were cooled to 0° C. and sodium hydride (60%, 11.6 g 290 mmol, 1.2 eq.) were added in small portions. The resulting suspension was diluted with 250 mL THF. 2-(Bromomethyl)-5-ethoxy-1,3-difluorobenzene (66.7 g, 266 mmol, 1.1 eq.) were added slowly. The reaction mixture was stirred at rt for 2 h. 300 mL water was added and the THF was evaporated in vacuo. The aqueous residue was extracted with ethyl acetate three times. The combined organic layers were dried over a silicone filter and concentrated in vacuo. The residue was purified by flash chromatography to provide 79.8 g (195 mmol, 81%) of 89% pure target compound.

$^1$H-NMR (400 MHz, CHLOROFORM-d): δ [ppm]=0.65-0.70 (m, 2H), 0.96-1.03 (m, 2H), 1.34-1.42 (m, 7H), 1.47-1.52 (m, 1H), 2.24 (s, 3H), 3.97 (q, 3H), 4.35 (q, 2H), 5.46 (s, 2H), 6.40-6.44 (m, 2H).

Intermediate 1-11-1

Preparation of 3-[1-(4-ethoxy-2,6-difluorobenzyl)-1H-indazol-3-yl]-1-(2-methoxyethyl)-1H-1,2,4-triazol-5-amine

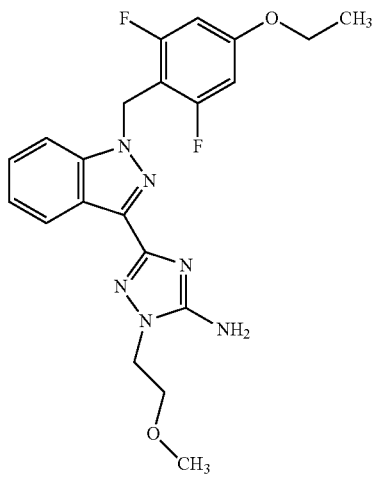 [SMILES: CCOc1cc(F)c(Cn2nc(-c3nc(N)n(CCOC)n3)c3ccccc32)c(F)c1]

115 mg of 3-[1-(4-ethoxy-2,6-difluorobenzyl)-1H-indazol-3-yl]-1H-1,2,4-triazol-5-amine 1-12-1 (0.311 mmol, 1.0 eq.) were dissolved in 2.4 mL DMF. 215 mg of potassium carbonate (1.55 mmol, 5.0 eq.) and 43 mg 2-bromoethyl methyl ether (0.311 mmol, 1.0 eq.) were added and the reaction mixture was stirred at 60° C. overnight. Water and ethyl acetate were added and the layers were separated. The aqueous layer was extracted with ethyl acetate twice. The combined organic layers were dried over a silicon filter and the filtrate was concentrated in vacuo to provide the crude product. The crude product was purified by chromatography to yield 49 mg (28%, 0.086 mmol) of the 75% pure target compound which was used without further purification.

Intermediate 1-11-2

Preparation of 5-[1-(4-ethoxy-2,6-difluorobenzyl)-1H-indazol-3-yl]-1-(2-methoxyethyl)-1H-1,2,4-triazol-3-amine

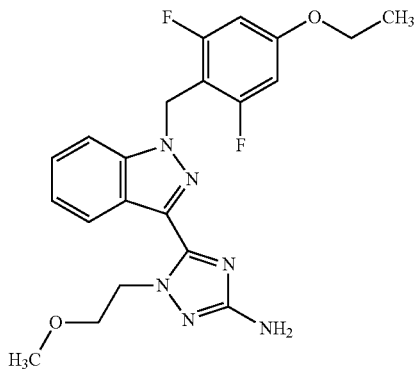 [SMILES: CCOc1cc(F)c(Cn2nc(-c3nc(N)nn3CCOC)c3ccccc32)c(F)c1]

As a side product from the reaction to intermediate 1-11-1 5-[1-(4-ethoxy-2,6-difluorobenzyl)-1H-indazol-3-yl]-1-(2-methoxyethyl)-1H-1,2,4-triazol-3-amine was isolated: 34 mg (19%, 0.060 mmol) of the 63% pure target compound, which was used without further purification.

Intermediate 1-12-1

Preparation of 3-[1-(4-ethoxy-2,6-difluorobenzyl)-1H-indazol-3-yl]-1H-1,2,4-triazol-5-amine

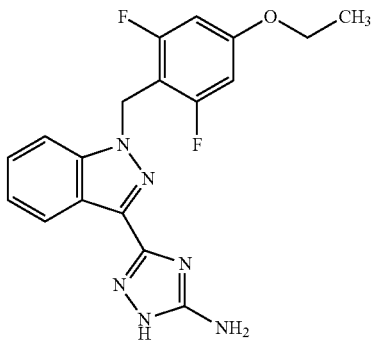 [SMILES: CCOc1cc(F)c(Cn2nc(-c3n[nH]c(N)n3)c3ccccc32)c(F)c1]

0.37 g of sodium (12 mmol, 4.0 eq.) were added slowly to 12 mL methanol and stirred under nitrogen until sodium completely disappeared. Then the solution was cooled to 0° C. and 0.43 g of aminoguanidine hemisulfate (5.8 mmol, 2.0 eq.) were added and stirred for 10 min. Afterwards 1.0 g of methyl 1-(4-ethoxy-2,6-difluorobenzyl)-1H-indazole-3-carboxylate 1-13-1 (2.9 mmol, 1.0 eq.) dissolved in 5 mL methanol were added dropwise. The reaction mixture was allowed to warm to rt and stirred under reflux overnight. The reaction mixture was cooled to 0° C. until a precipitate was built, filtered off and washed with methanol. The combined filtrate was concentrated in vacuo, purified by chromatography to provide 77% pure target compound (115 mg, 8%, 0.24 mmol).

¹H NMR (300 MHz, DMSO-d₆) δ [ppm]=1.25 (t, 3H), 4.00 (q, 2H), 5.56 (s, 2H), 5.96-6.25 (m, 2H), 6.61-6.79 (m, 2H), 7.17 (t, 1H), 7.42 (t, 1H), 7.71 (d, 1H), 8.18 (d, 1H), 12.19 (br. s, 1H).

Intermediate 1-13-1

Preparation of methyl 1-(4-ethoxy-2,6-difluorobenzyl)-1H-indazole-3-carboxylate

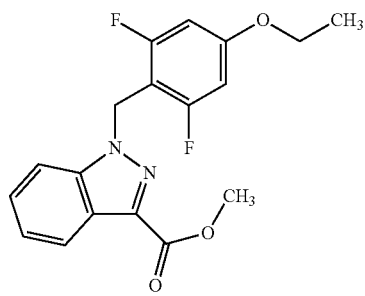 [SMILES: CCOc1cc(F)c(Cn2nc(C(=O)OC)c3ccccc32)c(F)c1]

9.98 g of methyl 1H-indazole-3-carboxylate (CAS Reg. No.: 43120-28-1) (56.65 mmol, 1 eq.) were dissolved in 260 mL of dry tetrahydrofuran at 0° C. 22.15 g of cesium carbonate (67.98 mmol, 1.2 eq.) and 15.65 g 2-(bromomethyl)-1,3-difluorobenzene (62.31 mmol, 1.1 eq.) were added. The mixture was stirred at room temperature for five hours under a nitrogen atmosphere. Then the reaction mixture was concentrated in vacuo. The residue was partitioned between dichloromethane and half saturated aqueous sodium bicarbonate solution. The organic layer was washed with water, dried over sodium sulfate and concentrated in vacuo yielding 21.18 g of the title compound (61.15 mmol, 108.0%). The material was pure enough for further processing.

¹H NMR (400 MHz, DMSO-d₆) δ [ppm]=1.26 (t, 3H), 3.86 (s, 3H), 4.01 (q, 2H), 5.68 (s, 2H), 6.73 ("d", 2H), 7.33 ("t", 1H), 7.51 ("t", 1H), 7.83 ("d", 1H), 8.04 ("d", 1H).

The following compounds were prepared according to the same procedure from the indicated starting materials (SM=starting material):

| | | | |
|---|---|---|---|
| 1-13-2<br>SM =<br>3-iodo-1H-indazole<br>(CAS-Reg.-No.:<br>66607-27-0) | 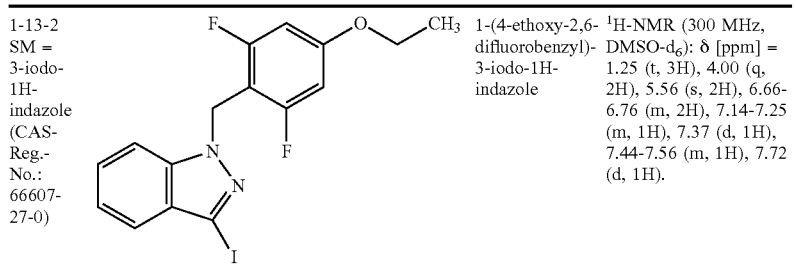 | 1-(4-ethoxy-2,6-difluorobenzyl)-3-iodo-1H-indazole | ¹H-NMR (300 MHz, DMSO-d₆): δ [ppm] = 1.25 (t, 3H), 4.00 (q, 2H), 5.56 (s, 2H), 6.66-6.76 (m, 2H), 7.14-7.25 (m, 1H), 7.37 (d, 1H), 7.44-7.56 (m, 1H), 7.72 (d, 1H). |

Intermediate 1-14-1

Preparation of 1-[1-(4-ethoxy-2,6-difluorobenzyl)-1H-indazol-3-yl]-1H-pyrazol-4-amine

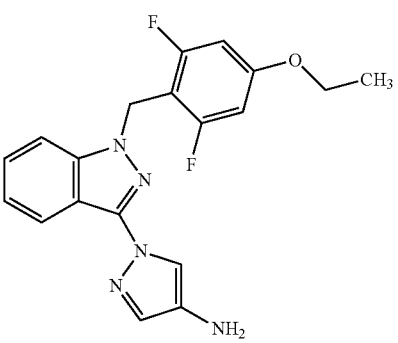 [SMILES: CCOc1cc(F)c(Cn2nc(-n3cc([N+](=O)[O-])cn3)c3ccccc32)c(F)c1]

25 mg of 1-(4-ethoxy-2,6-difluorobenzyl)-3-(4-nitro-1H-pyrazol-1-yl)-1H-indazole 1-15-1 (0.063 mmol, 1.0 eq.) were dissolved in methanol and 21 mg raney nickel (50%, 0.125 mmol, 2.0 eq.) and 0.044 mL hydrazine hydrate (35%, 0.313 mmol, 5.0 eq.) were added. The reaction mixture was stirred at room temperature under argon for 4 h and was filtered through celite, washed with ethanol and the combined filtrates were concentrated in vacuo. The 84% pure crude product was used without further purification: 24 mg, 87%, 0.05 mmol.

$^1$H NMR (300 MHz, DMSO-d$_6$) δ [ppm]=1.25 (t, 3H), 3.99 (q, 2H), 4.23 (br. s, 2H), 5.50 (s, 2H), 6.70 (d, 2H), 7.14 (t, 1H), 7.31 (s, 1H), 7.39-7.49 (m, 1H), 7.52 (s, 1H), 7.67 (d, 1H), 8.14 (d, 1H).

Intermediate 1-15-1

Preparation of 1-(4-ethoxy-2,6-difluorobenzyl)-3-(4-nitro-1H-pyrazol-1-yl)-1H-indazole

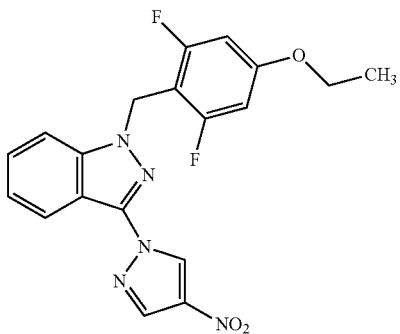

Cesium carbonate was dried in a drying cabinet at 50° C. 200 mg of 1-(4-Ethoxy-2,6-difluorobenzyl)-3-iodo-1H-indazole 1-13-2 (0.48 mmol, 1.0 eq.), 109 mg of 4-nitro-1H-pyrazole (0.97 mmol, 2.0 eq.), 315 mg of cesium carbonate (0.97 mmol, 2.0 eq.), 3.84 mg of copper (II) oxide (0.048 mmol, 0.1 eq.) and 51 mg of iron (III) acetyl acetonate (0.15 mmol, 0.3 eq.) were dissolved in 1 mL DMF. The reaction mixture was degased and stirred in a microwave vial at 90° C. for 5 days. Water and dichloromethane were added and stirred for 5 min., then it was poured through a silicon filter, concentrated in vacuo and purified by HPLC to provide the analytically pure target compound: 25 mg, 13%, 0.06 mmol).

$^1$H NMR (300 MHz, DMSO-d$_6$) δ [ppm]=1.25 (t, 3H), 4.00 (q, 2H), 5.63 (s, 2H), 6.65-6.77 (m, 2H), 7.29 (t, 1H), 7.56 (t, 1H), 7.83 (d, 1H), 8.02 (d, 1H), 8.62 (s, 1H), 9.19 (s, 1H).

Intermediate 1-16-1

Preparation of 3-[1-(2-fluorobenzyl)-1H-indazol-3-yl]-1,2,4-thiadiazol-5-amine

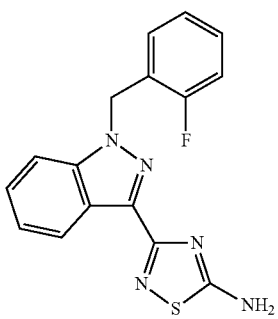 [SMILES: Nc1nc(-c2nn(Cc3ccccc3F)c3ccccc23)ns1]

150 mg of 1-(2-fluorobenzyl)-1H-indazole-3-carboximidamide hydrochloride (1:1) (CAS-Reg.-No.: 256376-75-7) (0.49 mmol, 1.0 eq.) were dissolved in 2.68 ml of methanol and cooled to 0° C. At this temperature 0.17 ml of triethylamine (1.23 mmol, 2.5 eq.), were added and the mixture stirred at 0° C. for 10 minutes. Then 33 mg of potassium thiocyanate (0.97 mmol, 0.7 eq.) dissolved in 0.5 mL of methanol were added dropwise. The cooling bath was removed and the mixture was allowed to come to room temperature, while forming a precipitate. The precipitate was filtered off to provide the analytically pure target compound: 28 mg, 17%, 0.09 mmol).

$^1$H NMR (300 MHz, DMSO-d$_6$) δ [ppm]=5.73 (s, 2H), 7.07-7.27 (m, 4H), 7.32 (m, 1H), 7.43 (tbr, 1H), 7.75 (d, 1H), 8.03 (s, 2H), 8.33 (d, 1H).

Example Compounds

Example 2-1-1

Preparation of 5'-cyclopropyl-1'-(4-ethoxy-2,6-difluorobenzyl)-4'-methyl-1-[2-(morpholin-4-yl)ethyl]-N-(pyrimidin-4-yl)-1H,1'H-3,3'-bipyrazol-5-amine

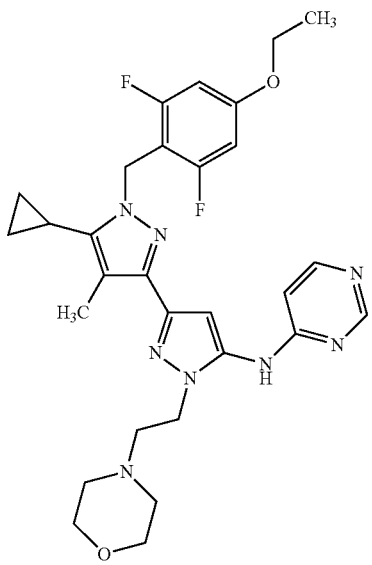 [SMILES: CCOc1cc(F)c(Cn2nc(-c3cc(Nc4ccncn4)n(CCN4CCOCC4)n3)c(C)c2C2CC2)c(F)c1]

To a suspension of 1-1-1 (114 mg, 234 μmol, 1.0 eq.) in DMF (901 μL) 4-bromopyrimidine hydrochloride (51.9 mg, 258 μmol, 1.1 eq.), cesium carbonate (229 mg, 703 μmol, 3.0 eq.), 4,5-bis(diphenylphosphino)-9,9-dimethylxanthene (20.3 mg, 35.1 μmol, 0.15 eq.) and palladium(II) acetate (5.3 mg, 23.4 μmol, 0.1 eq.) were added under an argon atmosphere. The reaction mixture was stirred in a sealed tube at 105° C. overnight. After cooling to room temperature the mixture was filtrated off and concentrated in vacuo. The remaining material was purified by preparative HPLC to yield the desired compound 2-1-1 analytically pure (3.2 mg, 2.2%).

$^1$H NMR (300 MHz, DMSO-d$_6$) δ [ppm]=0.64-0.75 (m, 2H), 0.96-1.06 (m, 2H), 1.30 (t, 3H), 1.60-1.73 (m, 1H), 2.19 (s, 3H), 2.35 (br. s, 4H), 2.62-2.66 (m, 2H), 3.42-3.49 (m, 4H), 4.04 (q, 2H), 4.11-4.18 (m, 2H), 5.31 (s, 2H), 6.34 (s, 1H), 6.78-6.71 (m, 3H), 8.31 (d, 1H), 8.61 (s, 1H), 9.63 (s, 1H).

The following compounds were prepared according to the same procedure from the indicated starting materials (SM=starting material):

| | | | |
|---|---|---|---|
| 2-1-2 SM = 1-1-3 | 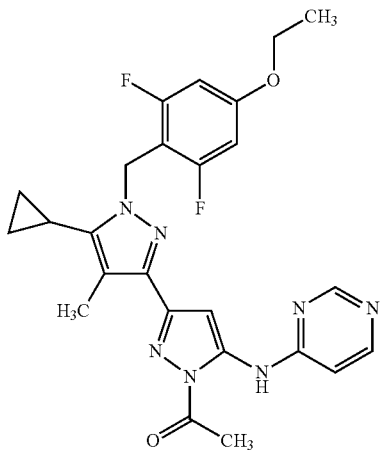 [SMILES: CCOc1cc(F)c(Cn2nc(-c3cc(Nc4ccncn4)n(C(C)=O)n3)c(C)c2C2CC2)c(F)c1] | 1-[5'-cyclopropyl-1'-(4-ethoxy-2,6-difluorobenzyl)-4'-methyl-5-(pyrimidin-4-ylamino)-1H,1'H-3,3'-bipyrazol-1-yl]ethanone | $^1$H-NMR (300 MHz, DMSO-d$_6$): δ [ppm] = 0.67-0.79 (m, 2 H), 0.97-1.12 (m, 2 H), 1.31 (t, 3 H), 1.59-1.78 (m, 1 H), 2.24 (s, 3 H), 2.31 (s, 3 H), 4.05 (q, 2 H), 5.37 (s, 2 H), 6.75 (d, 2 H), 6.96 (s, 1 H), 7.90 (dd, 1 H), 8.89 (d, 1 H), 9.11 (d, 1 H), 11.52 (s, 1 H). |
| 2-1-3 SM = 1-1-2 | 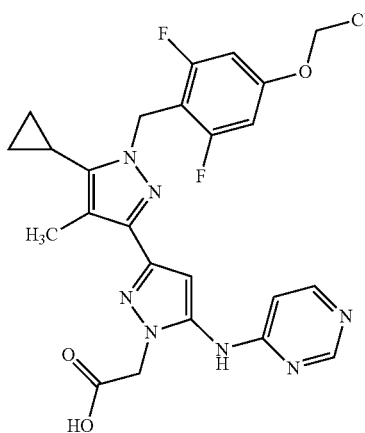 | [5'-cyclopropyl-1'-(4-ethoxy-2,6-difluorobenzyl)-4'-methyl-5-(pyrimidin-4-ylamino)-1H,1'H-3,3'-bipyrazol-1-yl]acetic acid | $^1$H-NMR (400 MHz, DMSO-d$_6$): δ [ppm] = 0.70 (dd, 2 H), 1.00 (dd, 2 H), 1.30 (t, 3 H), 1.60-1.72 (m, 1 H), 2.19 (s, 3 H), 4.05 (d, 2 H), 4.49 (s, 2 H), 5.32 (s, 2 H), 6.45 (s, 1 H), 6.66-6.80 (m, 3 H), 6.85-7.43 (m, 1 H), 8.27 (d, 1 H), 8.61 (d, 1 H), 10.79-11.76 (m, 1 H). |
| 2-1-4 SM = 1-1-6 | 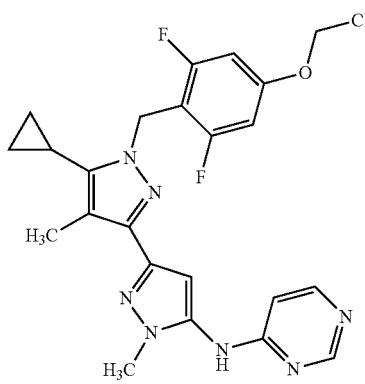 | 5'-cyclopropyl-1'-(4-ethoxy-2,6-difluorobenzyl)-1,4'-dimethyl-N-(pyrimidin-4-yl)-1H,1'H-3,3'-bipyrazol-5-amine | $^1$H-NMR (300 MHz, DMSO-d$_6$): δ [ppm] = 0.58-0.72 (m, 2H), 0.93-1.06 (m, 2H), 1.27 (t, 3H), 1.57-1.70 (m, 1H), 2.16 (s, 3H), 3.64 (s, 3H), 4.01 (q, 2H), 5.27 (s, 2H), 6.33 (s, 1H), 6.62-6.76 (m, 3H), 8.27 (d, 1H), 8.51-8.66 (m, 1H), 9.39 (br. s., 1H). |

| | | | |
|---|---|---|---|
| 2-1-5 SM = 1-8-1 | 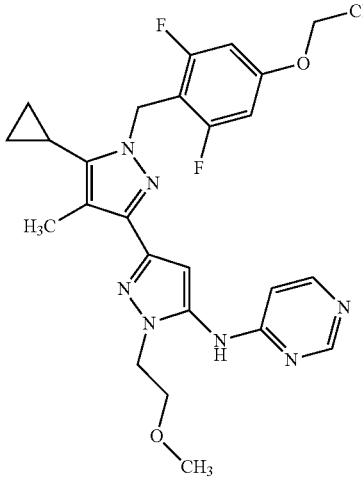 | N-{3-[5-cyclopropyl-1-(4-ethoxy-2,6-difluorobenzyl)-4-methyl-1H-pyrazol-3-yl]-1-(2-methoxyethyl)-1H-1,2,4-triazol-5-yl}pyrimidin-4-amine | $^1$H-NMR (300 MHz, DMSO-$d_6$): δ [ppm] = 0.64-0.72 (m, 2H), 0.92-1.05 (m, 2H), 1.27 (t, 3H), 1.58-1.74 (m, 1H), 2.18 (s, 3H), 3.15 (s, 3H), 3.62 (t, 2H), 4.01 (q, 2H), 4.28 (t, 2H), 5.32 (s, 2H), 6.67-6.76 (m, 2H), 7.59 (d, 1H), 8.45 (d, 1H), 8.67 (s, 1H), 10.19 (br. s., 1H). |

Example 2-2-1

Preparation of 5'-cyclopropyl-1'-(4-ethoxy-2,6-difluorobenzyl)-4'-methyl-1-[2-(methylsulfonyl)ethyl]-N-(pyrimidin-4-yl)-1H,1'H-3,3'-bipyrazol-5-amine

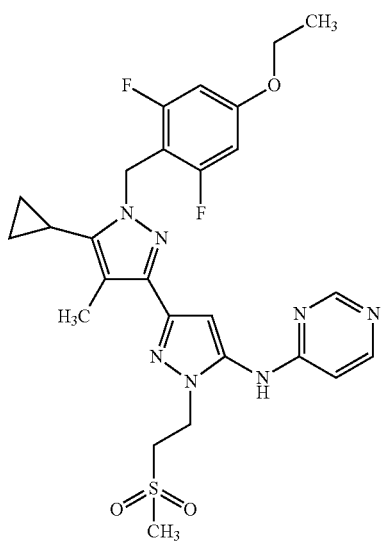 [SMILES: CCOc1cc(F)c(Cn2nc(-c3cc(Nc4ccncn4)n(CCS(C)(=O)=O)n3)c(C)c2C2CC2)c(F)c1]

To a suspension of 1-1-5 (105 mg, 219 µmol, 1.0 eq.), 4-bromopyrimidine hydrochloride (47.0 mg, 241 µmol, 1.1 eq.), cesium carbonate (214 mg, 657 µmol, 3.0 eq.) and 4,5-bis(diphenylphosphino)-9,9-dimethylxanthene (19.0 mg, 33.0 µmol, 0.15 eq.) in DMF (1.7 mL) was added palladium(II) acetate (4.9 mg, 22 µmol, 0.1 eq.) under an argon atmosphere. The reaction mixture was stirred in a sealed tube at 105° C. overnight. After cooling to room temperature 4-bromopyrimidine hydrochloride (47.0 mg, 241 µmol, 1.1 eq.) and palladium(II) acetate (4.9 mg, 22 µmol, 0.1 eq.) were added to the mixture and it was stirred for 3 h at 105° C., for 3 days at room temperature and again for 3 h at 105° C. After cooling to ambient temperature the mixture was filtered, the filtrate was concentrated in vacuo and the residue was purified by preparative HPLC to yield the desired compound 2-2-1 (2.0 mg, 1.5%).

$^1$H NMR (600 MHz, DMSO-$d_6$) δ [ppm]=0.73-0.78 (m, 2H), 1.03-1.09 (m, 2H), 1.28-1.33 (m, 3H), 1.70-1.76 (m, 1H), 2.08 (s, 3H), 2.87 (s, 3H), 3.46 (t, 2H), 4.05 (q, 2H), 4.56 (t, 2H), 5.39 (s, 2H), 6.57 (s, br., 1H), 6.73 (d, 2H), 8.28 (d, 1H), 8.58 (s, 1H), 9.99 (s, 1H).

Example 2-3-1

Preparation of 5'-cyclopropyl-1'-(4-ethoxy-2,6-difluorobenzyl)-1,4'-dimethyl-N-(pyridin-4-yl)-1H,1'H-3,3'-bipyrazol-5-amine

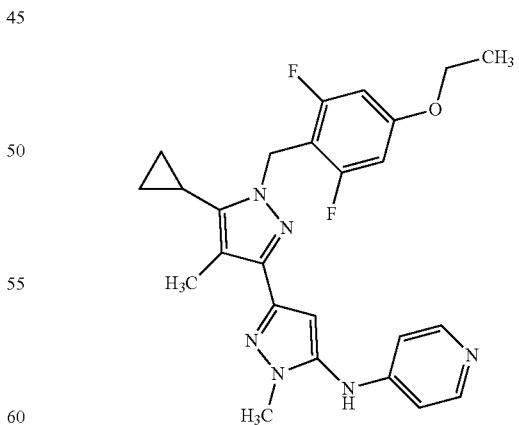

70 mg of 5'-cyclopropyl-1'-(4-ethoxy-2,6-difluorobenzyl)-1,4'-dimethyl-1H,1'H-3,3'-bipyrazol-5-amine 1-1-6 (0.18 mmol, 1.0 eq.) were dissolved in 0.7 mL DMF. 39 mg of 4-bromo-pyridine hydrochloride (0.20 mmol, 1.1 eq.), 177 mg cesium carbonate (0.54 mmol, 3.0 eq.), 4.1 mg of palladium(II) acetate (0.018 mmol, 0.1 eq.) and 16 mg of 4,5-bis(diphenylphosphino)-9,9-dimethylxanthene (0.027 mmol, 0.15 eq.) were added under an argon atmosphere. The reaction mixture was stirred in a sealed tube at 105° C. for 3 h. After cooling to ambient temperature water and ethyl acetate were added. The layers were separated and the aqueous layer was extracted with ethyl acetate twice. The combined organic layers were dried over a silicon filter, concentrated in vacuo and the residue was purified by chromatography to yield the desired compound (61 mg, 72%, 0.13 mmol).

$^1$H-NMR (400 MHz, DMSO-$d_6$): δ [ppm]=0.64-0.68 (m, 2H), 0.94-1.02 (m, 2H), 1.27 (t, 3H), 1.59-1.68 (m, 1H), 2.16 (s, 3H), 3.61 (s, 3H), 4.01 (q, 2H), 5.27 (s, 2H), 6.12 (s, 1H), 6.63-6.73 (m, 4H), 8.16 (d, 2H), 8.62 (s, 1H).

The following compounds were prepared according to the same procedure from the indicated starting materials (SM=starting material):

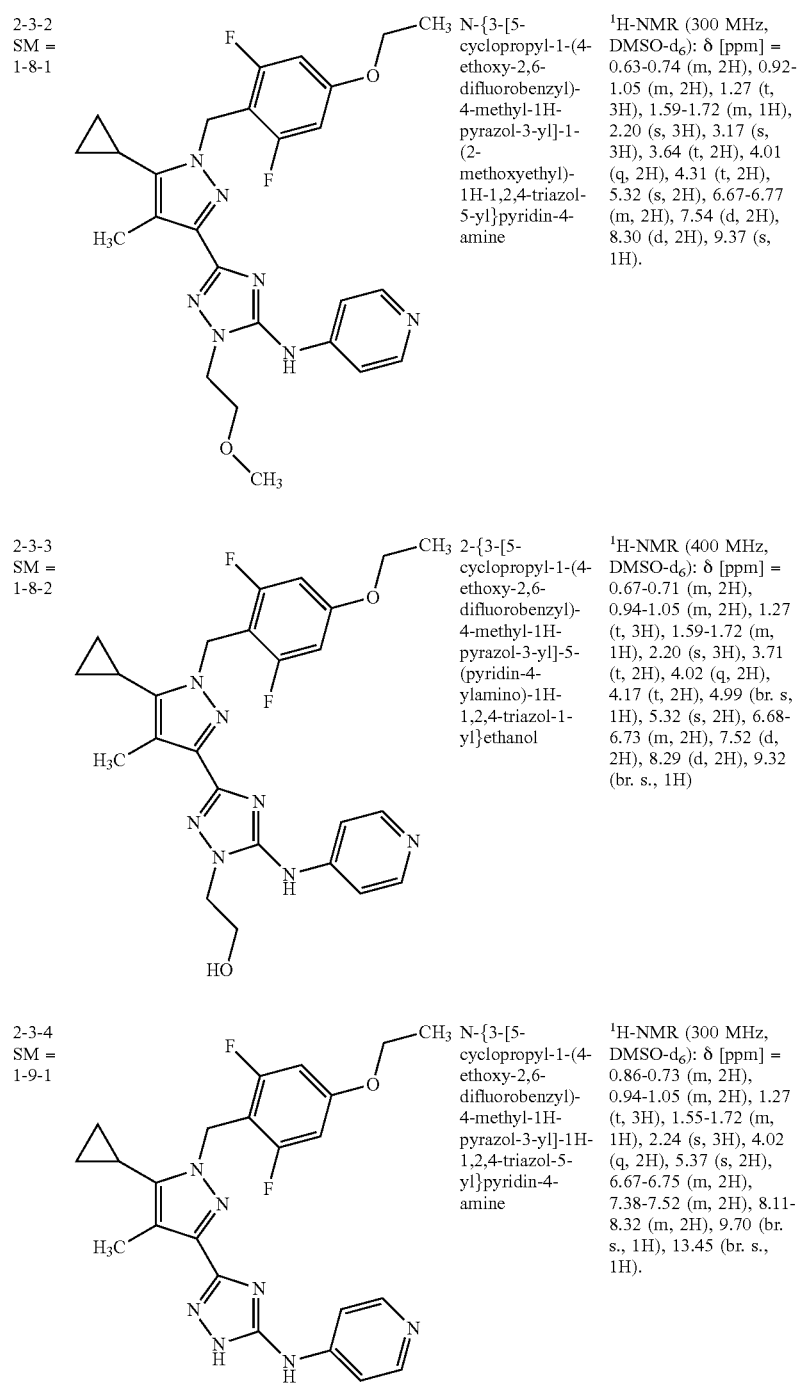

| | | | |
|---|---|---|---|
| 2-3-2<br>SM =<br>1-8-1 | | N-{3-[5-cyclopropyl-1-(4-ethoxy-2,6-difluorobenzyl)-4-methyl-1H-pyrazol-3-yl]-1-(2-methoxyethyl)-1H-1,2,4-triazol-5-yl}pyridin-4-amine | $^1$H-NMR (300 MHz, DMSO-$d_6$): δ [ppm] = 0.63-0.74 (m, 2H), 0.92-1.05 (m, 2H), 1.27 (t, 3H), 1.59-1.72 (m, 1H), 2.20 (s, 3H), 3.17 (s, 3H), 3.64 (t, 2H), 4.01 (q, 2H), 4.31 (t, 2H), 5.32 (s, 2H), 6.67-6.77 (m, 2H), 7.54 (d, 2H), 8.30 (d, 2H), 9.37 (s, 1H). |
| 2-3-3<br>SM =<br>1-8-2 | | 2-{3-[5-cyclopropyl-1-(4-ethoxy-2,6-difluorobenzyl)-4-methyl-1H-pyrazol-3-yl]-5-(pyridin-4-ylamino)-1H-1,2,4-triazol-1-yl}ethanol | $^1$H-NMR (400 MHz, DMSO-$d_6$): δ [ppm] = 0.67-0.71 (m, 2H), 0.94-1.05 (m, 2H), 1.27 (t, 3H), 1.59-1.72 (m, 1H), 2.20 (s, 3H), 3.71 (t, 2H), 4.02 (q, 2H), 4.17 (t, 2H), 4.99 (br. s, 1H), 5.32 (s, 2H), 6.68-6.73 (m, 2H), 7.52 (d, 2H), 8.29 (d, 2H), 9.32 (br. s., 1H) |
| 2-3-4<br>SM =<br>1-9-1 | | N-{3-[5-cyclopropyl-1-(4-ethoxy-2,6-difluorobenzyl)-4-methyl-1H-pyrazol-3-yl]-1H-1,2,4-triazol-5-yl}pyridin-4-amine | $^1$H-NMR (300 MHz, DMSO-$d_6$): δ [ppm] = 0.86-0.73 (m, 2H), 0.94-1.05 (m, 2H), 1.27 (t, 3H), 1.55-1.72 (m, 1H), 2.24 (s, 3H), 4.02 (q, 2H), 5.37 (s, 2H), 6.67-6.75 (m, 2H), 7.38-7.52 (m, 2H), 8.11-8.32 (m, 2H), 9.70 (br. s., 1H), 13.45 (br. s., 1H). |

Example 2-4-1

Preparation of ethyl 4-({3-[5-cyclopropyl-1-(4-ethoxy-2,6-difluorobenzyl)-4-methyl-1H-pyrazol-3-yl]-1-(2-methoxyethyl)-1H-1,2,4-triazol-5-yl}amino)nicotinate

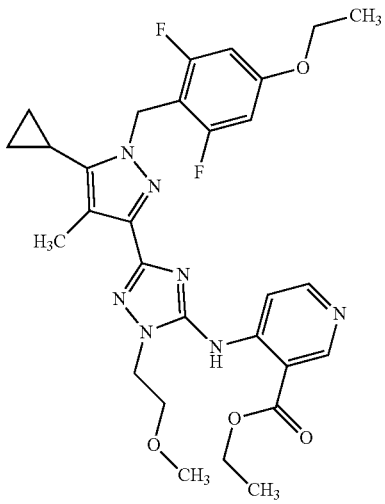 [SMILES: CCOC(=O)c1cnccc1Nc1nc(-c2nn(Cc3c(F)cc(OCC)cc3F)c(C3CC3)c2C)nn1CCOC]

150 mg of 3-[5-cyclopropyl-1-(4-ethoxy-2,6-difluorobenzyl)-4-methyl-1H-pyrazol-3-yl]-1-(2-methoxyethyl)-1H-1,2,4-triazol-5-amine 1-8-1 (0.35 mmol, 1.0 eq.) were dissolved in 1.3 mL DMF. 85 mg of ethyl 4-chloronicotinate hydrochloride (0.38 mmol, 1.1 eq.), 339 mg cesium carbonate (1.04 mmol, 3.0 eq.), 7.8 mg of palladium(II) acetate (0.035 mmol, 0.1 eq.) and 30 mg of 4,5-bis(diphenylphosphino)-9,9-dimethylxanthene (0.052 mmol, 0.15 eq.) were added under an argon atmosphere. The reaction mixture was stirred in a sealed tube at 105° C. for 3 h. After cooling to ambient temperature water and ethyl acetate were added. The layers were separated and the aqueous layer was extracted with ethyl acetate twice. The combined organic layers were dried over a silicon filter, concentrated in vacuo and the residue was purified by chromatography to yield the desired compound in 96% purity (3 mg, 1%).

$^1$H-NMR (300 MHz, DMSO-$d_6$): δ [ppm]=0.69-0.75 (m, 2H), 0.99-1.06 (m, 2H), 1.30 (t, 3H), 1.36 (t, 3H), 1.63-1.76 (m, 1H), 2.23 (s, 3H), 3.25 (s, 3H), 3.67 (t, 2H), 4.04 (q, 2H), 4.26 (t, 2H), 4.39 (q, 2H), 5.35 (s, 2H), 6.71-6.79 (m, 2H), 8.05 (d, 1H), 8.49 (d, 1H), 8.96 (s, 1H), 10.55 (s, 1H).

Example 2-5-1

Preparation of N-{3-[1-(4-ethoxy-2,6-difluorobenzyl)-1H-indazol-3-yl]-1-(2-methoxyethyl)-1H-1,2,4-triazol-5-yl}pyridin-4-amine

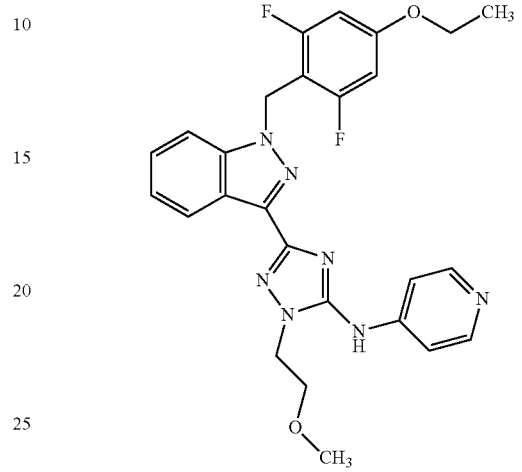

49 mg of 3-[1-(4-ethoxy-2,6-difluorobenzyl)-1H-indazol-3-yl]-1-(2-methoxyethyl)-1H-1,2,4-triazol-5-amine 1-11-1 (75% pure, 0.086 mmol, 1.0 eq.) were dissolved in 0.33 mL DMF. 18 mg of 4-bromopyridine hydrochloride (0.094 mmol, 1.1 eq.), 84 mg cesium carbonate (0.26 mmol, 3.0 eq.), 1.9 mg of palladium(II) acetate (0.009 mmol, 0.1 eq.) and 7.4 mg of 4,5-bis(diphenylphosphino)-9,9-dimethylxanthene (0.013 mmol, 0.15 eq.) were added under an argon atmosphere. The reaction mixture was stirred in a sealed tube at 105° C. overnight. After cooling to ambient temperature the reaction mixture was diluted with DMSO and purified by HPLC to yield the desired compound in 90% purity (23 mg, 48%, 0.04 mmol).

$^1$H-NMR (300 MHz, DMSO-$d_6$): δ [ppm]=1.25 (t, 3H), 3.21 (s, 3H), 3.73 (t, 2H), 4.00 (q, 2H), 4.39 (t, 2H), 5.64 (s, 2H), 6.68-6.78 (m, 2H), 7.26 (t, 1H), 7.46 (t, 1H), 7.62 (d, 2H), 7.74 (d, 1H), 8.25 (d, 1H), 8.36 (d, 2H), 9.52 (br. s., 1H).

The following compounds were prepared according to the same procedure from the indicated starting materials (SM=starting material):

| | | | |
|---|---|---|---|
| 2-5-2<br>SM =<br>1-11-2 | 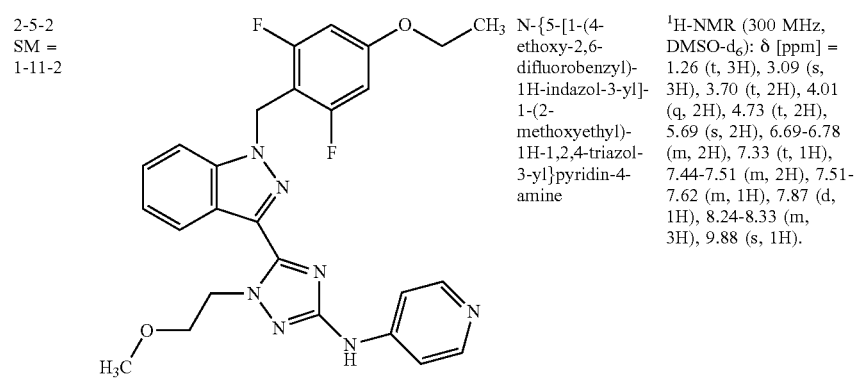 | N-{5-[1-(4-ethoxy-2,6-difluorobenzyl)-1H-indazol-3-yl]-1-(2-methoxyethyl)-1H-1,2,4-triazol-3-yl}pyridin-4-amine | $^1$H-NMR (300 MHz, DMSO-$d_6$): δ [ppm] = 1.26 (t, 3H), 3.09 (s, 3H), 3.70 (t, 2H), 4.01 (q, 2H), 4.73 (t, 2H), 5.69 (s, 2H), 6.69-6.78 (m, 2H), 7.33 (t, 1H), 7.44-7.51 (m, 2H), 7.51-7.62 (m, 1H), 7.87 (d, 1H), 8.24-8.33 (m, 3H), 9.88 (s, 1H). |

Example 2-6-1

Preparation of N-{1-[1-(4-ethoxy-2,6-difluorobenzyl)-1H-indazol-3-yl]-1H-pyrazol-4-yl}pyrimidin-4-amine

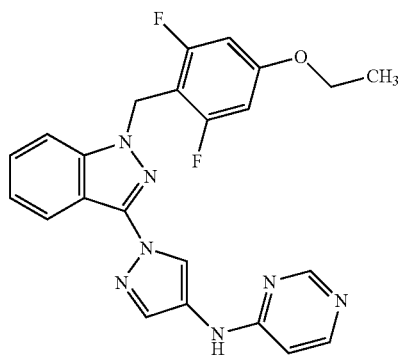 [SMILES: CCOc1cc(F)c(Cn2nc(-n3cc(Nc4ccncn4)cn3)c3ccccc32)c(F)c1]

90 mg of 1-[1-(4-ethoxy-2,6-difluorobenzyl)-1H-indazol-3-yl]-1H-pyrazol-4-amine 1-14-1 (0.24 mmol, 1.0 eq.) were dissolved in 1.9 mL DMF. 41 mg of 4-chloropyrimidine hydrochloride (0.27 mmol, 1.1 eq.), 238 mg cesium carbonate (0.73 mmol, 3.0 eq.), 5.5 mg of palladium(II) acetate (0.024 mmol, 0.1 eq.) and 21 mg of 4,5-bis(diphenylphosphino)-9,9-dimethylxanthene (0.037 mmol, 0.15 eq.) were added under an argon atmosphere. The reaction mixture was stirred in a sealed tube at 105° C. overnight. After cooling to ambient temperature water and dichloromethane were added. The layers were separated and the aqueous layer was extracted with dichloromethane three times. The combined organic layers were washed with water and brine, dried over a silicon filter, concentrated in vacuo and the residue was purified by chromatography to yield the desired compound in 97% purity (11 mg, 10%, 0.02 mmol).

$^1$H-NMR (300 MHz, DMSO-$d_6$): δ [ppm]=1.28 (t, 3H), 4.02 (q, 2H), 5.62 (s, 2H), 6.71-6.79 (m, 3H), 7.18-7.29 (m, 1H), 7.46-7.56 (m, 1H), 7.75 (d, 1H), 7.90 (d, 1H), 8.15-8.28 (m, 2H), 8.67 (d, 2H), 9.84 (s, 1H).

Example 2-7-1

Preparation of N-{3-[1-(2-fluorobenzyl)-1H-indazol-3-yl]-1,2,4-thiadiazol-5-yl}-pyridin-4-amine

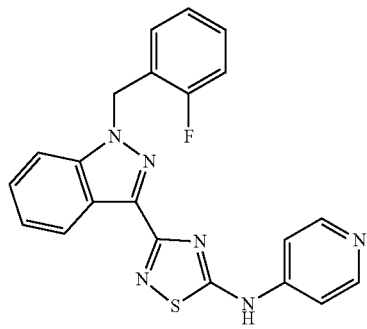 [SMILES: Fc1ccccc1Cn1nc(-c2nsc(Nc3ccncc3)n2)c2ccccc21]

43 mg of 3-[1-(2-fluorobenzyl)-1H-indazol-3-yl]-1,2,4-thiadiazol-5-amine 1-16-1 (0.13 mmol, 1.0 eq.) were suspended in 1 mL of DMF. To this mixture 47 mg of 4-bromopyridine hydrobromide (1:1) (0.20 mmol, 1.5 eq.), 129 mg cesium carbonate (0.40 mmol, 3.0 eq.), 3.0 mg of palladium(II) acetate (0.013 mmol, 0.1 eq.) and 11.5 mg of 4,5-bis(diphenylphosphino)-9,9-dimethylxanthene (0.020 mmol, 0.15 eq.) were added under an argon atmosphere. The reaction mixture was stirred in a sealed tube at 105° C. for 3 hours and then at room temperature overnight. The crude mixture was filtered over a 2 g SiO$_2$-cartridge, washed with methanol, concentrated in vacuo and the residue was purified by chromatography to yield the desired compound in 98% purity (12 mg, 23%, 0.03 mmol).

$^1$H-NMR (300 MHz, DMSO-$d_6$): δ [ppm]=5.83 (s, 2H), 7.12 (m, 2H), 7.21 (m, 1H), 7.4629-7.37 (m, 2H), 7.48 (m, 1H), 7.54-7.61 (m, 2H), 7.79 (d, 1H), 8.38 (d, 1H), 8.50 (m, 2H), 11.52 (s, 1H).

Biological Investigations

The following assays can be used to illustrate the commercial utility of the compounds according to the present invention.

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

Biological Assay 1.0:

Bub1 Kinase Assay

Bub1-inhibitory activities of compounds described in the present invention were quantified using a time-resolved fluorescence energy transfer (TR-FRET) kinase assay which measures phosphorylation of the synthetic peptide Biotin-Ahx-VLLPKKSFAEPG (SEQ ID No. 1) (C-terminus in amide form), purchased from e.g. Biosyntan (Berlin, Germany) by the (recombinant) catalytic domain of human Bub1 (amino acids 704-1085), expressed in Hi5 insect cells with an N-terminal His6-tag and purified by affinity- (Ni-NTA) and size exclusion chromatography.

In a typical assay 11 different concentrations of each compound (0.1 nM, 0.33 nM, 1.1 nM, 3.8 nM, 13 nM, 44 nM, 0.15 μM, 0.51 μM, 1.7 μM, 5.9 μM and 20 μM) were tested in duplicate within the same microtiter plate. To this end, 100-fold concentrated compound solutions (in DMSO) were previously prepared by serial dilution (1:3.4) of 2 mM stocks in a clear low volume 384-well source microtiter plate (Greiner Bio-One, Frickenhausen, Germany), from which 50 nL of compounds were transferred into a black low volume test microtiter plate from the same supplier. Subsequently, 2 μL of Bub1 (the final concentration of Bub1 was adjusted depending on the activity of the enzyme lot in order to be within the linear dynamic range of the assay: typically ~200 ng/mL were used) in aqueous assay buffer [50 mM Tris/HCl pH 7.5, 10 mM magnesium chloride (MgCl$_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added to the compounds in the test plate and the mixture was incubated for 15 min at 22° C. to allow pre-equilibration of the putative enzyme-inhibitor complexes before the start of the kinase reaction, which was initiated by the addition of 3 μL 1.67-fold concentrated solution (in assay buffer) of adenosine-tri-phosphate (ATP, 10 μM final concentration) and peptide substrate (1 μM final concentration). The resulting mixture (5 μL final volume) was incubated at 22° C. during 60 min., and the reaction was stopped by the addition of 5 μL of an aqueous EDTA-solution (50 mM EDTA, in 100 mM HEPES pH 7.5 and 0.2% (w/v) bovine serum albumin) which also contained the TR-FRET detection reagents (0.2 μM streptavidin-XL665 [Cisbio Bioassays, Codolet, France] and 1 nM anti-phospho-Serine antibody [Merck Millipore, cat. #35-001] and 0.4 nM LANCE EU-W1024 labeled anti-mouse IgG antibody [Perkin-Elmer, product no. AD0077, alternatively a Terbium-cryptate-labeled anti-mouse IgG antibody from Cisbio Bioassays can be used]). The stopped reaction mixture was further incubated 1 h at 22° C. in order to allow the formation of complexes between peptides and detection reagents. Subsequently, the amount of product was evaluated by measurement of the resonance energy transfer from the Eu-chelate-antibody complex recognizing the Phosphoserine residue to the streptavidin-XL665 bound to the biotin moiety of the peptide. To this end, the fluorescence emissions at 620 nm and 665 nm after excitation at 330-350 nm were measured in a TR-FRET plate reader, e.g. a Rubystar or Pherastar (both from BMG Labtechnologies, Offenburg, Germany) or a Viewlux (Perkin-Elmer) and the ratio of the emissions (665 nm/622 nm) was taken as indicator for the amount of phosphorylated substrate. The data were normalised using two sets of (typically 32-) control wells for high- (=enzyme reaction without inhibitor=0%=Minimum inhibition) and low- (=all assay components without enzyme=100%=Maximum inhibition) Bub1 activity. 1050 values were calculated by fitting the normalized inhibition data to a 4-parameter logistic equation (Minimum, Maximum, IC50, Hill; Y=Max+(Min−Max)/(1+(X/IC50)Hill)).

Biological Assay 2.0:

Proliferation Assay:

Cultivated tumor cells (cells were ordered from ATCC) were plated at a density of 3000 cells/well in a 96-well multititer plate in 200 μL of growth medium supplemented 10% fetal calf serum. After 24 hours, the cells of one plate (zero-point plate) were stained with crystal violet (see below), while the medium of the other plates was replaced by fresh culture medium (200 μL), to which the test substances were added in various concentrations (0 μM, as well as in the range of 0.001-10 μM; the final concentration of the solvent dimethyl sulfoxide was 0.5%). The cells were incubated for 4 days in the presence of test substances. Cell proliferation was determined by staining the cells with crystal violet: the cells were fixed by adding 20 μL/measuring point of an 11% glutaric aldehyde solution for 15 minutes at room temperature. After three washing cycles of the fixed cells with water, the plates were dried at room temperature. The cells were stained by adding 100 μL/measuring point of a 0.1% crystal violet solution (pH 3.0). After three washing cycles of the stained cells with water, the plates were dried at room temperature. The dye was dissolved by adding 100 μL/measuring point of a 10% acetic acid solution. Absorbtion was determined by photometry at a wavelength of 595 nm. The change of cell number, in percent, was calculated by normalization of the measured values to the absorbtion values of the zero-point plate (=0%) and the absorbtion of the untreated (0 μm) cells (=100%). The $IC_{50}$ values were determined by means of a 4 parameter fit.

TABLE 1

Compounds had been evaluated in the HeLa human cervical cancer cell line to demonstrate antiproliferative activity. The following table gives the data regarding Bub1 kinase inhibition, and inhibition of HeLa cell proliferation, for the examples of the present invention for the biological assays 1 and 2:

| Example No. | Biological Assay 1: Bub1 kinase assay median $IC_{50}$ [mol/l] | Biological Assay 2: Proliferation assay (HeLa cell line) median $IC_{50}$ [mol/l] |
|---|---|---|
| 2-1-1 | 6.8E−7 | nd |
| 2-1-2 | 2.0E−5 | >1.0E−5 |
| 2-1-3 | 1.1E−6 | >1.0E−5 |
| 2-1-4 | 3.4E−8 | nd |
| 2-1-5 | 3.0E−7 | 5.7E−6 |
| 2-2-1 | 2.0E−5 | nd |
| 2-3-1 | 3.9E−7 | 3.5E−6 |
| 2-3-2 | 1.2E−8 | >1.0E−5 |
| 2-3-3 | 2.2E−8 | >1.0E−5 |
| 2-3-4 | 8.2E−8 | nd |
| 2-4-1 | 9.1E−8 | nd |
| 2-5-1 | 1.3E−8 | nd |
| 2-5-2 | 6.0E−7 | nd |
| 2-6-1 | 2.6E−8 | >1.0E−5 |
| 2-7-1 | 2.2E−6 | 9.1E−6 |

The invention claimed is:
1. A compound of formula (I)

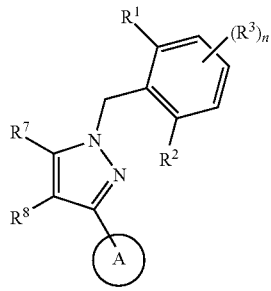

wherein

is a

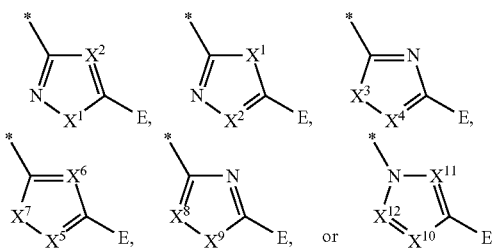

group, wherein the * is the point of attachment;
wherein
$X^1$ is $NR^{18}$, O, or S;
$X^2$ is $CR^4$ or N;
$X^3$ is $NR^{18}$, O, or S;
$X^4$ is $CR^4$ or N;
$X^5$ is $CR^4$ or N;
$X^6$ is $CR^4$;
$X^7$ is $NR^{18}$;
$X^8$ is $CR^4$;
$X^9$ is $NR^{18}$, O, or S;
$X^{10}$ is $CR^4$ or N;
$X^{11}$ is $CR^4$ or N;
$X^{12}$ is $CR^4$ or N; and
E is a

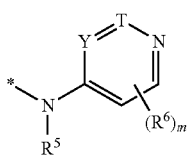

group,
wherein the * is the point of attachment;
T is CH, $CR^{17}$ or N;
Y is CH, $CR^{17}$ or N;
wherein one or both of T and Y is CH or $CR^{17}$;
and
$R^1$ and $R^2$ are independently from each other hydrogen or halogen;

each $R^3$ is independently 1-6C-alkyl, 1-6C-alkoxy, halogen, 2-6C-alkenyl, 3-6C-cycloalkyl, 1-6C-haloalkoxy, or —C(O)OH;
and
n is 0, 1, 2 or 3;
or
$R^3$ is -(1-6C-alkylene)-S—$R^{14}$, -(1-6C-alkylene)-S(O)—$R^{14}$, -(1-6C-alkylene)-S(O)$_2$—$R^{14}$, -(1-6C-alkylene)-S(=O)(=N$R^{15}$)$R^{14}$, —O-(1-6C-alkylene)-S—$R^{14}$, —O-(1-6C-alkylene)-S(O)—$R^{14}$, —O-(1-6C-alkylene)-S(O)$_2$—$R^{14}$, or —O-(1-6C-alkylene)-S(=O)(=N$R^{15}$)$R^{14}$;
and
n is 1;
each $R^4$ is independently
(a) hydrogen,
(b) hydroxy,
(c) 1-6C-alkoxy optionally substituted with
(c1) 1 or 2 hydroxy,
(c2) —N$R^9R^{10}$,
(c3) —S—$R^{14}$,
(c4) —S(O)—$R^{14}$,
(c5) —S(O)$_2$—$R^{14}$,
(c6) —S(=O)(=N$R^{15}$)$R^{14}$, or
(c7) —S(O)$_2$N$R^9R^{10}$,
(d)

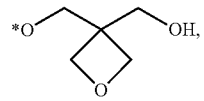

wherein the * is the point of attachment,
(e)

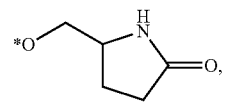

wherein the * is the point of attachment,
(f) cyano, or
(g) —S(O)$_2$-(1-4C-alkyl);
$R^5$ is
(a) hydrogen,
(b) 2-6C-hydroxyalkyl,
(c)

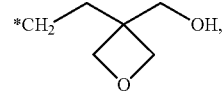

wherein the * is the point of attachment,
(d) —C(O)-(1-6C-alkyl),
(e) —C(O)-(1-6C-alkylene)-O-(1-6C-alkyl), or
(f) —C(O)-(1-6C-alkylene)-O-(1-6C-alkylene)-O-(1-6C-alkyl);
each $R^6$ is independently halogen, cyano, C(O)N$R^{11}R^{12}$, or C(O)O$R^{13}$;
m is 0, 1, or 2;
$R^7$ is hydrogen, halogen, cyano, 1-6C-alkyl, 2-6C-alkenyl, 1-6C-alkoxy, 1-6C-haloalkoxy, 3-6C-cycloalkyl, C(O)N$R^{11}R^{12}$ or —N$R^9R^{10}$;
$R^8$ is hydrogen, halogen, cyano, 1-6C-alkyl, 2-6C-alkenyl, 1-6C-alkoxy, 1-6C-haloalkoxy, 3-6C-cycloalkyl or —N$R^9R^{10}$;
or
$R^7$ and $R^8$ come together to form a n-propylene or a n-butylene group;

R⁹ and R¹⁰ are independently from each other hydrogen or 1-6C-alkyl;
or
R⁹ and R¹⁰ together with the nitrogen atom to which they are attached form a 4-6-membered heterocyclic ring optionally containing one further heteroatom selected from the group consisting of O, S and N;
R¹¹ and R¹² are independently from each other hydrogen, 1-6C-alkyl, 2-6C-hydroxyalkyl, or (1-4C-alkyl)-S(O)₂-(1-4C-alkyl);
each R¹³ is independently hydrogen or 1-4C-alkyl;
each R¹⁴ is independently a group selected from 1-6C-alkyl, 3-7C-cycloalkyl, phenyl and benzyl,
  wherein said group is optionally substituted with one, two or three substituents, identically or differently, selected from the group consisting of hydroxy, halogen, and —NR⁹R¹⁰;
each R¹⁵ is independently hydrogen, cyano, or —C(O)R¹⁶;
R¹⁶ is 1-6C-alkyl or 1-6C-haloalkyl;
each R¹⁷ is independently halogen, cyano, —C(O)NR¹¹R¹², or —C(O)OR¹³;
R¹⁸ is
  (a) hydrogen,
  (b) 1-6C-alkyl optionally substituted with
    (b1) 1 or 2 hydroxy,
    (b2) 1-6C-alkoxy,
    (b3) —C(O)OR¹³,
    (b4) —C(O)NR¹¹R¹²,
    (b5) —NR⁹R¹⁰,
    (b6) —S—R¹⁴,
    (b7) —S(O)—R¹⁴,
    (b8) —S(O)₂—R¹⁴,
    (b9) —S(=O)(=NR¹⁵)R¹⁴, or
    (b10) —S(O)₂NR⁹R¹⁰,
  (c) —S(O)₂-(1-4C-alkyl), or
  (d) —C(O)-(1-6C-alkyl);
or an N-oxide, a salt, a tautomer or a stereoisomer of said compound, or a salt of said N-oxide, tautomer or stereoisomer.

2. The compound according to claim 1,
wherein

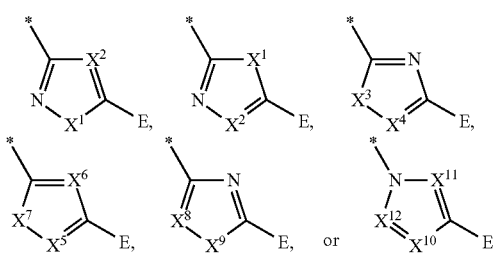

group, wherein the * is the point of attachment;
wherein
X¹ is NR¹⁸, O, or S;
X² is CR⁴ or N;
X³ is NR¹⁸, O, or S;
X⁴ is CR⁴ or N;
X⁵ is CR⁴ or N;
X⁶ is CR⁴;
X⁷ is NR¹⁸;
X⁸ is CR⁴;
X⁹ is NR¹⁸, O, or S;
X¹⁰ is CR⁴ or N;
X¹¹ is CR⁴ or N;
X¹² is CR⁴ or N; and
E is a

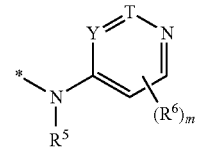

group,
wherein the * is the point of attachment;
T is CH, CR¹⁷ or N;
Y is CH, CR¹⁷ or N;
wherein one or both of T and Y is CH or CR¹⁷;
and
R¹ and R² are independently from each other hydrogen or halogen;
each R³ is independently 1-3C-alkoxy;
and
n is 0, 1, 2, or 3;
or
R³ is -(1-4C-alkylene)-S—R¹⁴, -(1-4C-alkylene)-S(O)—R¹⁴, -(1-4C-alkylene)-S(O)₂—R¹⁴, -(1-4C-alkylene)-S(=O)(=NR¹⁵)R¹⁴, —O-(1-4C-alkylene)-S—R¹⁴, —O-(1-4C-alkylene)-S(O)—R¹⁴, —O-(1-4C-alkylene)-S(O)₂—R¹⁴, or —O-(1-4C-alkylene)-S(=O)(=NR¹⁵)R¹⁴;
and
n is 1;
R⁴ is independently from each other
  (a) hydrogen,
  (b) hydroxy,
  (c) 1-4C-alkoxy optionally substituted with
    (c1) 1 or 2 hydroxy,
    (c2) —NR⁹R¹⁰,
    (c3) —S—R¹⁴,
    (c4) —S(O)—R¹⁴,
    (c5) —S(O)₂—R¹⁴,
    (c6) —S(=O)(=NR¹⁵)R¹⁴, or
    (c7) —S(O)₂NR⁹R¹⁰,
  (f) cyano, or
  (g) —S(O)₂-(1-4C-alkyl);
R⁵ is hydrogen;
each R⁶ is independently halogen, cyano, —C(O)NR¹¹R¹², or —C(O)OR¹³;
m is 0, 1, or 2;
R⁷ is hydrogen, halogen, cyano, 1-3C-alkyl, 2-3C-alkenyl, 1-3C-alkoxy, 1-3C-haloalkoxy, 3-6C-cycloalkyl, —C(O)NR¹¹R¹² or —NR⁹R¹⁰;
R⁸ is hydrogen, halogen, cyano, 1-3C-alkyl, 2-3C-alkenyl, 1-3C-alkoxy, 1-3C-haloalkoxy, 3-6C-cycloalkyl or —NR⁹R¹⁰;
R⁹ and R¹⁰ are independently from each other hydrogen or 1-3C-alkyl;
or
R⁹ and R¹⁰ together with the nitrogen atom to which they are attached form a 4-6-membered heterocyclic ring optionally containing one further heteroatom selected from the group consisting of O, S and N;

$R^{11}$ and $R^{12}$ are independently from each other hydrogen, 1-3C-alkyl, or 2-3C-hydroxyalkyl;

each $R^{13}$ is independently hydrogen or 1-3C-alkyl;

each $R^{14}$ is independently a group selected from 1-3C-alkyl, and 3-7C-cycloalkyl;

each $R^{15}$ is independently hydrogen, cyano, or —C(O)$R^{16}$;

$R^{16}$ is methyl or trifluoromethyl;

each $R^{17}$ is independently halogen, cyano, —C(O)NR$^{11}$R$^{12}$, or —C(O)OR$^{13}$;

$R^{18}$ is
(a) hydrogen,
(b) 1-4C-alkyl optionally substituted with
   (b1) 1 or 2 hydroxy,
   (b2) 1-3C-alkoxy,
   (b3) —C(O)OR$^{13}$,
   (b4) —C(O)NR$^{11}$R$^{12}$,
   (b5) —NR$^9$R$^{10}$,
   (b6) —S—R$^{14}$,
   (b7) —S(O)—R$^{14}$,
   (b8) —S(O)$_2$—R$^{14}$,
   (b9) —S(=O)(=NR$^{15}$)R$^{14}$, or
   (b10) —S(O)$_2$NR$^9$R$^{10}$,
(c) —S(O)$_2$-(1-4C-alkyl), or
(d) —C(O)-(1-3C-alkyl);

or an N-oxide, a salt, a tautomer or a stereoisomer of said compound, or a salt of said N-oxide, tautomer or stereoisomer.

3. The compound according to claim 1, wherein

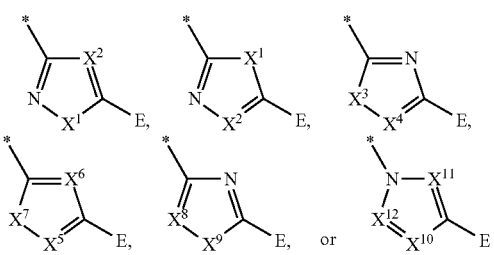

is a group, wherein the * is the point of attachment;
wherein
$X^1$ is NR$^{18}$, O, or S;
$X^2$ is CR$^4$ or N;
$X^3$ is NR$^{18}$, O, or S;
$X^4$ is CR$^4$ or N;
$X^5$ is CR$^4$ or N;
$X^6$ is CR$^4$;
$X^7$ is NR$^{18}$;
$X^8$ is CR$^4$;
$X^9$ is NR$^{18}$, O, or S;
$X^{10}$ is CR$^4$ or N;
$X^{11}$ is CR$^4$ or N;
$X^{12}$ is CR$^4$ or N; and E is a

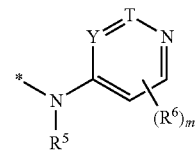

group,
wherein the * is the point of attachment;
T is CH, CR$^{17}$ or N;
Y is CH, CR$^{17}$ or N;
wherein one or both of T and Y is CH or CR$^{17}$;
and $R^1$ and $R^2$ are independently from each other hydrogen or halogen;

$R^3$ is 1-3C-alkoxy;

n is 0 or 1;

each $R^4$ is independently
(a) hydrogen, or
(c) 1-4C-alkoxy optionally substituted with
   (c1) hydroxy,
   (c3) —S—R$^{14}$,
   (c4) —S(O)—R$^{14}$,
   (c5) —S(O)$_2$—R$^{14}$,
   (c6) —S(=O)(=NR$^{15}$)R$^{14}$, or
   (c7) —S(O)$_2$NR$^9$R$^{10}$;

$R^5$ is hydrogen;

$R^6$ is —C(O)NR$^{11}$R$^{12}$ or —C(O)OR$^{13}$;

m is 0 or 1;

$R^7$ is 3-6C-cycloalkyl;

$R^8$ is 1-3C-alkyl;

$R^9$ and $R^{10}$ are independently from each other hydrogen or 1-3C-alkyl;
or $R^9$ and $R^{10}$ together with the nitrogen atom to which they are attached form a 4-6-membered heterocyclic ring optionally containing one further heteroatom selected from the group consisting of O, S and N;

$R^{11}$ and $R^{12}$ are independently from each other hydrogen or 1-3C-alkyl;

each $R^{13}$ is independently hydrogen or 1-3C-alkyl;

$R^{14}$ is 1-3C-alkyl;

$R^{15}$ is hydrogen;

each $R^{17}$ is independently —C(O)NR$^{11}$R$^{12}$ or —C(O)OR$^{13}$;

$R^{18}$ is
(a) hydrogen,
(b) 1-4C-alkyl optionally substituted with
   (b1) hydroxy,
   (b2) 1-3C-alkoxy,
   (b3) —C(O)OR$^{13}$,
   (b4) —C(O)NR$^{11}$R$^{12}$,
   (b5) —NR$^9$R$^{10}$,
   (b6) —S—R$^{14}$,
   (b7) —S(O)—R$^{14}$,
   (b8) —S(O)$_2$—R$^{14}$, or
   (b9) —S(=O)(=NR$^{15}$)R$^{14}$, or
(d) —C(O)-(1-3C-alkyl);

or an N-oxide, a salt, a tautomer or a stereoisomer of said compound, or a salt of said N-oxide, tautomer or stereoisomer.

4. The compound according to claim 1, wherein

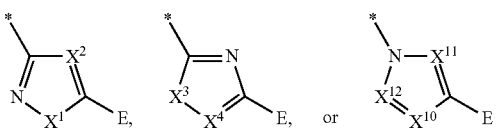

is a

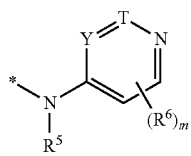

group, wherein the * is the point of attachment; wherein
$X^1$ is $NR^{18}$ or S;
$X^2$ is $CR^4$ or N;
$X^3$ is $NR^{18}$;
$X^4$ is N;
$X^{10}$ is $CR^4$;
$X^{11}$ is $CR^4$;
$X^{12}$ is N; and
E is a group,
wherein the * is the point of attachment,
T is CH;
Y is CH or N;
and
$R^1$ and $R^2$ are independently from each other hydrogen or fluoro;
$R^3$ is ethoxy;
n is 0 or 1;
$R^4$ is hydrogen;
$R^5$ is hydrogen;
$R^6$ is —C(O)$OR^{13}$;
m is 0 or 1;
$R^7$ is cyclopropyl;
$R^8$ is methyl;
$R^9$ and $R^{10}$ together with the nitrogen atom to which they are attached form a morpholine ring;
each $R^{13}$ is independently hydrogen or ethyl;
$R^{14}$ is methyl;
$R^{18}$ is
  (a) hydrogen,
  (b) 1-2C-alkyl optionally substituted with
    (b1) hydroxy,
    (b2) methoxy,
    (b3) —C(O)$OR^{13}$,
    (b5) —$NR^9R^{10}$, or
    (b8) —S(O)$_2$—$R^{14}$, or
  (d) acetyl;
or an N-oxide, a salt, a tautomer or a stereoisomer of said compound, or a salt of said N-oxide, tautomer or stereoisomer.

5. The compound according to claim 1, which is selected from the group consisting of:
5'-cyclopropyl-1'-(4-ethoxy-2,6-difluorobenzyl)-4'-methyl-1-[2-(morpholin-4-yl)ethyl]-N-(pyrimidin-4-yl)-1H,1'H-3,3'-bipyrazol-5-amine;
1-[5'-cyclopropyl-1'-(4-ethoxy-2,6-difluorobenzyl)-4'-methyl-5-(pyrimidin-4-ylamino)-1H,1'H-3,3'-bipyrazol-1-yl]ethanone;
[5'-cyclopropyl-1'-(4-ethoxy-2,6-difluorobenzyl)-4'-methyl-5-(pyrimidin-4-ylamino)-1H,1'H-3,3'-bipyrazol-1-yl]acetic acid;
5'-cyclopropyl-1'-(4-ethoxy-2,6-difluorobenzyl)-1,4'-dimethyl-N-(pyrimidin-4-yl)-1H,1'H-3,3'-bipyrazol-5-amine;
N-{3-[5-cyclopropyl-1-(4-ethoxy-2,6-difluorobenzyl)-4-methyl-1H-pyrazol-3-yl]-1-(2-methoxyethyl)-1H-1,2,4-triazol-5-yl}pyrimidin-4-amine;
5'-cyclopropyl-1'-(4-ethoxy-2,6-difluorobenzyl)-4'-methyl-1-[2-(methylsulfonyl)ethyl]-N-(pyrimidin-4-yl)-1H,1'H-3,3'-bipyrazol-5-amine;
5'-cyclopropyl-1'-(4-ethoxy-2,6-difluorobenzyl)-1,4'-dimethyl-N-(pyridin-4-yl)-1H,1'H-3,3'-bipyrazol-5-amine;
N-{3-[5-cyclopropyl-1-(4-ethoxy-2,6-difluorobenzyl)-4-methyl-1H-pyrazol-3-yl]-1-(2-methoxyethyl)-1H-1,2,4-triazol-5-yl}pyridin-4-amine;
2-{3-[5-cyclopropyl-1-(4-ethoxy-2,6-difluorobenzyl)-4-methyl-1H-pyrazol-3-yl]-5-(pyridin-4-ylamino)-1H-1,2,4-triazol-1-yl}ethanol;
N-{3-[5-cyclopropyl-1-(4-ethoxy-2,6-difluorobenzyl)-4-methyl-1H-pyrazol-3-yl]-1H-1,2,4-triazol-5-yl}pyridin-4-amine; and
ethyl 4-({3-[5-cyclopropyl-1-(4-ethoxy-2,6-difluorobenzyl)-4-methyl-1H-pyrazol-3-yl]-1-(2-methoxyethyl)-1H-1,2,4-triazol-5-yl}amino)nicotinate,
or an N-oxide, a salt, a tautomer or a stereoisomer of said compound, or a salt of said N-oxide, tautomer or stereoisomer.

6. A method for the treatment of cervical cancer comprising administering to a patient in need thereof a therapeutically effective amount of a compound according to claim 1.

7. A pharmaceutical composition comprising a compound according to claim 1, or an N-oxide, a salt, a tautomer or a stereoisomer of said compound, or a salt of said N-oxide, tautomer or stereoisomer, together with at least one pharmaceutically acceptable carrier or auxiliary.

8. A pharmaceutical combination comprising a compound according to claim 1, or an N-oxide, a salt, a tautomer or a stereoisomer of said compound, or a salt of said N-oxide, tautomer or stereoisomer, and one or more chemotherapeutic anti-cancer agents or target-specific anti-cancer agents.

* * * * *